(12) United States Patent
Sircar et al.

(10) Patent No.: US 7,256,287 B2
(45) Date of Patent: Aug. 14, 2007

(54) PHENYL-AZA-BENZIMIDAZOLE COMPOUNDS FOR MODULATING IGE AND INHIBITING CELLULAR PROLIFERATION

(75) Inventors: Jagadish C. Sircar, San Diego, CA (US); Richard J. Thomas, San Diego, CA (US); Mark L. Richards, La Jolla, CA (US); Anjana Sinha, San Diego, CA (US)

(73) Assignee: Avanir Pharmaceuticals, San Diego, CA (US)

( * ) Notice: Subject to any disclaimer, the term of this patent is extended or adjusted under 35 U.S.C. 154(b) by 671 days.

(21) Appl. No.: 10/661,296

(22) Filed: Sep. 12, 2003

(65) Prior Publication Data

US 2004/0116466 A1 Jun. 17, 2004

Related U.S. Application Data

(60) Provisional application No. 60/410,761, filed on Sep. 12, 2002.

(51) Int. Cl.
*C07D 237/26* (2006.01)
*C07D 237/28* (2006.01)
*C07D 239/00* (2006.01)
*C07D 257/08* (2006.01)
*C07D 251/00* (2006.01)

(52) U.S. Cl. .............. 544/235; 544/253; 544/349; 544/179; 544/180; 546/118

(58) Field of Classification Search ............... 546/118; 544/235, 253, 349, 179, 180
See application file for complete search history.

(56) References Cited

U.S. PATENT DOCUMENTS

| | | | |
|---|---|---|---|
| 3,985,891 A | 10/1976 | Kutter et al. | |
| 4,510,158 A | 4/1985 | Bailey | |
| 4,582,837 A | 4/1986 | Hauel et al. | |
| 4,696,931 A | 9/1987 | Hauel et al. | |
| 5,017,467 A | 5/1991 | Masukawa et al. | |
| 5,124,336 A | 6/1992 | Bru-Magniez et al. | |
| 5,322,847 A | 6/1994 | Marfat et al. | |
| 5,380,865 A | 1/1995 | Cramp et al. | |
| 5,643,893 A | 7/1997 | Benson et al. | |
| 5,712,392 A | 1/1998 | Thurkauf et al. | |
| 5,821,258 A | 10/1998 | Matsunaga et al. | |
| 5,935,983 A | 8/1999 | Muller-Gliemann et al. | |
| 6,093,728 A | 7/2000 | McMahon et al. | |
| 6,100,282 A | 8/2000 | Alig et al. | |
| 6,100,283 A | 8/2000 | Griffin et al. | |
| 6,153,631 A | 11/2000 | Petrie et al. | |
| 6,271,249 B1 | 8/2001 | Romine et al. | |
| 6,271,390 B1 | 8/2001 | Sircar et al. | |
| 6,288,101 B1 | 9/2001 | Glennon | |
| 6,303,645 B1 | 10/2001 | Sircar et al. | |
| 6,369,091 B1 | 4/2002 | Sircar et al. | |
| 6,387,938 B1 | 5/2002 | Mizuguchi et al. | |
| 6,451,829 B2 | 9/2002 | Sircar et al. | |
| 6,486,153 B1 | 11/2002 | Castro Pineiro et al. | |
| 6,503,938 B1 | 1/2003 | Von Angerer et al. | |
| 6,509,365 B1 | 1/2003 | Lubisch et al. | |
| 6,537,994 B2 | 3/2003 | Ashwell et al. | |
| 6,759,425 B2 | 7/2004 | Sircar et al. | |
| 6,911,462 B2 | 6/2005 | Sircar et al. | |
| 6,919,366 B2 | 7/2005 | Sircar et al. | |
| 2002/0010343 A1 | 1/2002 | Sircar et al. | |
| 2002/0132808 A1 | 9/2002 | Sircar et al. | |
| 2003/0004203 A1 | 1/2003 | Sircar et al. | |
| 2003/0100582 A1 | 5/2003 | Sircar et al. | |
| 2004/0180946 A1 | 9/2004 | Sircar et al. | |
| 2004/0214821 A1 | 10/2004 | Sircar et al. | |
| 2004/0229927 A1 | 11/2004 | Sircar et al. | |
| 2005/0075343 A1 | 4/2005 | Sircar et al. | |
| 2005/0085519 A1* | 4/2005 | Rubin et al ................. 514/367 |
| 2005/0197375 A1 | 9/2005 | Sircar et al. | |
| 2005/0256179 A1 | 11/2005 | Sircar et al. | |
| 2005/0277686 A1 | 12/2005 | Sircar et al. | |

FOREIGN PATENT DOCUMENTS

| | | |
|---|---|---|
| EP | 0 221 146 A1 | 5/1987 |
| EP | 0 221 346 A1 | 5/1987 |
| EP | 0 232 199 A2 | 8/1987 |
| EP | 0 353 606 A2 | 2/1990 |

(Continued)

OTHER PUBLICATIONS

Farina et al., IL Farmaco,2001, "Novel bone antiresorptive agents that selectively inhibit the osteoclast V-H+-ATPase", vol. 56, pp. 113-116.*

Viscardi et al., Journal of Heterocyclic Chemistry,1990, "Heterocyclic X-azolopyridine Intermediates",vol. 27, pp. 1825-1829.*

T. Inoue, et al., "Preparation of Isoquinoline isochroman and derivatives for treating virus infectious diseases", Chemical Abstracts 139:307690, STN Search Accession No. 2003:796470.

P.K. Dubey, et al., "Studies on the condensation of 2,3 -pyridinediamines with 2-phenyl -3, 1-benzoxazine-4 (H) -one". Chemical Abstracts 131:322578, STN Search Accession No. 1999:580827.

(Continued)

*Primary Examiner*—Margaret D. Seaman
*Assistant Examiner*—Niloofar Rahmani
(74) *Attorney, Agent, or Firm*—Knobbe, Martens, Olson & Bear, LLP

(57) ABSTRACT

The present invention is directed to small molecule inhibitors of the IgE response to allergens, which are useful in the treatment of allergy and/or asthma or any diseases where IgE is pathogenic. This invention also relates to phenyl-aza-benzimidazole molecules that are cellular proliferation inhibitors and thus are useful as anticancer agents. This invention further relates to small molecules which suppress cytokines and leukocytes.

17 Claims, No Drawings

FOREIGN PATENT DOCUMENTS

| | | |
|---|---|---|
| EP | 0385 850 A2 | 2/1990 |
| EP | 415 886 A2 | 8/1990 |
| EP | 0 469 477 A1 | 2/1992 |
| EP | 0 497 564 A1 | 8/1992 |
| EP | 0 694 535 A1 | 1/1996 |
| EP | 0 700 906 A1 | 3/1996 |
| EP | 0 719 765 A2 | 7/1996 |
| EP | 1 077 700 A1 | 2/2001 |
| EP | 1 125 936 A2 | 8/2001 |
| JP | 06 263993 A | 9/1994 |
| SU | 1316559 | 6/1983 |
| WO | WO 89 06975 | 8/1989 |
| WO | WO 90 09989 | 9/1990 |
| WO | WO 92 02500 | 2/1992 |
| WO | WO 93 25517 | 12/1993 |
| WO | WO 98 17267 | 4/1998 |
| WO | WO 98 47890 | 10/1998 |
| WO | WO 98 56761 | 12/1998 |
| WO | WO 99 61013 A1 | 12/1999 |
| WO | WO 99 61019 A1 | 12/1999 |
| WO | WO 99 61020 A1 | 12/1999 |
| WO | WO 00 26192 A1 | 5/2000 |
| WO | WO 00 29384 A1 | 5/2000 |
| WO | WO 00 32579 A1 | 6/2000 |
| WO | WO 00 64878 A1 | 11/2000 |
| WO | WO 00 68206 A1 | 11/2000 |
| WO | WO 01 12169 A2 | 2/2001 |
| WO | WO 01 14342 A1 | 3/2001 |
| WO | WO 01 72737 A1 | 10/2001 |
| WO | WO 02 72090 | 9/2002 |
| WO | WO 02 072539 A1 | 9/2002 |
| WO | WO 02 072574 A1 | 9/2002 |
| WO | WO 2004/024896 A3 | 3/2004 |

OTHER PUBLICATIONS

Related pending U.S. Appl. No. 10/661,139, filed Sep. 12, 2003. Title: Phenyl-Indole Compounds for Modulating IgE and Inhibiting Cellular Proliferation. Inventors: Jagadish C. Sircar et al.

Related pending U.S. Appl. No. 10/794,006, filed Mar. 5, 2004. Title: Benzimidazole Compounds for Modulating IgE and Inhibiting Cellular Proliferation. Inventors: Jagadish C. Sircar et al.

Related pending U.S. Appl. No. 10/821,667, filed Apr. 9, 2004. Title: Imidazole Derivatives for Treatment of Allergic and Hyperproliferative Disorders. Inventors: Jagadish C. Sircar et al.

Related pending U.S. Appl. No. 10/915,722, filed Aug. 9, 2004. Title: Selective Pharmacologic Inhibition of Protein Trafficking and Related Methods of Treating Human Diseases. Inventors: Jagadish C. Sircar et al.

Related pending U.S. Appl. No. 10/508,968, filed Sep. 24, 2004. Title: Use of Benzimidazole Analogs in the Treatment of Cell Proliferation. Inventors: Jagadish C. Sircar et al.

Related pending U.S. Appl. No. 10/951,515, filed Sep. 28, 2004. Title: Benzimidazole Derivatives as Modulators of IgE. Inventors: Jagadish C. Sircar et al.

Related pending U.S. Appl. No. 11/168,711, filed Jun. 28, 2005. Title: Benzimidazole Compounds for Regulating IgE. Inventors: Jagadish C. Sircar et al.

Manecke et al., Über Polyamide mit 2,4-Imidazolidiyl-Bausteinen, Die Makromolekulare Chemie 176, pp. 3551-3563 (1975), Apr. 29, 1975, Institut für Organische Chemie der Freien Universität Berline, D-1 Berlin 33.

Cheney B V, et al., "Structure-activity, Correlations for a Series of Antiallergy Agents. 3. Development of a Quantitative Model," Journal of Medicinal Chemistry, vol. 26, No. 5, 1983, pp. 726-737.

Pozdnyakov et al., "Mass Spectrometric Study of Dissociative Ionization of Low-molecular Models of Aromatic Polyamides," Khim. Vys. Energ. (1987), 21(1), 38-44 Coden; Khvkao; ISSN: 0023-1193, 1987.

English language abstract of Pozdnyakov, et al. (1987) "Mass spectrometric study of dissociative ionization of low-molecular models of aromatic polyamides," vol. 21 (1), pp. 38-44.

Database Crossfire Beilstein 'Online!, Beilstein Institut zur Forderung der Chemischen Wissenchaften, Frankfurt am Main, DE; Beilstein Registry No. 563073 & Khim. Farm. ZH., vol. 22, No. 6, 1988, pp. 697-699.

Karag'ozov S, "Synthesis of N-acyl Derivatives of 6-amio-1-4-benzodioXane," STN International, vol. 39, No. 1989 pp. 5-8, Abstract only.

Masukawa et al., Calplus 111:31259 (EP 304856, Mar. 1, 1989).

Denny W A et al., "Potential antitumor agents. 59. Structure-activity relationships for 2-phenylbenzimidazole-4-carboXamides, a new class of "minimal" DNA-intercalating agents which may not act via topoisomerase II", Journal of Medicinal Chemistry, vol. 33, No. 2, Feb. 1990, pp. 814-819.

Yilder I, "Synthesis of 32-(substitutephenyl) Benzimidazole Derivatives and their Sedative Activity: Structure-activity Relationships," Journal FaX. Pharm. Gazi Uni., vol. 7, No. 2, 1990, pp. 111-114.

Timothy F. Gallagher, et al., "2,4,5-Triarylimidazole Inhibitors of IL-1 Biosynthesis," Bioorganic & Medicinal Chemistry Letters, vol. 5, No. 11, pp. 1171-1176, 1995.

Ashton et al., "New Low-Density Lipoprotein Receptor Upregulators Acting via a Novel Mechanism," Journal of Medicinal Chemistry, vol. 39, Jan. 1, 1996, pp. 3343-3356.

Krieg et al., ber einige Imidazolderivate, Chem. Ber. 100, pp. 4042-4049 (1967), Jun. 28, 1997, Jahrg. 100, Aus dem Institut für Organische Chemie der Freien Universität Berlin, Berlin-Dahlem.

Kreimeyer A et al., "Suramin analogues with a 2-phenylbenzimidazole moiety as partyial structure; potential anti HIV-and angiostic drugs, 2: Sulfanilic acid, benzendisulfonic, and naphthalentrisulfonic acid analogues" Archi Der Pharmazie, vol. 331, No. 3, Mar. 1998, pp. 97-103.

Japanese Application No. 10273013, entitled Antagonist for Gonadotrophic Hormone-Releasing Hormone, filed on Sep. 28, 1998, English abstract only.

Database Caplus 'Online! Chemical Abstracts Service, Columbus, Ohio, US; Databse accession No. 2000:214835 & JP 2000 095767 (Takeda Chemical Industries, Ltd.), Apr. 4, 2000.

White A W et al., "Resistance-modifying agents. 9. Synthesis and biological properties of benzimidazole inhibitors of the DNA repair enzyme poly(ADP-ribose) polymerase", Journal of Medicinal Chemistry, vol. 43, No. 2, Nov. 2, 2000, pp. 4084-4097.

Chilean Office Action with Search Report for the Chilean countepart of the U.S Appl. No. 10/795,006.

Chemical structure database (CA, Caplus, Chemcats) search results for bis-5,4'-dibenzanilide-2- phenylbenzimidazole (Registry No. 98806-53-2).

Golub et al., Science, vol. 286, Oct. 15, 1999, pp. 531-537.

* cited by examiner

PHENYL-AZA-BENZIMIDAZOLE COMPOUNDS FOR MODULATING IGE AND INHIBITING CELLULAR PROLIFERATION

CROSS-REFERENCE TO RELATED APPLICATIONS

This application claims priority under 35 U.S.C. § 119(e) to U.S. Provisional Patent Application No. 60/410,761, filed Sep. 12, 2002.

BACKGROUND OF THE INVENTION

1. Field of the Invention

This invention relates to small molecule inhibitors of the IgE response to allergens that are useful in the treatment of allergy and/or asthma or any diseases where IgE is pathogenic. This invention also relates to small molecules that are proliferation inhibitors and thus they are useful as anticancer agents. This invention further relates to small molecules which suppress cytokines and leukocytes.

2. Description of the Related Art

Allergies and Asthma

An estimated 10 million persons in the United States have asthma, about 5% of the population. The estimated cost of asthma in the United States exceeds $6 billion. About 25% of patients with asthma who seek emergency care require hospitalization, and the largest single direct medical expenditure for asthma has been inpatient hospital services (emergency care), at a cost of greater than $1.6 billion. The cost for prescription medications, which increased 54% between 1985 and 1990, was close behind at $1.1 billion (Kelly, *Pharmacotherapy* 12:13S-21S (1997)).

According to the National Ambulatory Medical Care Survey, asthma accounts for 1% of all ambulatory care visits, and the disease continues to be a significant cause of missed school days in children. Despite improved understanding of the disease process and better drugs, asthma morbidity and mortality continue to rise in this country and worldwide (U.S. Department of Health and Human Services; 1991, publication no. 91-3042). Thus, asthma constitutes a significant public health problem.

The pathophysiologic processes that attend the onset of an asthmatic episode can be broken down into essentially two phases, both marked by bronchoconstriction, that causes wheezing, chest tightness, and dyspnea. The first, early phase asthmatic response is triggered by allergens, irritants, or exercise. Allergens cross-link immunoglobulin E (IgE) molecules bound to receptors on mast cells, causing them to release a number of pre-formed inflammatory mediators, including histamine. Additional triggers include the osmotic changes in airway tissues following exercise or the inhalation of cold, dry air. The second, late phase response that follows is characterized by infiltration of activated eosinophils and other inflammatory cells into airway tissues, epithelial desquamonon, and by the presence of highly viscous mucus within the airways. The damage caused by this inflammatory response leaves the airways "primed" or sensitized, such that smaller triggers are required to elicit subsequent asthma symptoms.

A number of drugs are available for the palliative treatment of asthma; however, their efficacies vary markedly. Short-acting $\beta_2$-adrenergic agonists, terbutaline and albuterol, long the mainstay of asthma treatment, act primarily during the early phase as bronchodilators. The newer long-acting $\beta_2$-agonists, salmeterol and formoterol, may reduce the bronchoconstrictive component of the late response. However, because the $\beta_2$-agonists do not possess significant antiinflammatory activity, they have no effect on bronchial hyperreactivity.

Numerous other drugs target specific aspects of the early or late asthmatic responses. For example, antihistamines, like loratadine, inhibit early histamine-mediated inflammatory responses. Some of the newer antihistamines, such as azelastine and ketotifen, may have both antiinflammatory and weak bronchodilatory effects, but they currently do not have any established efficacy in asthma treatment. Phosphodiesterase inhibitors, like theophylline/xanthines, may attenuate late inflammatory responses, but there is no evidence that these compounds decrease bronchial hyperreactivity. Anticholinergics, like ipratopium bromide, which are used in cases of acute asthma to inhibit severe bronchoconstriction, have no effect on early or late phase inflammation, no effect on bronchial hyperreactivity, and therefore, essentially no role in chronic therapy.

The corticosteroid drugs, like budesonide, are the most potent antiinflammatory agents. Inflammatory mediator release inhibitors, like cromolyn and nedocromil, act by stabilizing mast cells and thereby inhibiting the late phase inflammatory response to allergen. Thus, cromolyn and nedocromil, as well as the corticosteroids, all reduce bronchial hyperreactivity by minimizing the sensitizing effect of inflammatory damage to the airways. Unfortunately, these antiinflammatory agents do not produce bronchodilation.

Several new agents have been developed that inhibit specific aspects of asthmatic inflammation. For instance, leukotriene receptor antagonists (ICI-204, 219, accolate), specifically inhibit leukotriene-mediated actions. The leukotrienes have been implicated in the production of both airway inflammation and bronchoconstriction.

Thus, while numerous drugs are currently available for the treatment of asthma, these compounds are primarily palliative and/or have significant side effects. Consequently, new therapeutic approaches which target the underlying cause rather than the cascade of symptoms would be highly desirable. Asthma and allergy share a common dependence on IgE-mediated events. Indeed, it is known that excess IgE production is the underlying cause of allergies in general and allergic asthma in particular (Duplantier and Cheng, *Ann. Rep. Med. Chem.* 29:73-81 (1994)). Thus, compounds that lower IgE levels may be effective in treating the underlying cause of asthma and allergy.

None of the current therapies eliminate the excess circulating IgE. The hypothesis that lowering plasma IgE may reduce the allergic response, was confirmed by recent clinical results with chimeric anti-IgE antibody, CGP-51901, and recombinant humanized monoclonal antibody, rhuMAB-E25. Indeed, three companies, Tanox Biosystems, Inc., Genentech Inc. and Novartis AG are collaborating in the development of a humanized anti-IgE antibody (BioWorld® Today, Feb. 26, 1997, p. 2) which will treat allergy and asthma by neutralizing excess IgE. Tanox has already successfully tested the anti-IgE antibody, CGP-51901, which reduced the severity and duration of nasal symptoms of allergic rhinitis in a 155-patient Phase II trial (Scrip #2080, Nov. 24, 1995, p.26). Genentech recently disclosed positive results from a 536 patient phase-II/III trials of its recombinant humanized monoclonal antibody, rhuMAB-E25 (BioWorld® Today, Nov. 10, 1998, p. 1). The antibody, rhuMAB-E25, administered by injection (highest dose 300 mg every 2 to 4 weeks as needed) provided a 50% reduction in the number of days a patient required additional "rescue" medicines (antihistimines and decongestants), compared to placebo. More recently, Dr. Henry Milgrom et. al. of the National Jewish Medical and Research Center in Denver, Colo., published the clinical results of rhuMAB-25 in moderate to severe asthma patients (317 patients for 12 weeks, iv injection every two weeks) and concluded that this drug is "going to be a breakthrough" (New England Journal of Medicine, Dec. 23, 1999). A Biologics License Application (BLA) for this product has been submitted to the FDA in June, 2000 jointly by Novartis Pharmaceuticals Corporation, Tanox Inc., and Genentech, Inc. The positive results from anti-IgE antibody trials suggest that therapeutic strategies aimed at IgE down-regulation may be effective.

Cancer and Hyperproliferation Disorders

Cellular proliferation is a normal process that is vital to the normal functioning of most biological processes. Cellular proliferation occurs in all living organisms and involves two main processes: nuclear division (mitosis), and cytoplasmic division (cytokinesis). Because organisms are continually growing and replacing cells, cellular proliferation is essential to the vitality of the healthy cell. The disruption of normal cellular proliferation can result in a variety of disorders. For example, hyperproliferation of cells may cause psoriasis, thrombosis, atherosclerosis, coronary heart disease, myocardial infarction, stroke, smooth muscle neoplasms, uterine fibroid or fibroma, and obliterative diseases of vascular grafts and transplanted organs. Abnormal cell proliferation is most commonly associated with tumor formation and cancer.

Cancer is a major disease and is one of the leading causes of mortality both in the United States and internationally. Indeed, cancer is the second leading cause of death in the United States. According to the National Institute of Health, the overall annual cost for cancer is approximately $107 billion, which includes $37 billion for direct medical costs, $11 billion for indirect costs of lost productivity due to illness and $59 billion for indirect costs of lost productivity due to premature death. Not surprisingly, considerable efforts are underway to develop new treatments and preventative measures to combat this devastating illness.

Currently, cancer is primarily treated using a combination of surgery, radiation and chemotherapy. Chemotherapy involves the use of chemical agents to disrupt the replication and metabolism of cancerous cells. Chemotherapeutic agents which are currently being used to treat cancer can be classified into five main groups: natural products and their derivatives; anthacyclines; alkylating agents; antiproliferatives and hormonal agents.

SUMMARY OF THE INVENTION

It is one object of several embodiments of the present invention to provide aza-benzimidazole compounds and methods thereof to modulate IgE. It is another object to provide aza-benzimidazole compositions and methods to inhibit cell proliferation. It is yet another object of several embodiments of the current invention to inhibit cytokines and leukocytes, including but not limited to IL-4, IL-5, eosinophils and lymphocytes.

The following series of compounds, identified under subheadings Supragenus A-D and Genus A1-A5, B1-B4, C1-C4, and D1-D4 were found to be potent inhibitors of IgE in both ex-vivo and in vivo models. These compounds also exhibit anti-proliferative effects, and, as such, may be used as agents to treat hyperproliferation disorders, including cancer.

Families of small molecule IgE inhibitors are defined by the following supragenera, including Supragenus A (Genera A1-A5), Supragenus B (Genera B1-B4), Supragenus C (Genera C1-C4) and Supragenus D (Genera D1-D4):

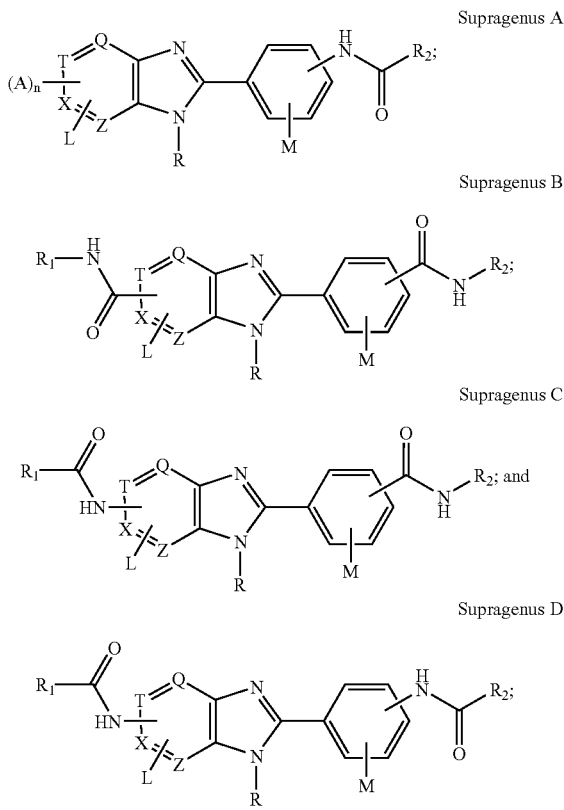

wherein Q. T, X, and Z are independently selected from N or C, and wherein one of Q, T, X, and Z is N;

wherein A is selected from the group consisting of H, halogen, and $CONHR_1$;

wherein n is a number from one to four;

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Preferred embodiments include species in which $R_1$ and $R_2$ are aliphatic groups. Preferred embodiments include species of Supragenera A and D, as shown by formulas S-1 to S-25.

One family of small molecules of several embodiments is defined by the following genus (Genus A1):

Genus A1

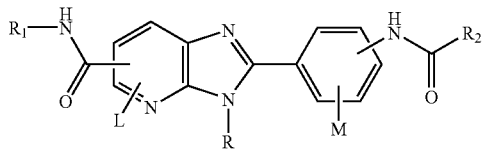

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus A2):

Genus A2

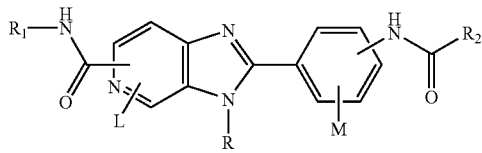

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus A3):

Genus A3

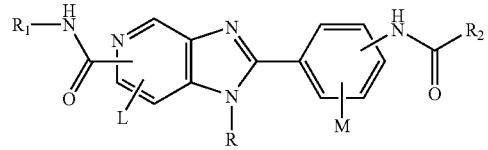

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, OCH₃, COOH, COOR'COR', CN, CF₃, OCF₃, NO₂, NR'R', NHCOR' and CONR'R'; and wherein R' is selected from the group consisting of H, alkyl, substituted alkyl, C₃-C₉ cycloalkyl, substituted C₃-C₉ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus A4):

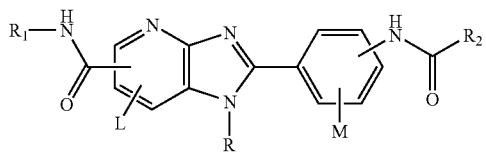

Genus A4 wherein L and M are independently selected from the group consisting of H, alkyl, alkoxy, aryl, substituted aryl, hydroxy, halogen, amino, alkylamino, nitro, cyano, CF₃, OCF₃, CONH₂, CONHR and NHCOR₁;

wherein R is selected from the group consisting of H, C₁-C₅ alkyl, benzyl, p-fluorobenzyl and di-alkylamino alkyl, wherein said C₁-C₅ alkyl is selected from the group consisting of a straight chain, branched or cyclic alkyl;

wherein R₁ and R₂ are independently selected from the group consisting of H, alkyl, substituted alkyl, C₃-C₉ cycloalkyl, substituted C₃-C₉ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, OCH₃, COOH, COOR'COR', CN, CF₃, OCF₃, NO₂, NR'R', NHCOR' and CONR'R'; and wherein R' is selected from the group consisting of H, alkyl, substituted alkyl, C₃-C₉ cycloalkyl, substituted C₃-C₉ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus A5):

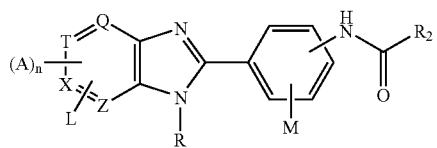

Genus A5 wherein Q, T, X, and Z are independently selected from N or C, and wherein one of Q, T, X, and Z is N;

wherein A is selected from the group consisting of H and halogen;

wherein n is a number from one to four;

wherein L and M are independently selected from the group consisting of H, alkyl, alkoxy, aryl, substituted aryl, hydroxy, halogen, amino, alkylamino, nitro, cyano, CF₃, OCF₃, CONH₂, CONHR and NHCOR₁;

wherein R is selected from the group consisting of H, C₁-C₅ alkyl, benzyl, p-fluorobenzyl and di-alkylamino alkyl, wherein said C₁-C₅ alkyl is selected from the group consisting of a straight chain, branched or cyclic alkyl;

wherein R₁ and R₂ are independently selected from the group consisting of H, alkyl, substituted alkyl, C₃-C₉ cycloalkyl, substituted C₃-C₉ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, OCH₃, COOH, COOR'COR', CN, CF₃, OCF₃, NO₂, NR'R', NHCOR' and CONR'R'; and wherein R' is selected from the group consisting of H, alkyl, substituted alkyl, C₃-C₉ cycloalkyl, substituted C₃-C₉ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus B1):

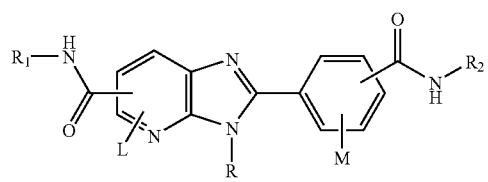

Genus B1 wherein L and M are independently selected from the group consisting of H, alkyl, alkoxy, aryl, substituted aryl, hydroxy, halogen, amino, alkylamino, nitro, cyano, CF₃, OCF₃, CONH₂, CONHR and NHCOR₁;

wherein R is selected from the group consisting of H, C₁-C₅ alkyl, benzyl, p-fluorobenzyl and di-alkylamino alkyl, wherein said C₁-C₅ alkyl is selected from the group consisting of a straight chain, branched or cyclic alkyl;

wherein R₁ and R₂ are independently selected from the group consisting of H, alkyl, substituted alkyl, C₃-C₉ cycloalkyl, substituted C₃-C₉ cycloalkyl, polycyclic aliphatic groups, substituted polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, OCH$_3$, COOH, COOR'COR', CN, CF$_3$, OCF$_3$, NO$_2$, NR'R', NHCOR' and CONR'R'; and wherein R' is selected from the group consisting of H, alkyl, substituted alkyl, C$_3$-C$_9$ cycloalkyl, substituted C$_3$-C$_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus B2):

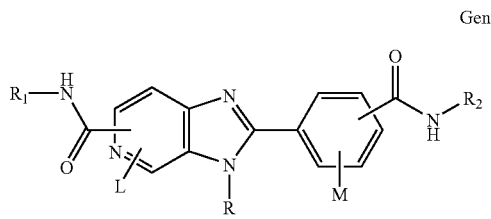

Genus B2 wherein L and M are independently selected from the group consisting of H, alkyl, alkoxy, aryl, substituted aryl, hydroxy, halogen, amino, alkylamino, nitro, cyano, CF$_3$, OCF$_3$, CONH$_2$, CONHR and NHCOR$_1$;

wherein R is selected from the group consisting of H, C$_1$-C$_5$ alkyl, benzyl, p-fluorobenzyl and di-alkylamino alkyl, wherein said C$_1$-C$_5$ alkyl is selected from the group consisting of a straight chain, branched or cyclic alkyl;

wherein R$_1$ and R$_2$ are independently selected from the group consisting of H, alkyl, substituted alkyl, C$_3$-C$_9$ cycloalkyl, substituted C$_3$-C$_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, OCH$_3$, COOH, COOR'COR', CN, CF$_3$, OCF$_3$, NO$_2$, NR'R', NHCOR' and CONR'R'; and wherein R' is selected from the group consisting of H, alkyl, substituted alkyl, C$_3$-C$_9$ cycloalkyl, substituted C$_3$-C$_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus B3):

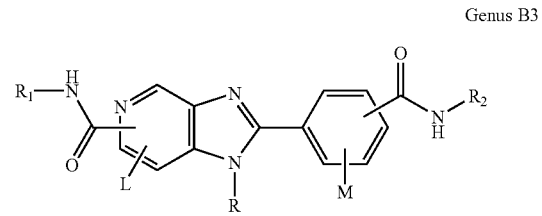

Genus B3 wherein L and M are independently selected from the group consisting of H, alkyl, alkoxy, aryl, substituted aryl, hydroxy, halogen, amino, alkylamino, nitro, cyano, CF$_3$, OCF$_3$, CONH$_2$, CONHR and NHCOR$_1$;

wherein R is selected from the group consisting of H, C$_1$-C$_5$ alkyl, benzyl, p-fluorobenzyl and di-alkylamino alkyl, wherein said C$_1$-C$_5$ alkyl is selected from the group consisting of a straight chain, branched or cyclic alkyl;

wherein R$_1$ and R$_2$ are independently selected from the group consisting of H, alkyl, substituted alkyl, C$_3$-C$_9$ cycloalkyl, substituted C$_3$-C$_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, OCH$_3$, COOH, COOR'COR', CN, CF$_3$, OCF$_3$, NO$_2$, NR'R', NHCOR' and CONR'R'; and wherein R' is selected from the group consisting of H, alkyl, substituted alkyl, C$_3$-C$_9$ cycloalkyl, substituted C$_3$-C$_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus B4):

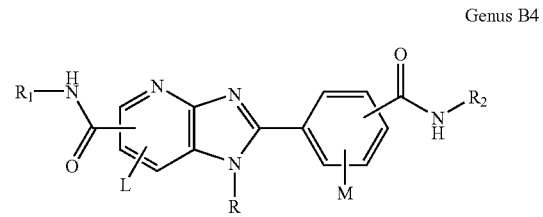

Genus B4 wherein L and M are independently selected from the group consisting of H, alkyl, alkoxy, aryl, substituted aryl, hydroxy, halogen, amino, alkylamino, nitro, cyano, CF$_3$, OCF$_3$, CONH$_2$, CONHR and NHCOR$_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus C1):

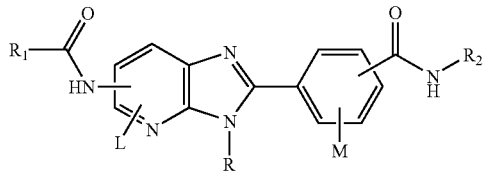

Genus C1 wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus C2):

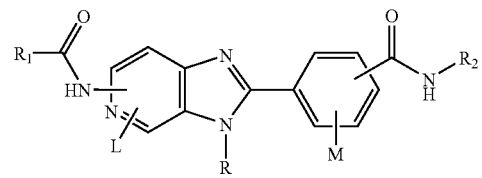

Genus C2 wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus C3):

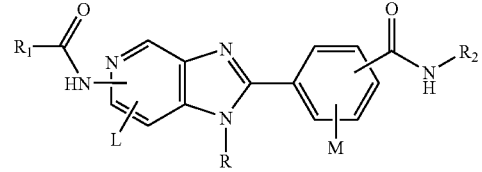

Genus C3 wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus C4):

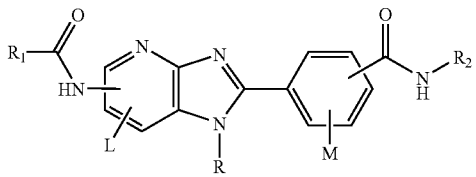

Genus C4 wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus D1):

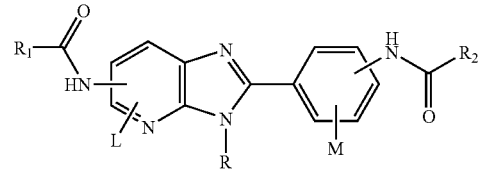

Genus D1 wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus D2):

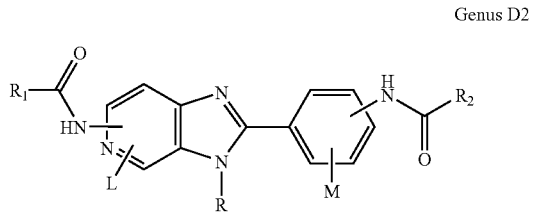

Genus D2 wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus D3):

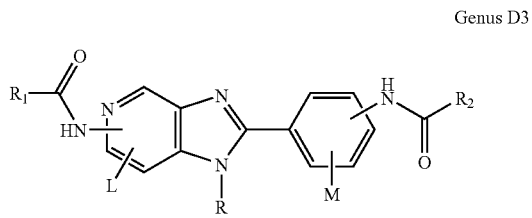

Genus D3 wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

One family of small molecule IgE inhibitors of the preferred embodiments is defined by the following genus (Genus D4):

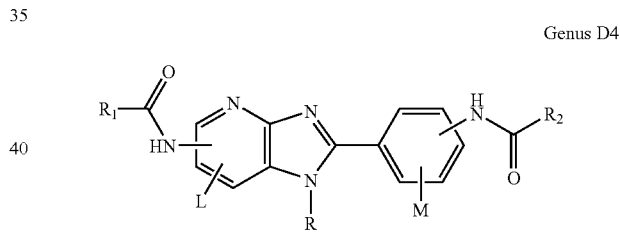

Genus D4 wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, OCH$_3$, COOH, COOR'COR', CN, CF$_3$, OCF$_3$, NO$_2$, NR'R', NHCOR' and CONR'R'; and wherein R' is selected from the group consisting of H, alkyl, substituted alkyl, C$_3$-C$_9$ cycloalkyl, substituted C$_3$-C$_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

A subgenus of preferred embodiments comprises any one or more of the following compounds, as shown as Subgenus D2a:

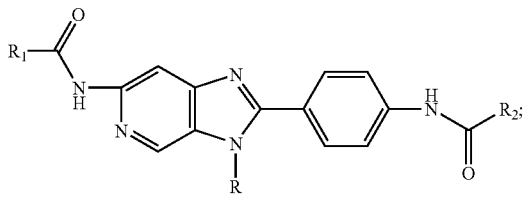

Subgenus D2a wherein R is selected from the group consisting of H, C$_1$-C$_5$ alkyl, benzyl, p-fluorobenzyl and di-alkylamino alkyl, wherein said C$_1$-C$_5$ alkyl is selected from the group consisting of a straight chain, branched or cyclic alkyl;

wherein R$_1$ and R$_2$ are independently selected from the group consisting of H, alkyl, substituted alkyl, C$_3$-C$_9$ cycloalkyl, substituted C$_3$-C$_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, OCH$_3$, COOH, COOR'COR', CN, CF$_3$, OCF$_3$, NO$_2$, NR'R', NHCOR' and CONR'R'; and wherein R' is selected from the group consisting of H, alkyl, substituted alkyl, C$_3$-C$_9$ cycloalkyl, substituted C$_3$-C$_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Another subgenus of preferred embodiments comprises any one or more of the following compounds, as shown as Subgenus D1a:

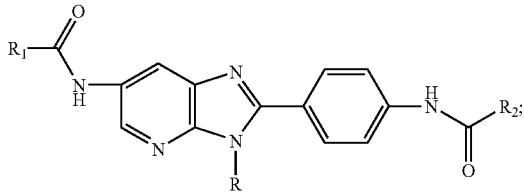

Subgenus D1a wherein R is selected from the group consisting of H, C$_1$-C$_5$ alkyl, benzyl, p-fluorobenzyl and di-alkylamino alkyl, wherein said C$_1$-C$_5$ alkyl is selected from the group consisting of a straight chain, branched or cyclic alkyl;

wherein R$_1$ and R$_2$ are independently selected from the group consisting of H, alkyl, substituted alkyl, C$_3$-C$_9$ cycloalkyl, substituted C$_3$-C$_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, OCH$_3$, COOH, COOR'COR', CN, CF$_3$, OCF$_3$, NO$_2$, NR'R', NHCOR' and CONR'R'; and wherein R' is selected from the group consisting of H, alkyl, substituted alkyl, C$_3$-C$_9$ cycloalkyl, substituted C$_3$-C$_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Another subgenus of preferred embodiments comprises any one or more of the following compounds, as shown as Subgenus D4a:

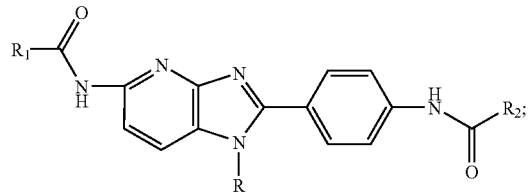

Subgenus D4a wherein R is selected from the group consisting of H, C$_1$-C$_5$ alkyl, benzyl, p-fluorobenzyl and di-alkylamino alkyl, wherein said C$_1$-C$_5$ alkyl is selected from the group consisting of a straight chain, branched or cyclic alkyl;

wherein R$_1$ and R$_2$ are independently selected from the group consisting of H, alkyl, substituted alkyl, C$_3$-C$_9$ cycloalkyl, substituted C$_3$-C$_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, OCH$_3$, COOH, COOR'COR', CN, CF$_3$, OCF$_3$, NO$_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Another subgenus of preferred embodiments comprises any one or more of the following compounds, as shown as Subgenus B1a:

Subgenus B1a

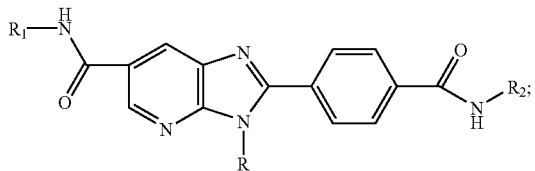

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Another subgenus of preferred embodiments comprises any one or more of the following compounds, as shown as Subgenus A1a:

Subgenus A1a

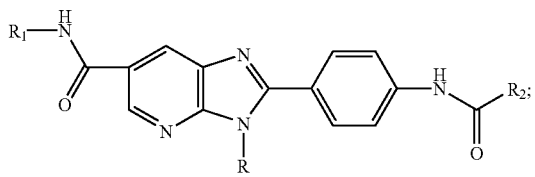

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

For each chemical structure disclosed herein, the hydrogen atoms on the heteroatoms have been omitted for clarity purposes. Where open valences on heteroatoms are indicated, it is assumed that these valences are filled by hydrogen atoms.

A method for treating a disease condition associated with excess IgE and/or abnormal cell proliferation (i.e. cancer) in a mammal is also disclosed. In one aspect, the method comprises the step of administering to the mammal an IgE-suppressing amount or anti-cell proliferation amount of a pharmaceutical formulation comprising at least one aza-benzimidazole compound from the above-disclosed small molecule families.

In accordance with a variation of the method of treatment, the small molecule IgE-suppressing compound may be administered in conjunction with at least one additional agent, which is active in reducing a symptom associated with an allergic reaction. In one embodiment, the small molecule inhibitor may be mixed with at least one additional active ingredient to form a pharmaceutical composition. Alternatively, the small molecule inhibitor may be co-administered at the same time or according to different treatment regimens with the at least one additional active agent.

The at least one additional active ingredient may be a short-acting $\beta_2$-adrenergic agonist selected from the group consisting of terbutaline and albuterol; a long-acting $\beta_2$-adrenergic agonist selected from the group consisting of salmeterol and formoterol; an antihistamine selected from the group consisting of loratadine, azelastine and ketotifen; a phosphodiesterase inhibitor, an anticholinergic agent, a corticosteroid, an inflammatory mediator release inhibitor or a leukotriene receptor antagonist.

In another embodiment, the aza-benzimidazole compound may be administered in conjunction with at least one additional active agent. These active agents include antifungals, antivirals, antibiotics, anti-inflammatories, and anticancer agents. Anticancer agents include, but are not limited to, alkylating agents (lomustine, carmustine, streptozocin, mechlorethamine, melphalan, uracil nitrogen mustard, chlorambucil cyclophosphamide, iphosphamide, cisplatin, carboplatin mitomycin thiotepa dacarbazine procarbazine, hexamethyl melamine, triethylene melamine, busulfan, pipobroman, and mitotane); antimetabolites (methotrexate, trimetrexate pentostatin, cytarabine, ara-CMP, fludarabine phosphate, hydroxyurea, fluorouracil, floxuridine, chlorodeoxyadenosine, gemcitabine, thioguanine, and 6-mercaptopurine); DNA cutters (bleomycin); topoisomerase I poisons (topotecan irinotecan and camptothecin); topoisomerase II poisons (daunorubicin, doxorubicin, idarubicin, mitoxantrone, teniposide, and etoposide); DNA binders (dactinomycin, and mithramycin); and spindle poisons (vinblastine, vincristine, navelbine, paclitaxel, and docetaxel).

In another embodiment, the aza-benzimidazole compounds of the preferred embodiments are administered in conjunction with one or more other therapies. These therapies include, but are not limited to radiation, immunotherapy, gene therapy and surgery. These combination therapies may be administered simultaneously or sequentially. For example, radiation may be administered along with the administration of aza-benzimidazole compounds, or may be administered at any time before or after administration of aza-benzimidazole compounds.

A dose of about 0.01 mg to about 100 mg per kg body weight per day of the small molecule IgE inhibitory compound is preferably administered in divided doses daily.

A method for treating a disease condition associated with excess IgE or abnormal cell proliferation in a mammal is also disclosed which comprises the step of administering to the mammal an therapeutic amount of a pharmaceutical formulation comprising at least one compound selected from Supragenera A-D.

The methods provided herein for treating diseases and processes mediated by undesired, uncontrolled or abnormal cell proliferation, such as cancer, involve administering to a mammal a composition of the aza-benzimidazole compounds disclosed herein to inhibit cell proliferation. The method is particularly useful for preventing or treating tumor formation and progression. In the preferred embodiments, the compounds and methods disclosed are especially useful in treating estrogen receptor positive and estrogen receptor negative type breast cancers.

Other variations within the scope of the present invention may be more fully understood with reference to the following detailed description.

DETAILED DESCRIPTION OF THE PREFERRED EMBODIMENT

The preferred embodiments are directed to small molecule inhibitors of IgE which are useful in the treatment of allergy and/or asthma or any diseases where IgE is pathogenic. The inhibitors may affect the synthesis, activity, release, metabolism, degradation, clearance and/or pharmacokinetics of IgE. The particular compounds disclosed herein were identified by their ability to suppress IgE levels in both ex vivo and in vivo assays. The compounds disclosed in the preferred embodiments are also useful in the treatment of diseases associated with abnormal cellular proliferation, including, but not limited to, tumorgenesis and other proliferative diseases such as cancers, inflammatory disorders and circulatory diseases. Development and optimization of clinical treatment regimens can be monitored by those of skill in the art by reference to the ex vivo and in vivo assays described below. In addition, several embodiments of the current invention are directed to aza-benzimidazole compounds that inhibit cytokines and leukocytes, including but not limited to IL-4, IL-5, eosinophils and lymphocytes.

Ex Vivo Assay

This system begins with in vivo antigen priming and measures secondary antibody responses in vitro. The basic protocol was documented and optimized for a range of parameters including: antigen dose for priming and time span following priming, number of cells cultured in vitro, antigen concentrations for eliciting secondary IgE (and other Ig's) response in vitro, fetal bovine serum (FBS) batch that will permit optimal IgE response in vitro, the importance of primed CD4+ T cells and hapten-specific B cells, and specificity of the ELISA assay for IgE (Marcelletti and Katz, *Cellular Immunology* 135:471-489 (1991); incorporated herein by reference).

The actual protocol utilized for this project was adapted for a more high throughput analyses. BALB/cByj mice were immunized i.p. with 10 µg DNP-KLH adsorbed onto 4 mg alum and sacrificed after 15 days. Spleens were excised and homogenized in a tissue grinder, washed twice, and maintained in DMEM supplemented with 10% FBS, 100 U/ml penicillin, 100 µg/ml streptomycin and 0.0005% 2-mercaptoethanol. Spleen cell cultures were established (2-3 million cells/ml, 0.2 ml/well in quadruplicate, 96-well plates) in the presence or absence of DNP-KLH (10 ng/ml). Test compounds (2 µg/ml and 50 ng/ml) were added to the spleen cell cultures containing antigen and incubated at 37° C. for 8 days in an atmosphere of 10% $CO_2$.

Culture supernatants were collected after 8 days and Ig's were measured by a modification of the specific isotype-selective ELISA assay described by Marcelletti and Katz (supra). The assay was modified to facilitate high throughput. ELISA plates were prepared by coating with DNP-KLH or DNP-OVA overnight. After blocking with bovine serum albumin (BSA), an aliquot of each culture supernatant was diluted (1:4 in phosphate buffered saline (PBS) with BSA, sodium azide and Tween 20), added to the ELISA plates, and incubated overnight in a humidified box at 4° C. IgE levels were quantitated following successive incubations with biotinylated-goat antimouse IgE (b-GAME), AP-streptavidin and substrate.

Antigen-specific IgG1 was measured similarly, except that culture supernatants were diluted 200-fold and biotinylated-goat antimouse IgG1 (b-GAMG1) was substituted for b-GAME. IgG2a was measured in ELISA plates that were coated with DNP-KLH following a 1:20 dilution of culture supernatants and incubation with biotinylated-goat antimouse IgG2a (b-GAMG2a). Quantitation of each isotype was determined by comparison to a standard curve. The level of detectability of all antibody was about 200-400 pg/ml and there was less than 0.001% cross-reactivity with any other Ig isotype in the ELISA for IgE.

In Vivo Assay

Compounds found to be active in the ex vivo assay (above) were further tested for their activity in suppressing IgE responses in vivo. Mice receiving low-dose radiation prior to immunization with a carrier exhibited an enhanced IgE response to challenge with antigen 7 days later. Administration of the test compounds immediately prior to and after antigen sensitization, measured the ability of that drug to suppress the IgE response. The levels of antigen specific IgE, IgG1 and IgG2a in serum were compared.

Female BALB/cByj mice were irradiated with 250 rads 7 hours after initiation of the daily light cycle. Two hours later, the mice were immunized i.p. with 2 µg of KLH in 4 mg alum. Two to seven consecutive days of drug injections were initiated 6 days later on either a once or twice daily basis. Typically, i.p. injections and oral gavages were administered as suspensions (150 μl/injection) in saline with 10% ethanol and 0.25% methylcellulose. Each treatment group was composed of 5-6 mice. On the second day of drug administration, 2 μg of DNP-KLH was administered i.p. in 4 mg alum, immediately following the morning injection of drug. Mice were bled 7-21 days following DNP-KLH challenge.

Antigen-specific IgE, IgG1 and IgG2a antibodies were measured by ELISA. Periorbital bleeds were centrifuged at 14,000 rpm for 10 min, the supernatants were diluted 5-fold in saline, and centrifuged again. Antibody concentrations of each bleed were determined by ELISA of four dilutions (in triplicate) and compared to a standard curve: anti-DNP IgE (1:100 to 1:800), anti-DNP IgG2a (1:100 to 1:800), and anti-DNP IgG1 (1:1600 to 1:12800).

Active Compounds of Preferred Embodiments

The following series of compounds, identified under subheadings Supragenus A-D and Genus A1-A5, B1-B4, C1-C4, and D1-D4 were found to be potent inhibitors of IgE in both ex-vivo and in vivo models. These compounds also exhibit anti-proliferative effects, and, as such, may be used as agents to treat hyperproliferation disorders, including cancer.

Families of small molecule IgE inhibitors are defined by the following supragenera, including Supragenus A (Genus A1-A5), Supragenus B (Genus B1-B4), Supragenus C (Genus C1-C4) and Supragenus D (Genus D1-D4):

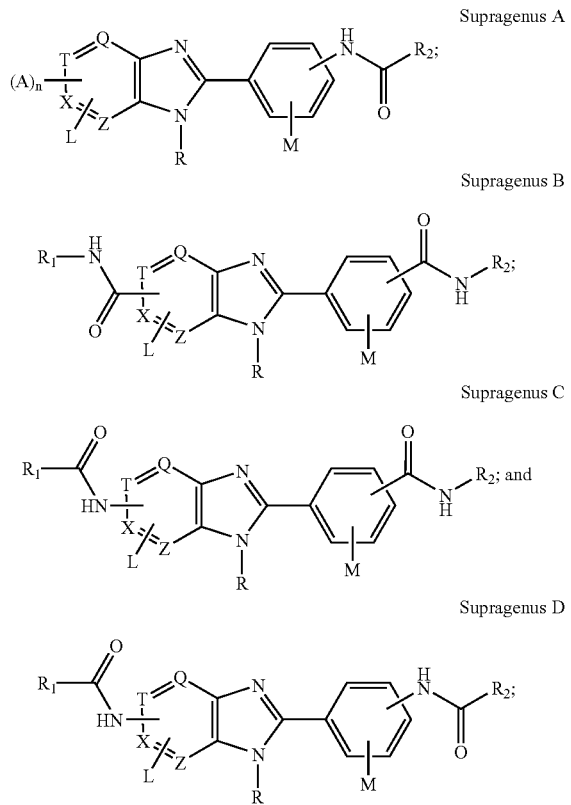

wherein Q, T, X, and Z are independently selected from N or C, and wherein one of Q, T, X, and Z is N;

wherein A is selected from the group consisting of H, halogen, and $CONHR_1$;

wherein n is a number from one to four;

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus A1

One family of small molecule IgE inhibitors is defined by the following genus (Genus A1):

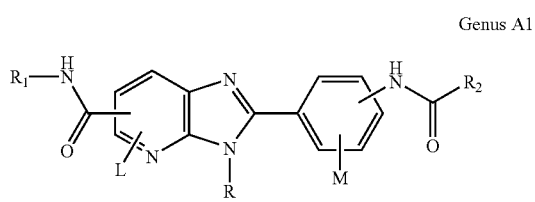

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, OCH$_3$, COOH, COOR'COR', CN, CF$_3$, OCF$_3$, NO$_2$, NR'R', NHCOR' and CONR'R'; and wherein R' is selected from the group consisting of H, alkyl, substituted alkyl, C$_3$-C$_9$ cycloalkyl, substituted C$_3$-C$_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Another subgenus of preferred embodiments comprises any one or more of the following compounds, as shown as Subgenus A1a:

Subgenus A1a

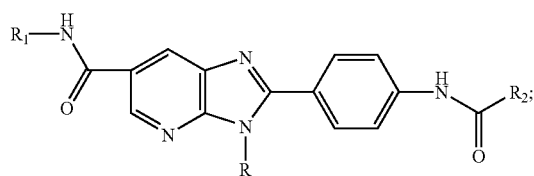

wherein R is selected from the group consisting of H, C$_1$-C$_5$ alkyl, benzyl, p-fluorobenzyl and di-alkylamino alkyl, wherein said C$_1$-C$_5$ alkyl is selected from the group consisting of a straight chain, branched or cyclic alkyl;

wherein R$_1$ and R$_2$ are independently selected from the group consisting of H, alkyl, substituted alkyl, C$_3$-C$_9$ cycloalkyl, substituted C$_3$-C$_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, OCH$_3$, COOH, COOR'COR', CN, CF$_3$, OCF$_3$, NO$_2$, NR'R', NHCOR' and CONR'R'; and wherein R' is selected from the group consisting of H, alkyl, substituted alkyl, C$_3$-C$_9$ cycloalkyl, substituted C$_3$-C$_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus A1 may be synthesized by any conventional reactions known in the art. Examples of syntheses include the following reactions, designated Synthetic Schemes 1 and 2:

Synthetic Scheme 1

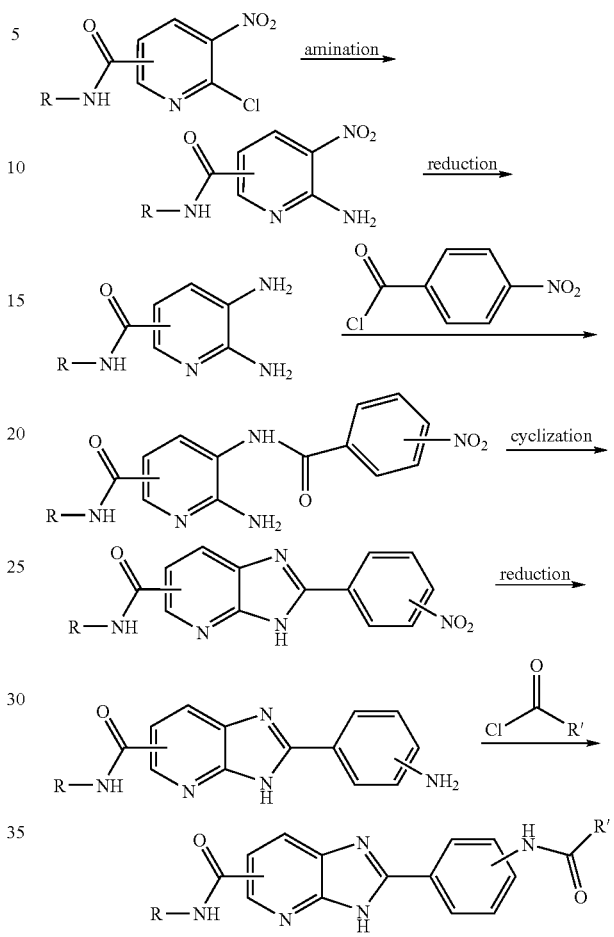

Synthetic Scheme 2

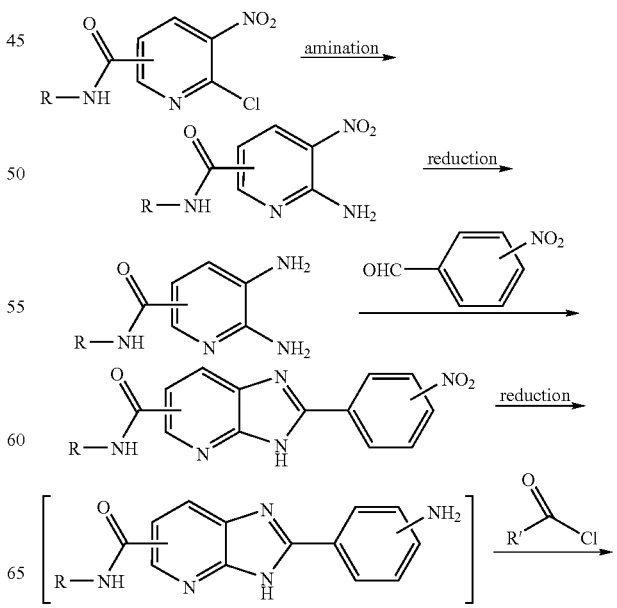

-continued

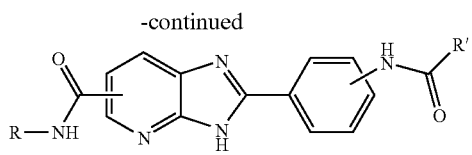

Synthesis of the Compounds of Genus A1

Synthetic Schemes 1 and 2 show methods that can be used to prepare the compounds of Genus A1. One skilled in the art will appreciate that a number of different synthetic reaction schemes may be used to synthesize the compounds of Genus A1. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 1 and 2.

In the processes described herein for the preparation of the compounds of Synthetic Schemes 1 and 2 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 1 and 2 described above are prepared by reacting the appropriate base or acid with a stoichiometric equivalent of the compounds of Synthetic Schemes 1 and 2.

Compounds of Genus A2

One family of small molecule IgE inhibitors is defined by the following genus (Genus A2):

Genus A2

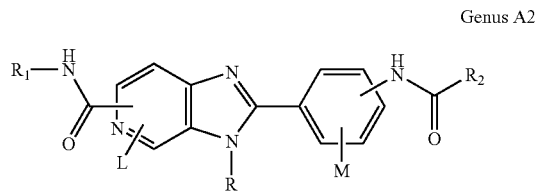

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus A2 may be synthesized by any conventional reactions known in the art. Examples of syntheses include the following reactions, designated Synthetic Schemes 3 and 4:

Synthetic Scheme 3

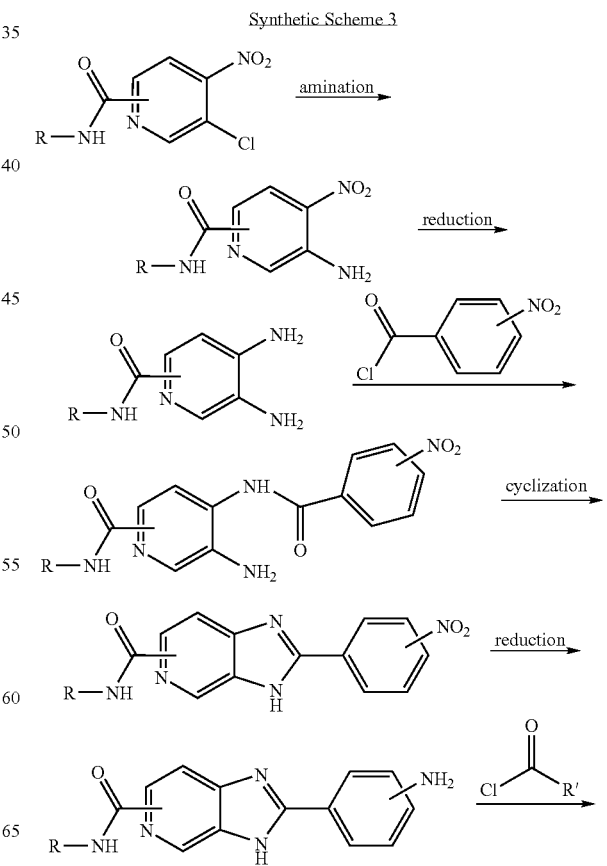

-continued

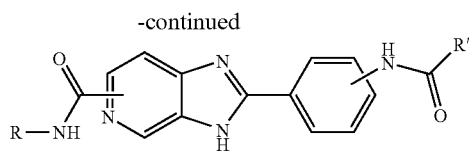

Synthetic Scheme 4

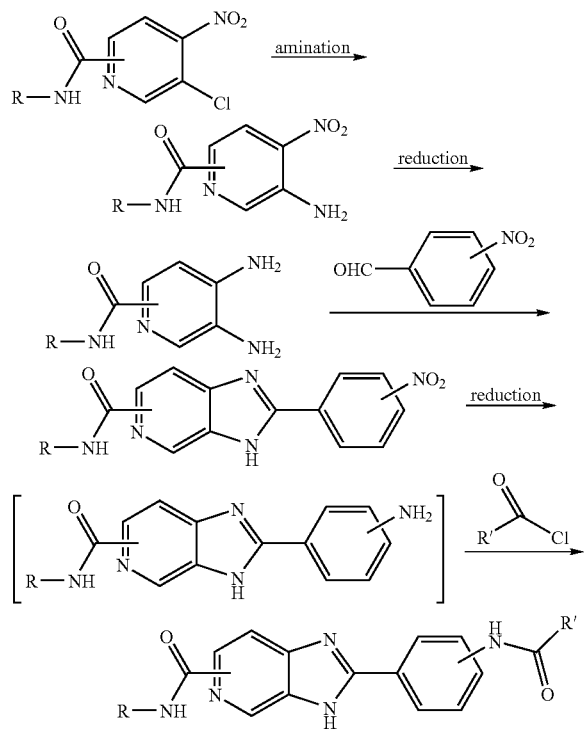

Synthesis of the Compounds of Genus A2

Synthetic Schemes 3 and 4 show methods that can be used to prepare the compounds of Genus A2. One skilled in the art will appreciate that a number of different synthetic reaction schemes may be used to synthesize the compounds of Genus A2. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 3 and 4.

In the processes described herein for the preparation of the compounds of Synthetic Schemes 3 and 4 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 3 and 4 described above are prepared by reacting the appropriate base or acid with a stoichiometric equivalent of the compounds of Synthetic Schemes 3 and 4.

Examples of compounds of Genus A2 are shown below in an array. Preferred compounds can be synthesized according to the above methods.

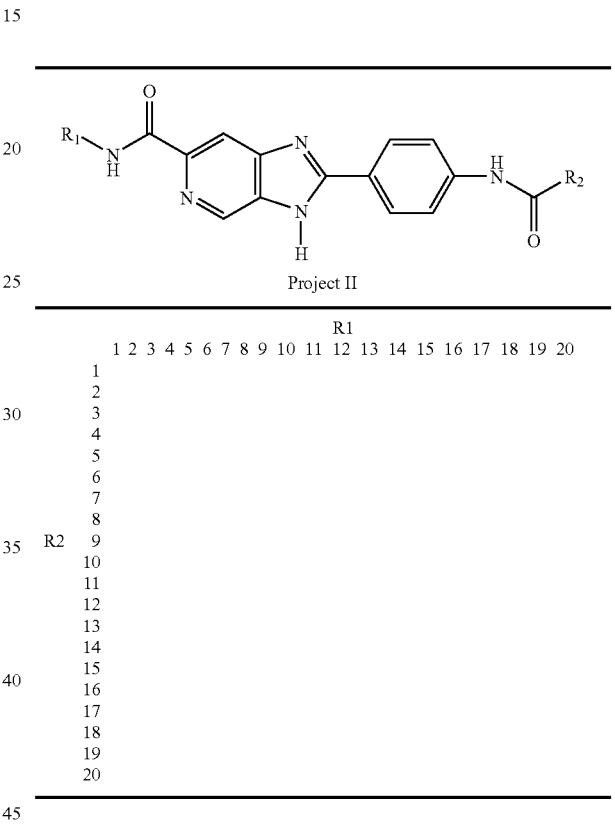

Project II

| | R1 |
| --- | --- |
| | 1 2 3 4 5 6 7 8 9 10 11 12 13 14 15 16 17 18 19 20 |
| R2 | 1 |
| | 2 |
| | 3 |
| | 4 |
| | 5 |
| | 6 |
| | 7 |
| | 8 |
| | 9 |
| | 10 |
| | 11 |
| | 12 |
| | 13 |
| | 14 |
| | 15 |
| | 16 |
| | 17 |
| | 18 |
| | 19 |
| | 20 |

A family of compounds can be made with the formula shown in Project II. The substituents $R_1$ and $R_2$ can be chosen from Substituents 1-20, as shown below.

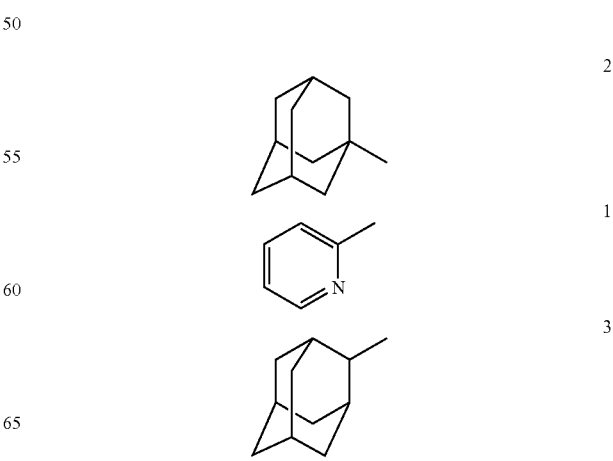

-continued

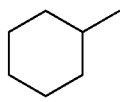

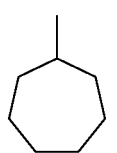

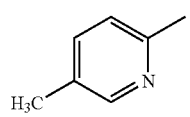

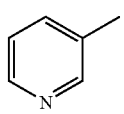

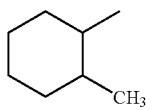

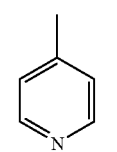

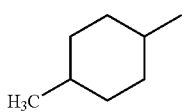

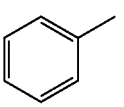

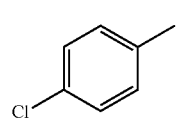

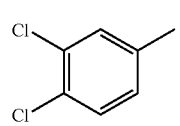

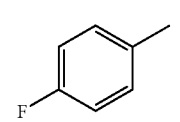

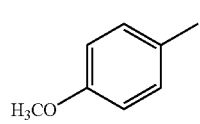

-continued

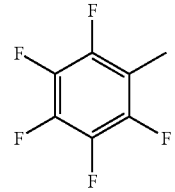

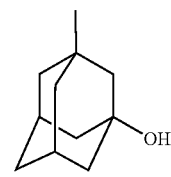

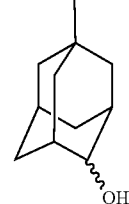

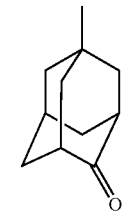

Compounds of Genus A3

One family of small molecule IgE inhibitors is defined by the following genus (Genus A3):

Genus A3

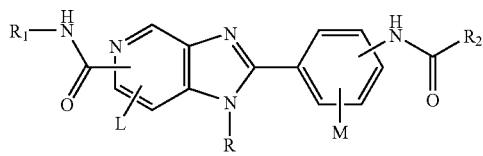

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, OCH$_3$, COOH, COOR'COR', CN, CF$_3$, OCF$_3$, NO$_2$, NR'R', NHCOR' and CONR'R'; and wherein R' is selected from the group consisting of H, alkyl, substituted alkyl, C$_3$-C$_9$ cycloalkyl, substituted C$_3$-C$_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus A3 may be synthesized by any conventional reactions known in the art. Examples of syntheses include the following reactions, designated Synthetic Schemes 5 and 6:

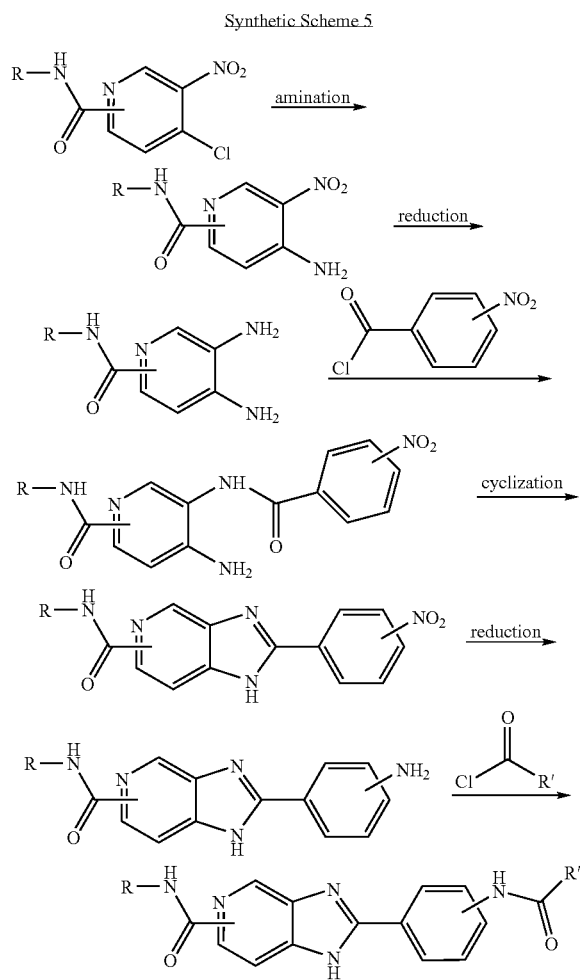

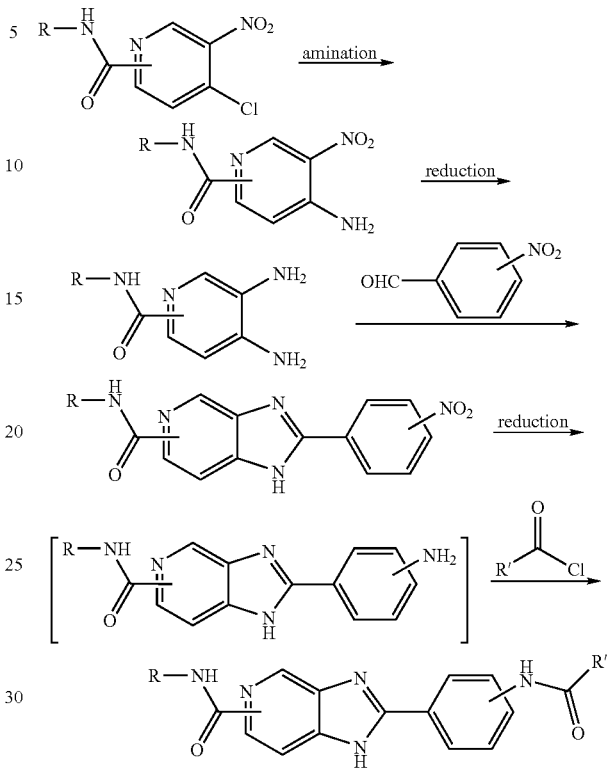

Synthesis of the Compounds of Genus A3

Synthetic Schemes 5 and 6 show methods that can be used to prepare the compounds of Genus A3. One skilled in the art will appreciate that a number of different synthetic reaction schemes may be used to synthesize the compounds of Genus A3. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 5 and 6.

In the processes described herein for the preparation of the compounds of Synthetic Schemes 5 and 6 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 5 and 6 described above are prepared by reacting the appropriate base or acid with a stoichiometric equivalent of the compounds of Synthetic Schemes 5 and 6.

Compounds of Genus A4

One family of small molecule IgE inhibitors is defined by the following genus (Genus A4):

Genus A4

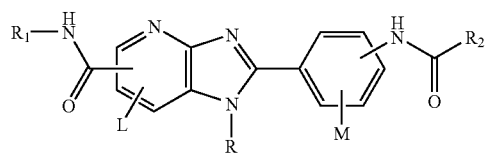

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus A4 may be synthesized by any conventional reactions known in the art. Examples of syntheses include the following reactions, designated Synthetic Schemes 7 and 8:

Synthetic Scheme 7

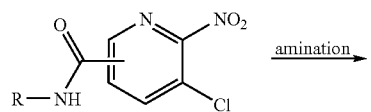

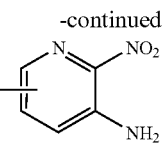

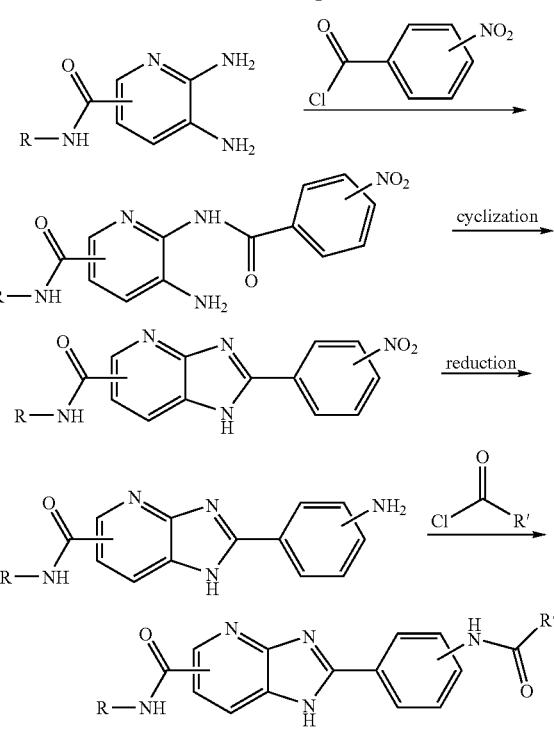

Synthetic Scheme 8

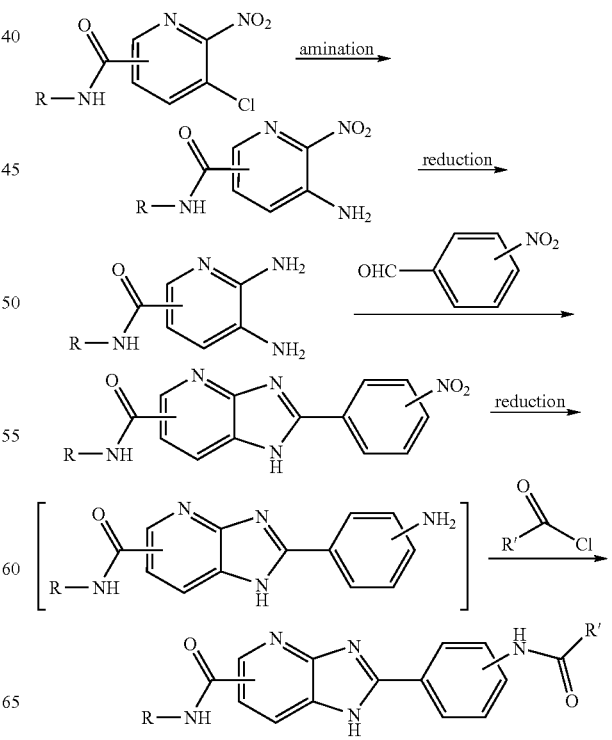

Synthesis of the Compounds of Genus A4

Synthetic Schemes 7 and 8 show methods that can be used to prepare the compounds of Genus A4. One skilled in the art will appreciate that a number of different synthetic reaction schemes may be used to synthesize the compounds of Genus A4. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 7 and 8.

In the processes described herein for the preparation of the compounds of Synthetic Schemes 7 and 8 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 7 and 8 described above are prepared by reacting the appropriate base or acid with a stoichiometric equivalent of the compounds of Synthetic Schemes 7 and 8.

Compounds of Genus A5

One family of small molecule IgE inhibitors is defined by the following genus (Genus A5):

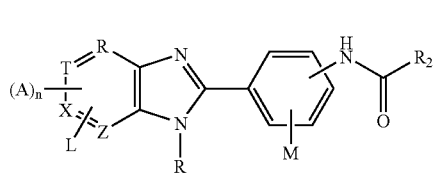

Genus A5 wherein Q, T, X, and Z are independently selected from N or C, and wherein one of Q, T, X, and Z is N;

wherein A is selected from the group consisting of H and halogen;

wherein n is a number from one to four;

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus A5 may be synthesized by any conventional reactions known in the art. Examples of syntheses include the following reactions, designated Synthetic Schemes 9 and 10:

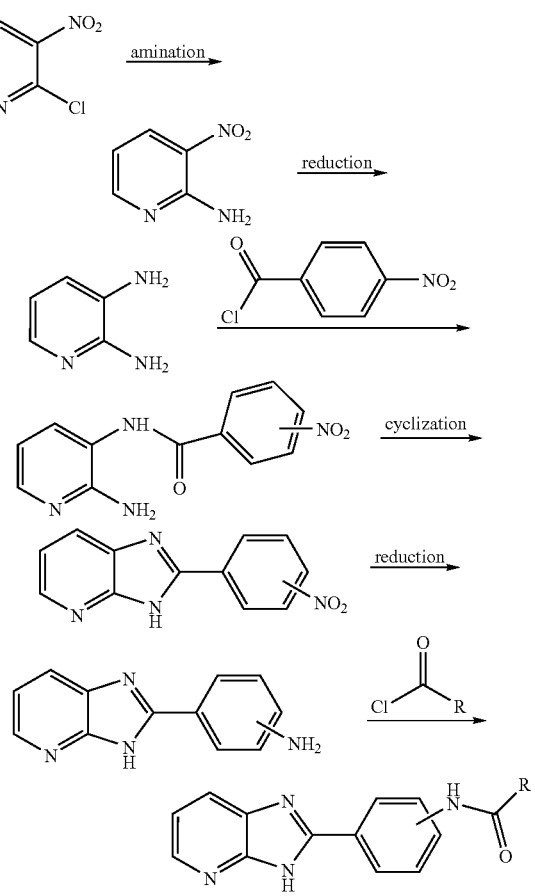

Synthetic Scheme 9

Synthetic Scheme 10

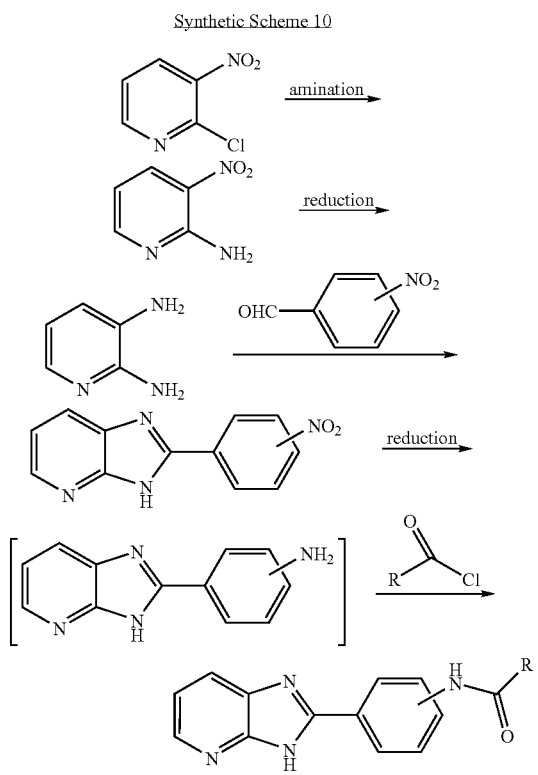

Synthesis of the Compounds of Genus A5

Synthetic Schemes 9 and 10 show methods that can be used to prepare the compounds of Genus A5. One skilled in the art will appreciate that a number of different synthetic reaction schemes may be used to synthesize the compounds of Genus A5. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 9 and 10.

In the processes described herein for the preparation of the compounds of Synthetic Schemes 9 and 10 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 9 and 10 described above are prepared by reacting the appropriate base or acid with a stoichiometric equivalent of the compounds of Synthetic Schemes 9 and 10.

Compounds of Genus B1

One family of small molecule IgE inhibitors is defined by the following genus (Genus B1):

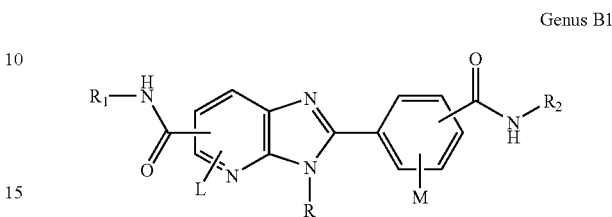

Genus B1 wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Another subgenus of preferred embodiments comprises any one or more of the following compounds, as shown as Subgenus B1a:

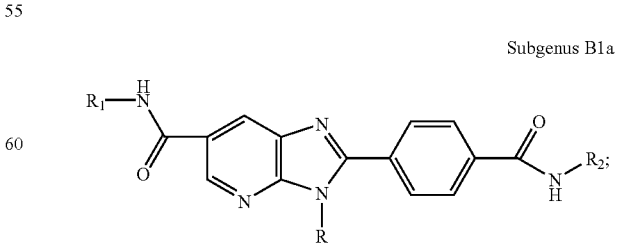

Subgenus B1a wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus B1 may be synthesized by any conventional reactions known in the art. Examples of syntheses include the following reactions, designated Synthetic Schemes 11 and 12:

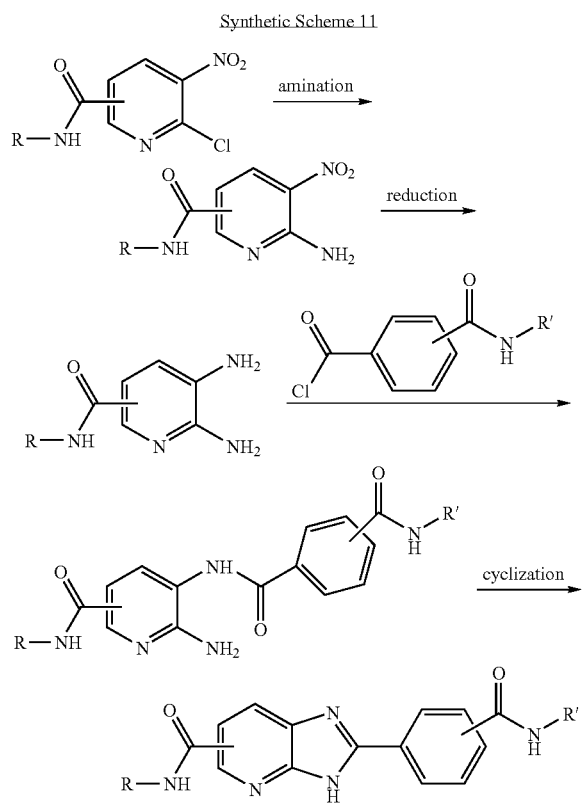

Synthetic Scheme 11

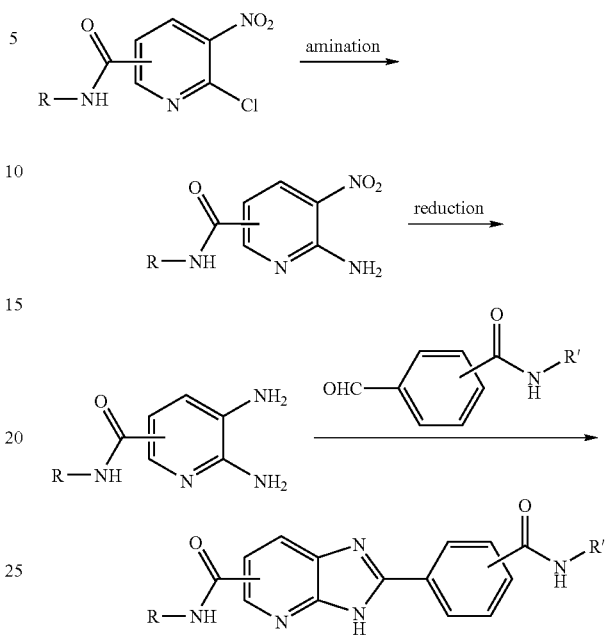

Synthetic Scheme 12

Synthesis of the Compounds of Genus B1

Synthetic Schemes 11 and 12 show methods that can be used to prepare the compounds of Genus B1. One skilled in the art will appreciate that a number of different synthetic reaction schemes may be used to synthesize the compounds of Genus B1. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 11 and 12.

In the processes described herein for the preparation of the compounds of Synthetic Schemes 11 and 12 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 11 and 12 described above are prepared by reacting the appropriate base or acid with a stoichiometric equivalent of the compounds of Synthetic Schemes 11 and 12.

Compounds of Genus B2

One family of small molecule IgE inhibitors is defined by the following genus (Genus B2):

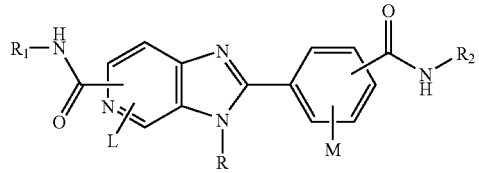

Genus B2 wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus B2 may be synthesized by any conventional reactions known in the art. Examples of syntheses include the following reactions, designated Synthetic Schemes 13 and 14:

Synthetic Scheme 13

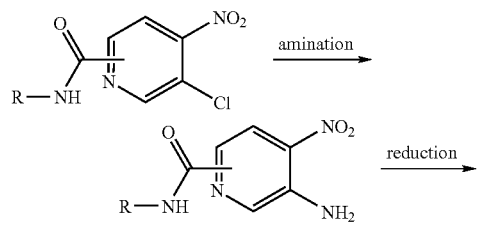

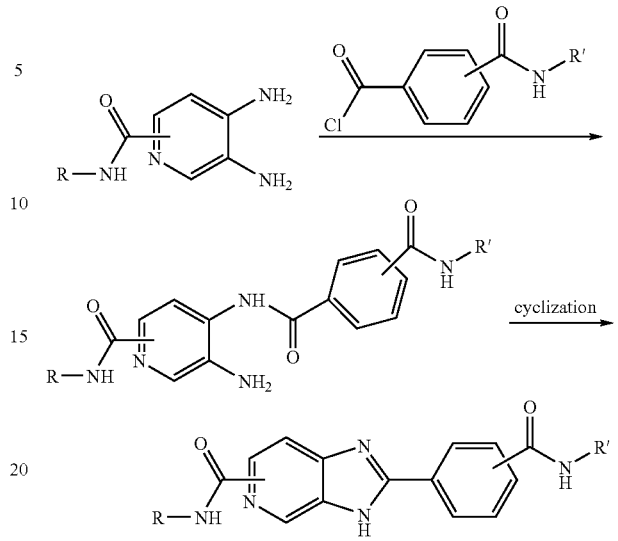

Synthetic Scheme 14

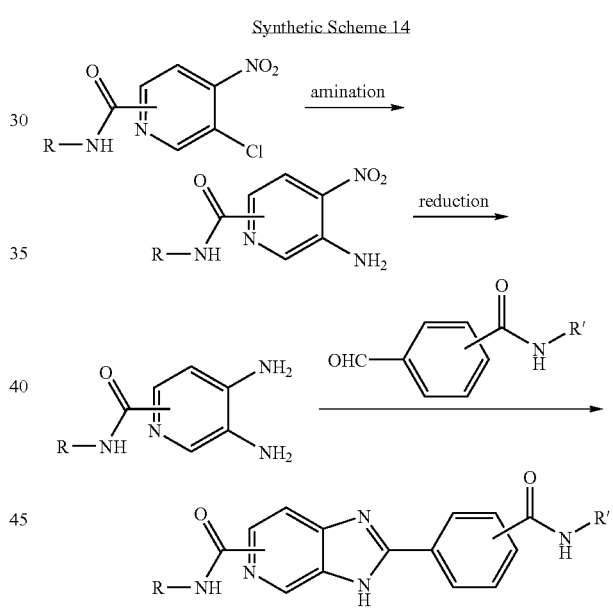

Synthesis of the Compounds of Genus B2

Synthetic Schemes 13 and 14 show methods that can be used to prepare the compounds of Genus B2. One skilled in the art will appreciate that a number of different synthetic reaction schemes may be used to synthesize the compounds of Genus B2. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 13 and 14.

In the processes described herein for the preparation of the compounds of Synthetic Schemes 13 and 14 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 13 and 14 described above are prepared by reacting the appropriate base or acid with a stoichiometric equivalent of the compounds of Synthetic Schemes 13 and 14.

Compounds of Genus B3

One family of small molecule IgE inhibitors is defined by the following genus (Genus B3):

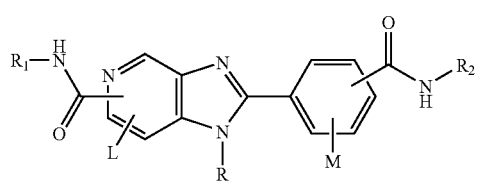

Genus B3 wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus B3 may be synthesized by any conventional reactions known in the art. Examples of syntheses include the following reactions, designated Synthetic Schemes 15 and 16:

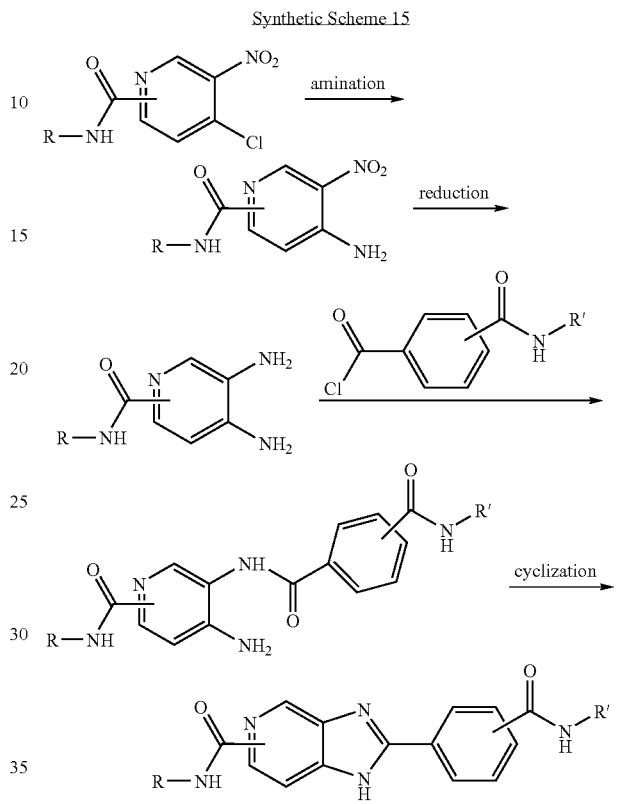

Synthetic Scheme 15

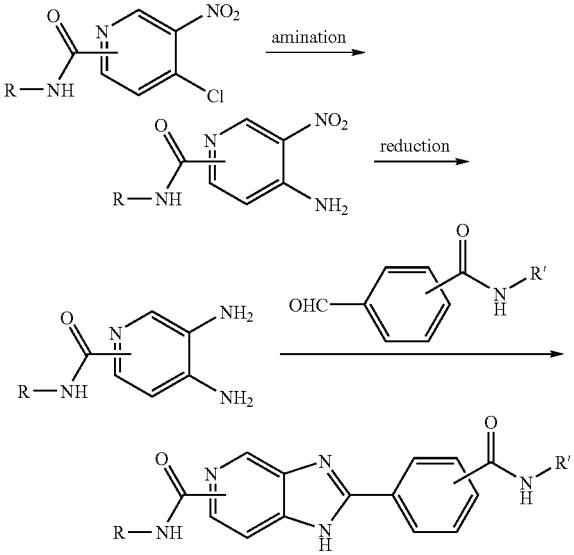

Synthetic Scheme 16

Synthesis of the Compounds of Genus B3

Synthetic Schemes 15 and 16 show methods that can be used to prepare the compounds of Genus B3. One skilled in the art will appreciate that a number of different synthetic reaction schemes may be used to synthesize the compounds of Genus B3. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 15 and 16.

In the processes described herein for the preparation of the compounds of Synthetic Schemes 15 and 16 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 15 and 16 described above are prepared by reacting the appropriate base or acid with a stoichiometric equivalent of the compounds of Synthetic Schemes 15 and 16.

Compound Genus B4

One family of small molecule IgE inhibitors is defined by the following genus (Genus B4):

Genus B4

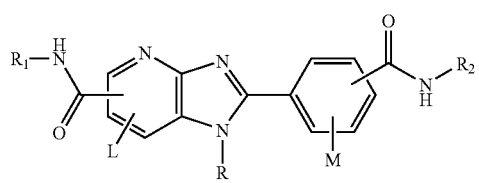

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substituted polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus B4 may be synthesized by any conventional reactions known in the art. Examples of syntheses include the following reactions, designated Synthetic Schemes 17 and 18:

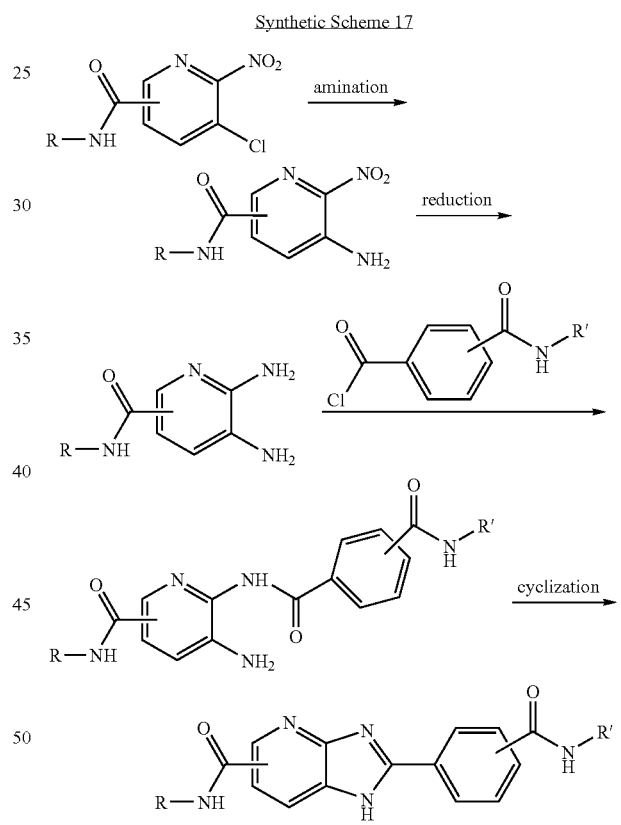

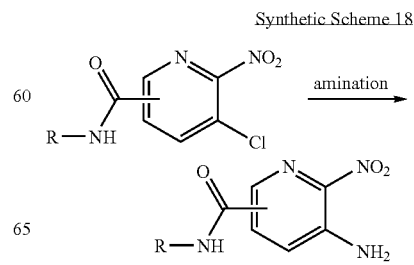

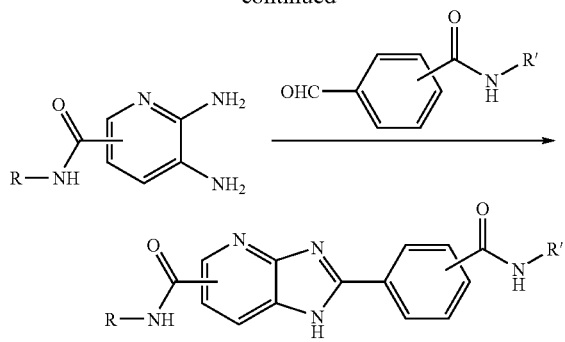

Synthesis of the Compounds of Genus B4

Synthetic Schemes 17 and 18 show methods that can be used to prepare the compounds of Genus B4. One skilled in the art will appreciate that a number of different synthetic reaction schemes may be used to synthesize the compounds of Genus B4. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 17 and 18.

In the processes described herein for the preparation of the compounds of Synthetic Schemes 17 and 18 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 17 and 18 described above are prepared by reacting the appropriate base or acid with a stoichiometric equivalent of the compounds of Synthetic Schemes 17 and 18.

Compounds of Genus C1

One family of small molecule IgE inhibitors is defined by the following genus (Genus C1):

Genus C1

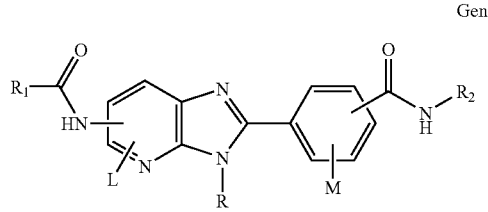

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus C1 may be synthesized by any conventional reactions known in the art. Examples of syntheses include the following reactions, designated Synthetic Schemes 19 and 20:

Synthetic Scheme 19

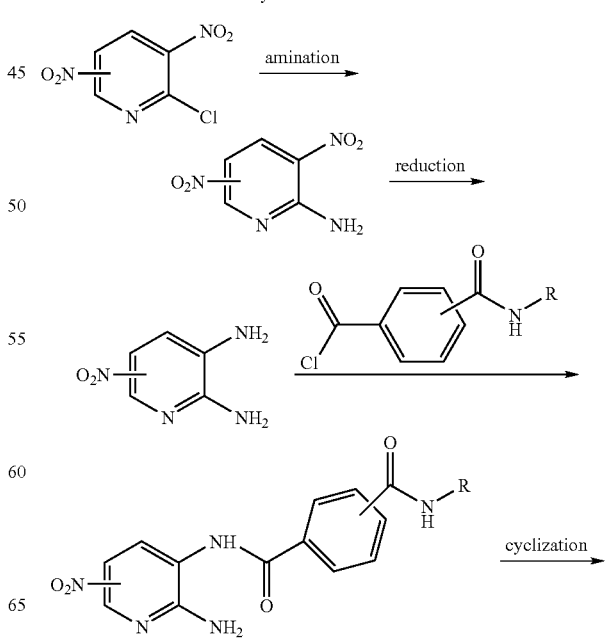

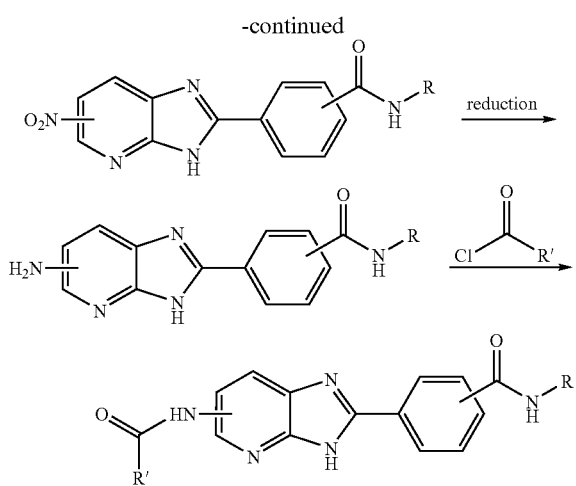

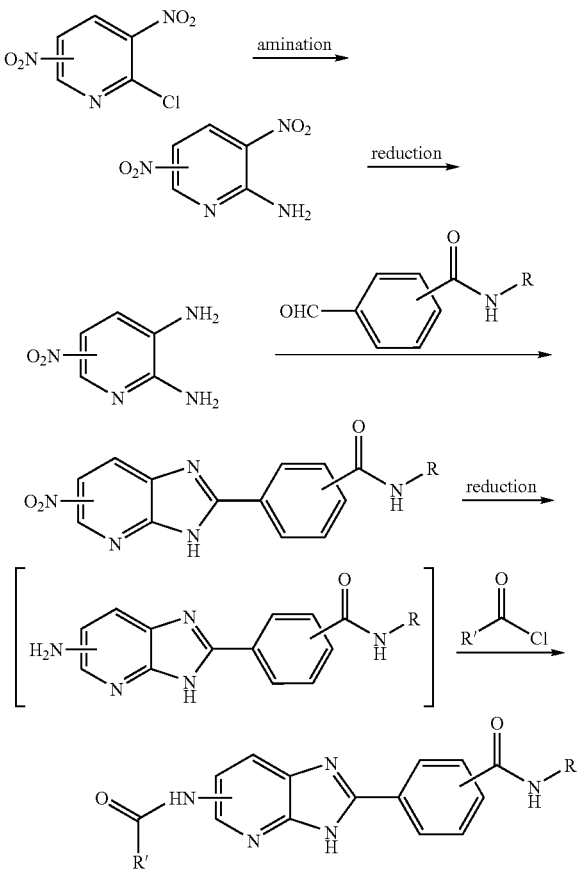

Synthesis of the Compounds of Genus C1

Synthetic Schemes 19 and 20 show methods that can be used to prepare the compounds of Genus C1. One skilled in the art will appreciate that a number of different synthetic reaction schemes may be used to synthesize the compounds of Genus C1. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 19 and 20.

In the processes described herein for the preparation of the compounds of Synthetic Schemes 19 and 20 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 19 and 20 described above are prepared by reacting the appropriate base or acid with a stoichiometric equivalent of the compounds of Synthetic Schemes 19 and 20.

Compounds of Genus C2

One family of small molecule IgE inhibitors is defined by the following genus (Genus C2):

Genus C2

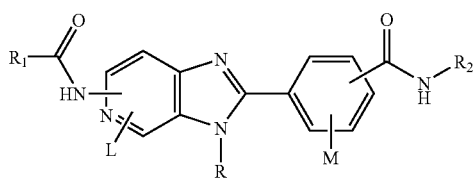

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus C2 may be synthesized by any conventional reactions known in the art. Examples of syntheses include the following reactions, designated Synthetic Schemes 21 and 22:

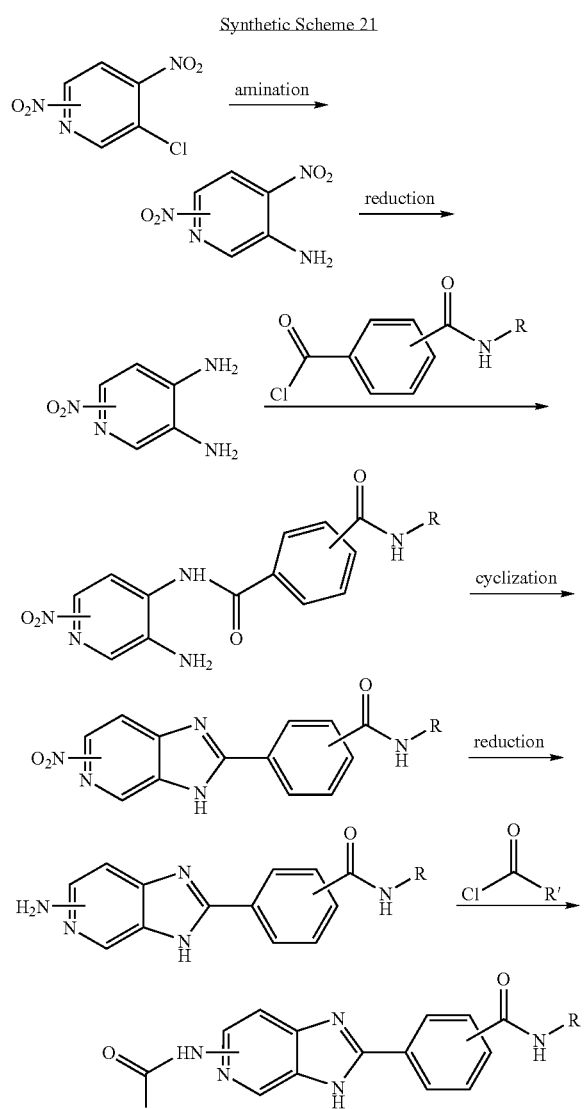

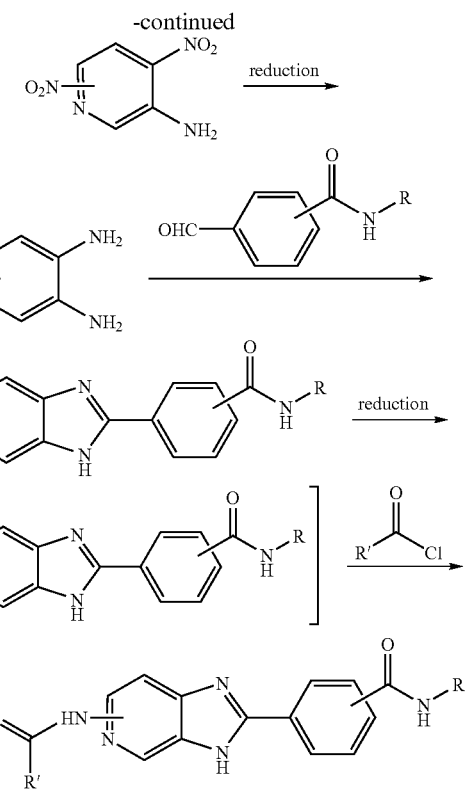

Synthesis of the Compounds of Genus C2

Synthetic Schemes 21 and 22 show methods that can be used to prepare the compounds of Genus C2. One skilled in the art will appreciate that a number of different synthetic reaction schemes may be used to synthesize the compounds of Genus C2. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 21 and 22.

In the processes described herein for the preparation of the compounds of Synthetic Schemes 21 and 22 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 21 and 22 described above are prepared by reacting the appropriate base or acid with a stoichiometric equivalent of the compounds of Synthetic Schemes 21 and 22.

Compounds of Genus C3

One family of small molecule IgE inhibitors is defined by the following genus (Genus C3):

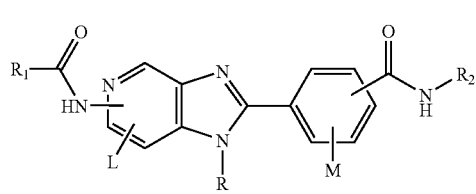

Genus C3 wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus C3 may be synthesized by any conventional reactions known in the art. Examples of syntheses include the following reactions, designated Synthetic Schemes 23 and 24:

Synthetic Scheme 23

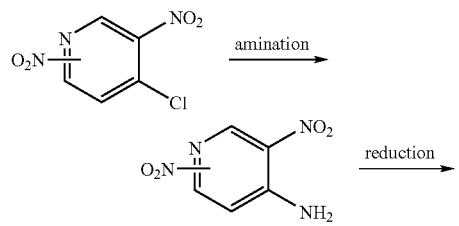

-continued

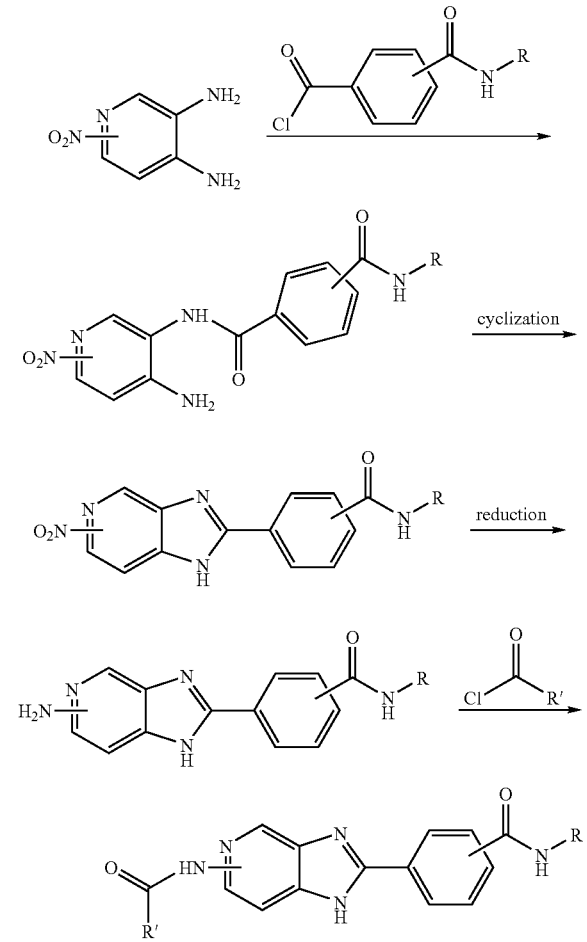

Synthetic Scheme 24

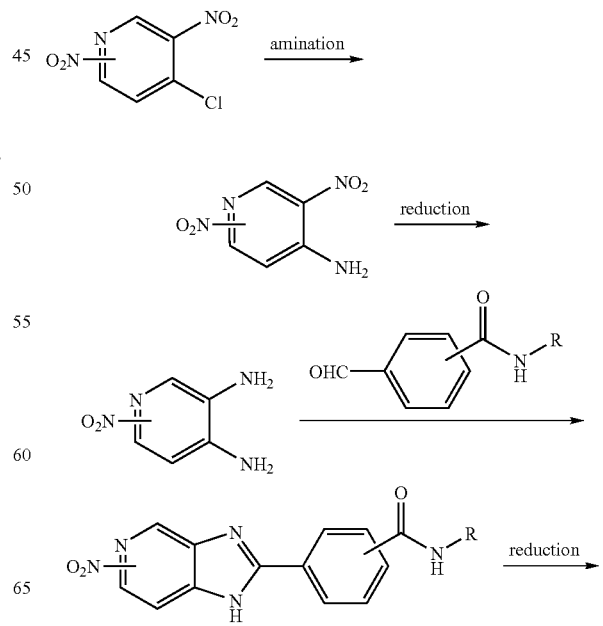

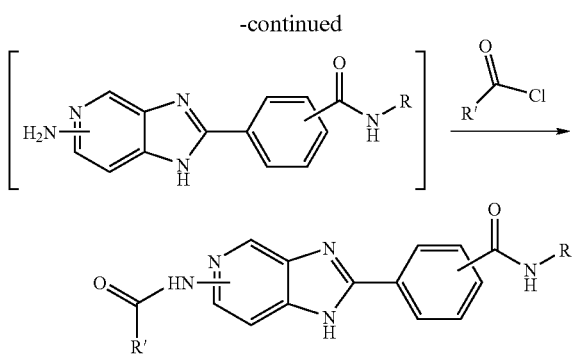

Synthesis of the Compounds of Genus C3

Synthetic Schemes 23 and 24 show methods that can be used to prepare the compounds of Genus C3. One skilled in the art will appreciate that a number of different synthetic reaction schemes may be used to synthesize the compounds of Genus C3. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 23 and 24.

In the processes described herein for the preparation of the compounds of Synthetic Schemes 23 and 24 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 23 and 24 described above are prepared by reacting the appropriate base or acid with a stoichiometric equivalent of the compounds of Synthetic Schemes 23 and 24.

Compounds of Genus C4

One family of small molecule IgE inhibitors is defined by the following genus (Genus C4):

Genus C4

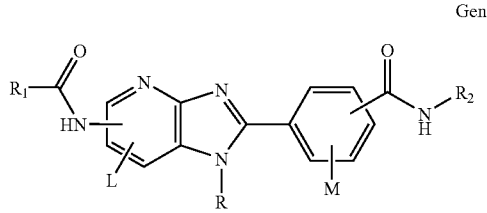

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus C4 may be synthesized by any conventional reactions known in the art. Examples of syntheses include the following reactions, designated Synthetic Schemes 25 and 26:

Synthetic Scheme 25

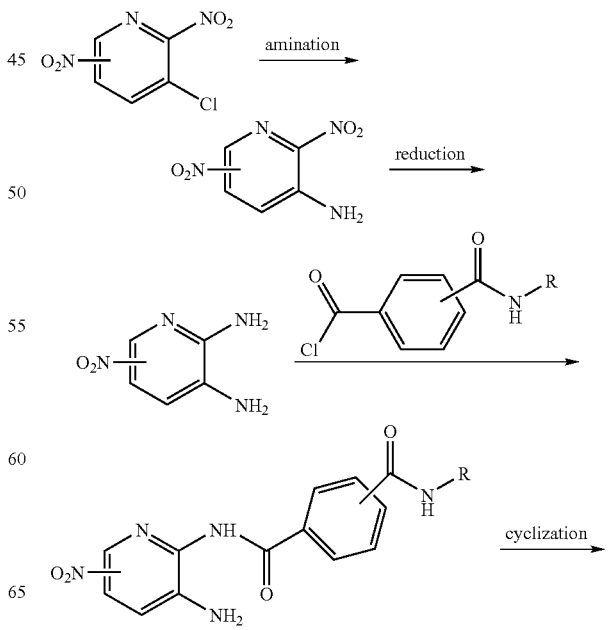

-continued

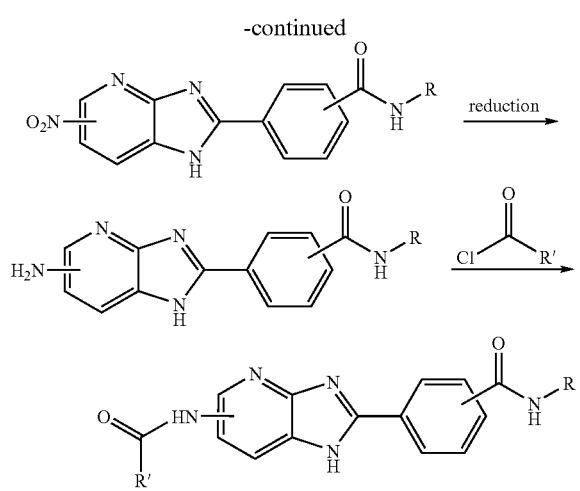

Synthetic Scheme 26

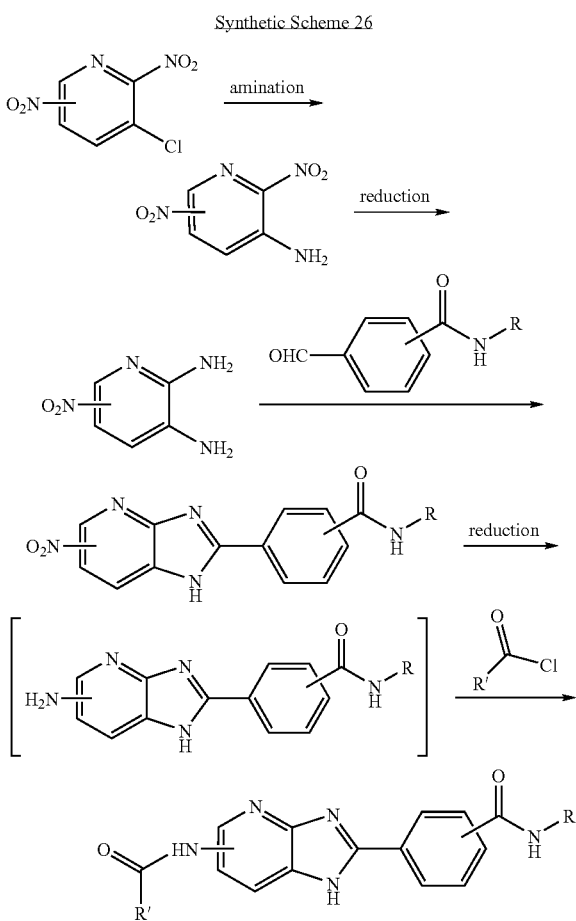

Synthesis of the Compounds of Genus C4

Synthetic Schemes 25 and 26 show methods that can be used to prepare the compounds of Genus C4. One skilled in the art will appreciate that a number of different synthetic reaction schemes may be used to synthesize the compounds of Genus C4. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 25 and 26.

In the processes described herein for the preparation of the compounds of Synthetic Schemes 25 and 26 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 25 and 26 described above are prepared by reacting the appropriate base or acid with a stoichiometric equivalent of the compounds of Synthetic Schemes 25 and 26.

Compounds of Genus D1

One family of small molecule IgE inhibitors is defined by the following genus (Genus D1)

Genus D1

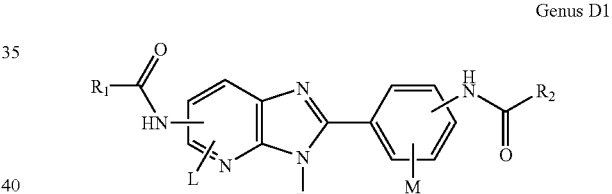

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, C₃-C₉ cycloalkyl, substituted C₃-C₉ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Another subgenus of preferred embodiments comprises any one or more of the following compounds, as shown as Subgenus D1a:

Subgenus D1a

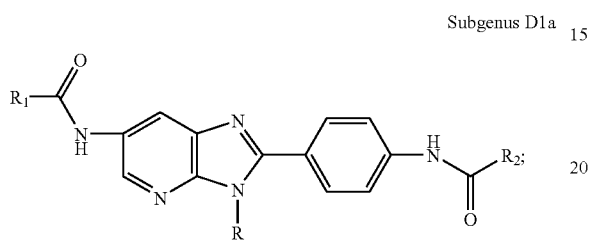

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus D1 may be synthesized by any conventional reactions known in the art. Examples of syntheses include the following reactions, designated Synthetic Schemes 27 and 28:

Synthetic Scheme 27

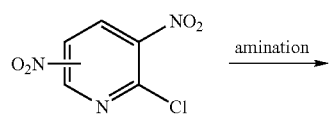

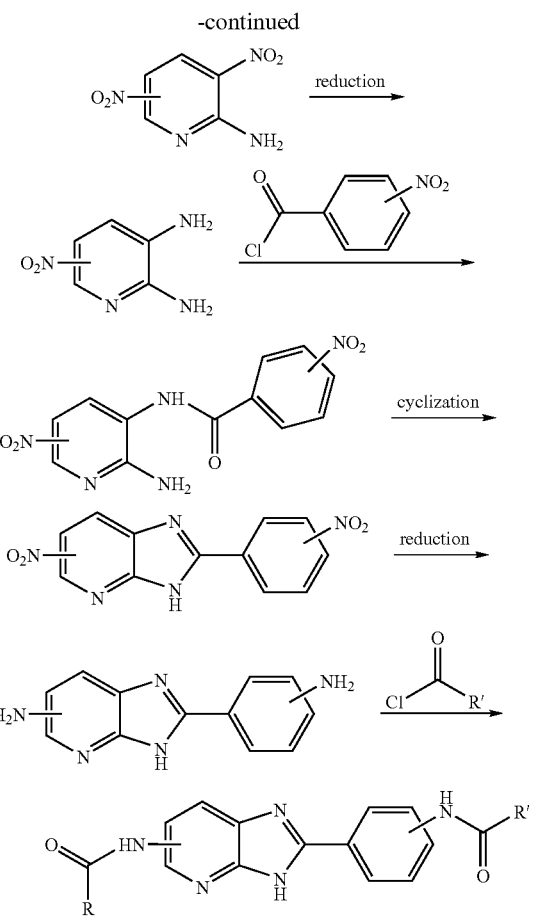

Synthetic Scheme 28

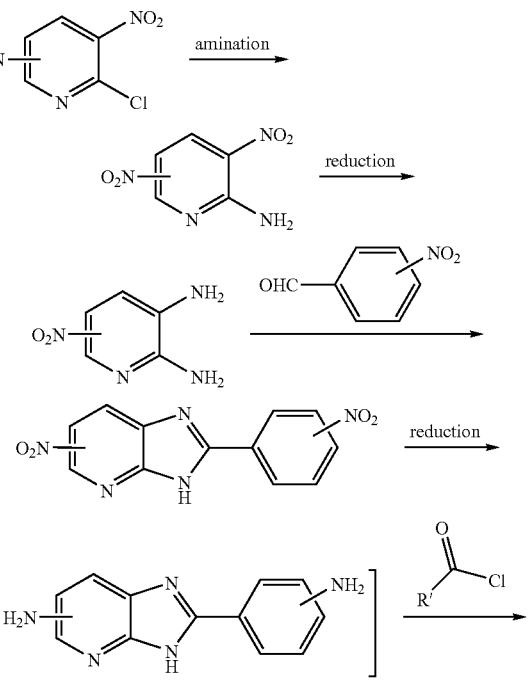

-continued

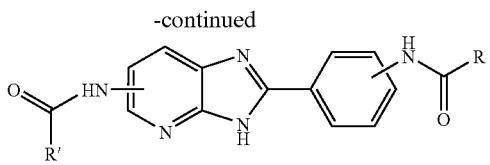

Synthesis of the Compounds of Genus D1

Synthetic Schemes 27 and 28 show methods that can be used to prepare the compounds of Genus D1. One skilled in the art will appreciate that a number of different synthetic reaction schemes may be used to synthesize the compounds of Genus D1. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 27 and 28.

In the processes described herein for the preparation of the compounds of Synthetic Schemes 27 and 28 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 27 and 28 described above are prepared by reacting the appropriate base or acid with a stoichiometric equivalent of the compounds of Synthetic Schemes 27 and 28.

Compounds of Genus D2

One family of small molecule IgE inhibitors is defined by the following genus (Genus D2):

Genus D2

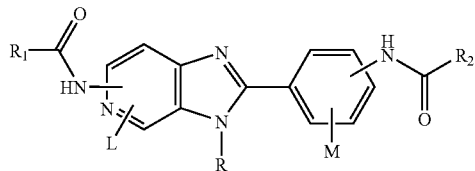

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, $CONHR$ and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

A subgenus of preferred embodiments comprises any one or more of the following compounds, as shown as Subgenus D2a:

Subgenus D2a

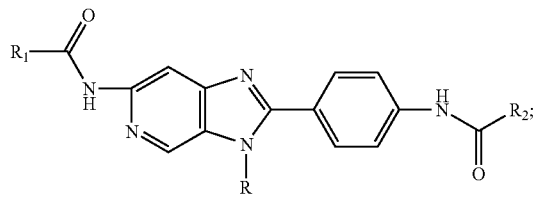

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substituted polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_2$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus D2 may be synthesized by any conventional reactions known in the art. Examples of syntheses include the following reactions, designated Synthetic Schemes 29 and 30:

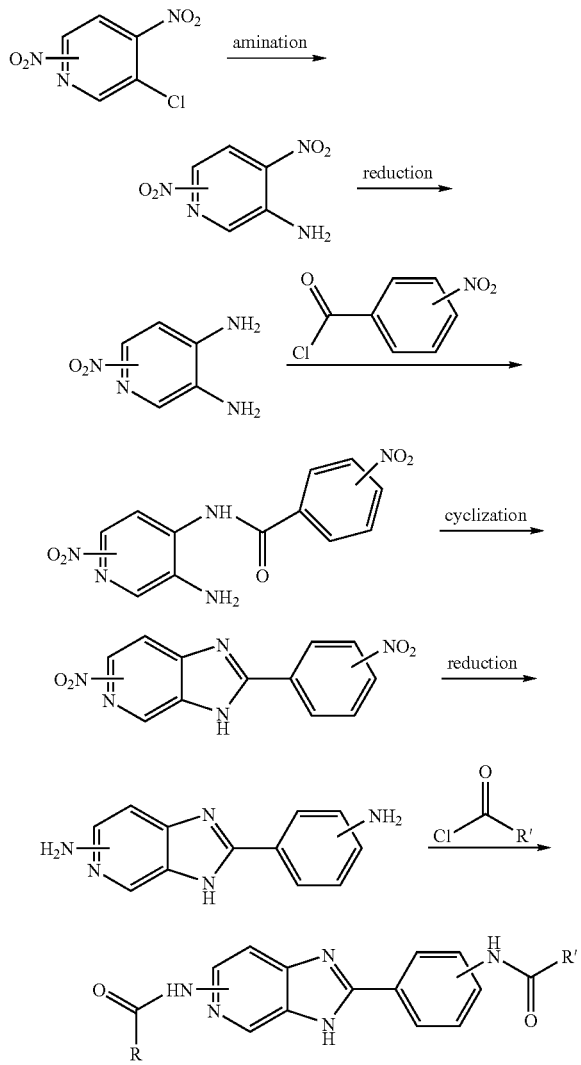

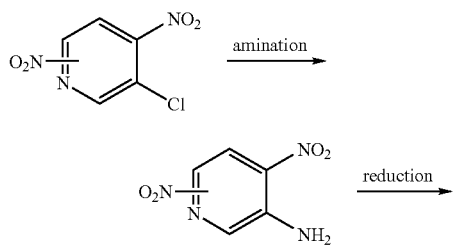

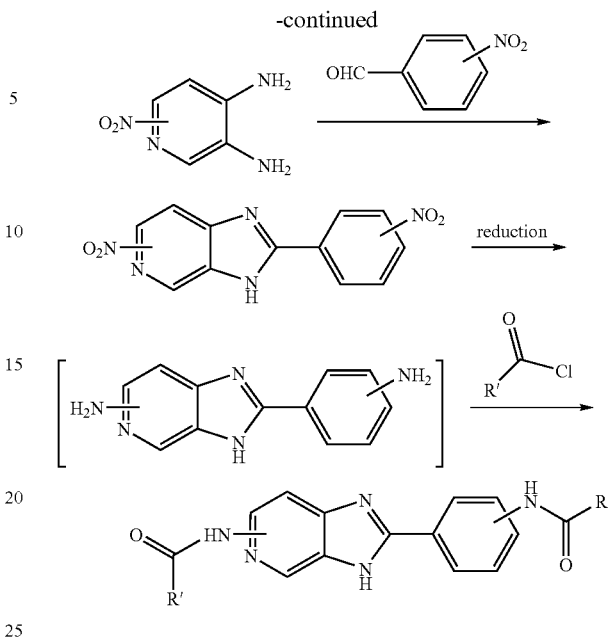

Synthesis of the Compounds of Genus D2

Synthetic Schemes 29 and 30 show methods that can be used to prepare the compounds of Genus D2. One skilled in the art will appreciate that a number of different synthetic reaction schemes may be used to synthesize the compounds of Genus D2. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 29 and 30.

In the processes described herein for the preparation of the compounds of Synthetic Schemes 29 and 30 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 29 and 30 described above are prepared by reacting the appropriate base or acid with a stoichiometric equivalent of the compounds of Synthetic Schemes 29 and 30.

Examples of compounds of Genus D2 are shown below in an array. Preferred compounds can be synthesized according to the above methods.

Project III

[Structure of Project III compound with R₁-C(O)-NH- attached to an imidazopyridine core linked to a phenyl-NH-C(O)-R₂ group]

|    | R1 |    |    |    |    |    |    |    |    |    |    |    |    |    |    |    |    |    |    |    |
|----|----|----|----|----|----|----|----|----|----|----|----|----|----|----|----|----|----|----|----|----|
|    | 1  | 2  | 3  | 4  | 5  | 6  | 7  | 8  | 9  | 10 | 11 | 12 | 13 | 14 | 15 | 16 | 17 | 18 | 19 | 20 |
| 1  |    |    |    |    |    |    |    |    |    |    |    |    |    |    |    |    |    |    |    |    |
| 2  |    |    |    |    |    |    |    |    |    |    |    |    |    |    |    |    |    |    |    |    |
| 3  |    |    |    |    |    |    |    |    |    |    |    |    |    |    |    |    |    |    |    |    |
| 4  |    |    |    |    |    |    |    |    |    |    |    |    |    |    |    |    |    |    |    |    |
| 5  |    |    |    |    |    |    |    |    |    |    |    |    |    |    |    |    |    |    |    |    |
| 6  |    |    |    |    |    |    |    |    |    |    |    |    |    |    |    |    |    |    |    |    |
| 7  |    |    |    |    |    |    |    |    |    |    |    |    |    |    |    |    |    |    |    |    |
| 8  |    |    |    |    |    |    |    |    |    |    |    |    |    |    |    |    |    |    |    |    |
| R2 9 |  |    |    |    |    |    |    |    |    |    |    |    |    |    |    |    |    |    |    |    |
| 10 |    |    |    |    |    |    |    |    |    |    |    |    |    |    |    |    |    |    |    |    |
| 11 |    |    |    |    |    |    |    |    |    |    |    |    |    |    |    |    |    |    |    |    |
| 12 |    |    |    |    |    |    |    |    |    |    |    |    |    |    |    |    |    |    |    |    |
| 13 |    |    |    |    |    |    |    |    |    |    |    |    |    |    |    |    |    |    |    |    |
| 14 |    |    |    |    |    |    |    |    |    |    |    |    |    |    |    |    |    |    |    |    |
| 15 |    |    |    |    |    |    |    |    |    |    |    |    |    |    |    |    |    |    |    |    |
| 16 |    |    |    |    |    |    |    |    |    |    |    |    |    |    |    |    |    |    |    |    |
| 17 |    |    |    |    |    |    |    |    |    |    |    |    |    |    |    |    |    |    |    |    |
| 18 |    |    |    |    |    |    |    |    |    |    |    |    |    |    |    |    |    |    |    |    |
| 19 |    |    |    |    |    |    |    |    |    |    |    |    |    |    |    |    |    |    |    |    |
| 20 |    |    |    |    |    |    |    |    |    |    |    |    |    |    |    |    |    |    |    |    |

A family of compounds can be made with the formula shown in Project III. The substituents $R_1$ and $R_2$ can be chosen from Substituents 1-20, as shown below.

1. [2-pyridyl]
2. [1-adamantyl]
3. [2-adamantyl]
4. [cyclohexyl]
5. [cycloheptyl]
6. [6-methyl-3-pyridyl]
7. [3-pyridyl]
8. [2-methylcyclohexyl]
9. [4-pyridyl]
10. [trans-1,4-dimethylcyclohexyl]
11. [phenyl]
12. [4-chlorophenyl]
13. [3,4-dichlorophenyl]
14. [4-fluorophenyl]
15. [4-methoxyphenyl]
16. [pentafluorophenyl]
17. [norbornyl]
18. [3-hydroxy-1-adamantyl]

-continued

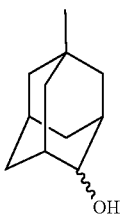

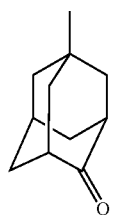

Compounds of Genus D3

One family of small molecule IgE inhibitors is defined by the following genus (Genus D3):

Genus D3

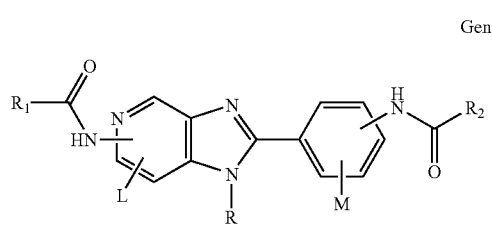

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus D3 may be synthesized by any conventional reactions known in the art. Examples of syntheses include the following reactions, designated Synthetic Schemes 31 and 32:

Synthetic Scheme 31

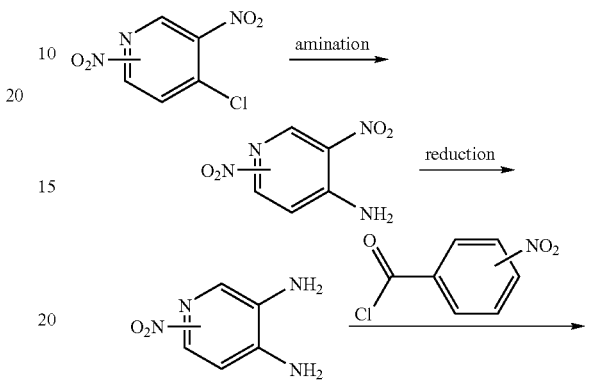

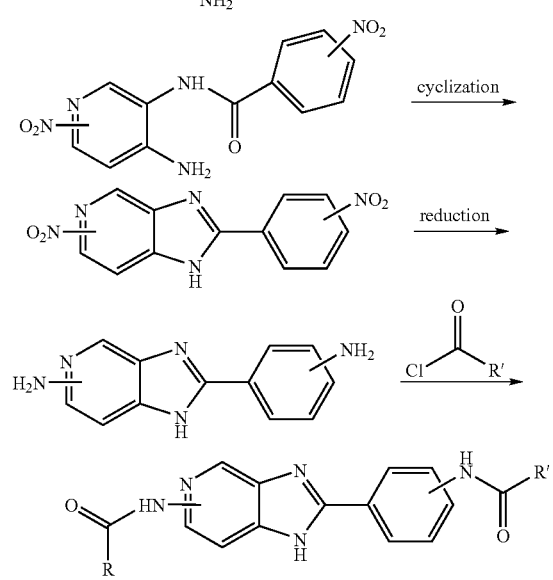

Synthetic Scheme 32

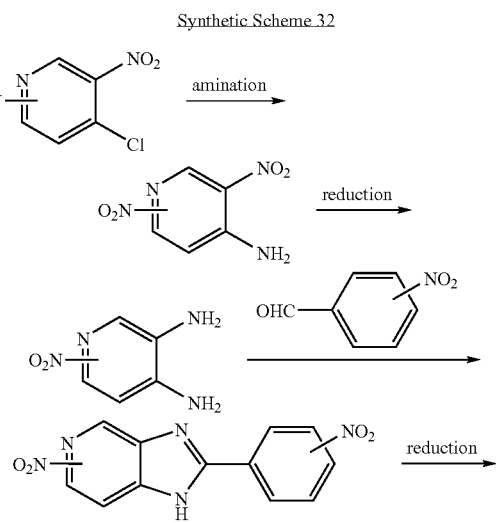

-continued

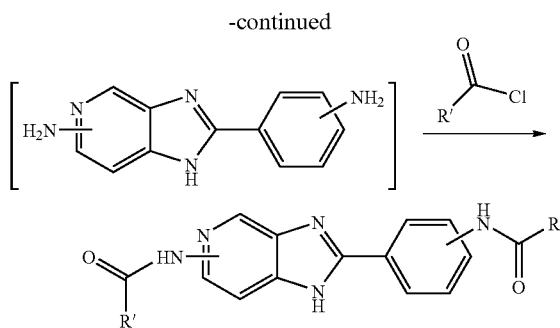

Synthesis of the Compounds of Genus D3

Synthetic Schemes 31 and 32 show methods that can be used to prepare the compounds of Genus D3. One skilled in the art will appreciate that a number of different synthetic reaction schemes may be used to synthesize the compounds of Genus D3. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 31 and 32.

In the processes described herein for the preparation of the compounds of Synthetic Schemes 31 and 32 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 31 and 32 described above are prepared by reacting the appropriate base or acid with a stoichiometric equivalent of the compounds of Synthetic Schemes 31 and 32.

Compounds of Genus D4

One family of small molecule IgE inhibitors is defined by the following genus (Genus D4):

Genus D4

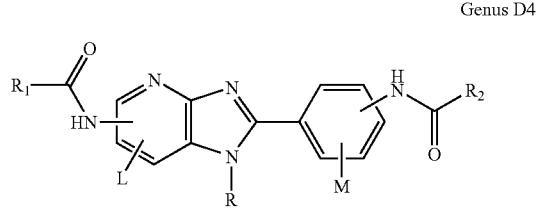

wherein L and M are independently selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein R is selected from the group consisting of H, $C-C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR'COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Another subgenus of preferred embodiments comprises any one or more of the following compounds, as shown as Subgenus D4a:

Subgenus D4a

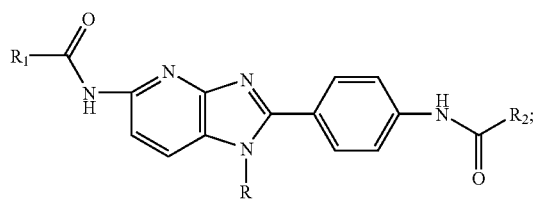

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, OCH$_3$, COOH, COOR'COR', CN, CF$_3$, OCF$_3$, NO$_2$, NR'R', NHCOR' and CONR'R'; and wherein R' is selected from the group consisting of H, alkyl, substituted alkyl, C$_3$-C$_9$ cycloalkyl, substituted C$_3$-C$_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

Compounds of Genus D4 may be synthesized by any conventional reactions known in the art. Examples of syntheses include the following reactions, designated Synthetic Schemes 33 and 34:

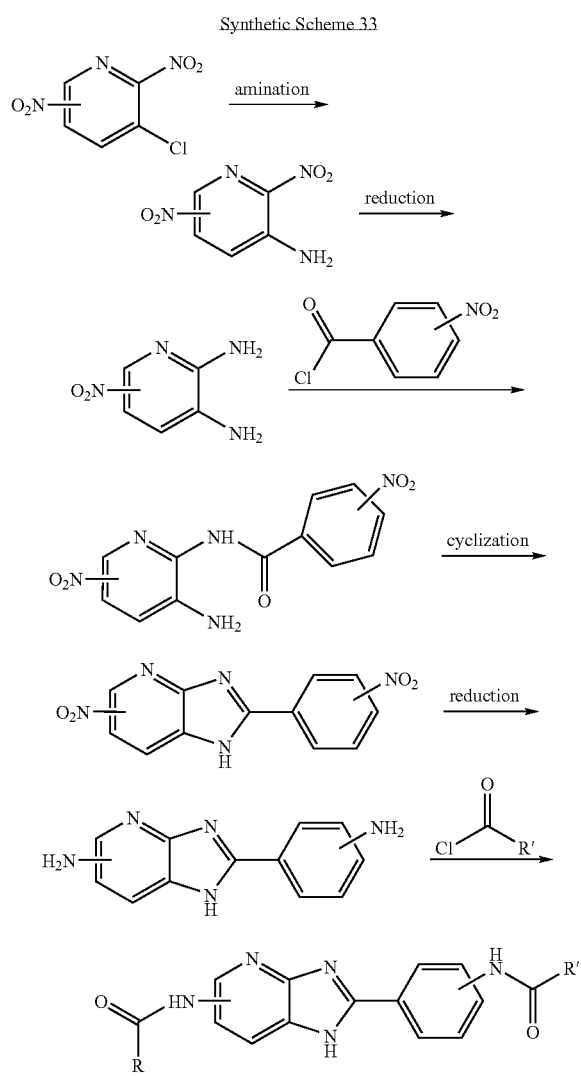

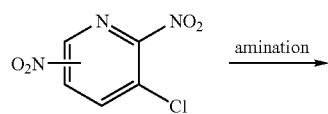

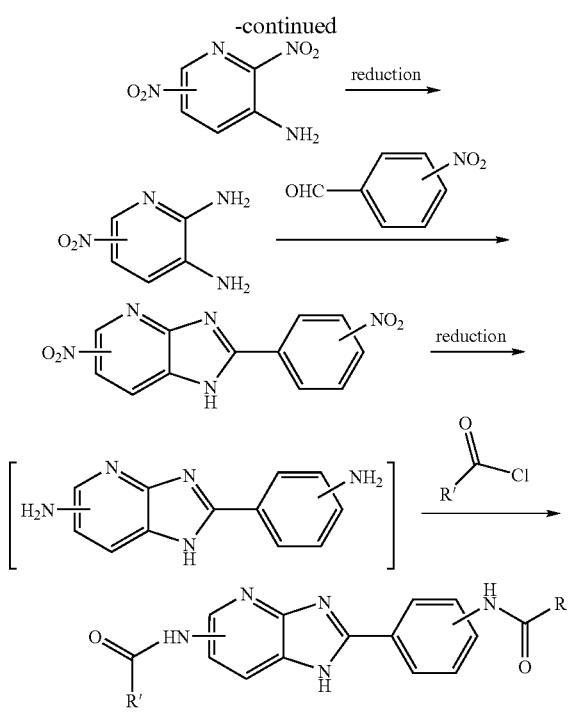

Synthesis of the Compounds of Genus D4

Synthetic Schemes 33 and 34 show methods that can be used to prepare the compounds of Genus D4. One skilled in the art will appreciate that a number of different synthetic reaction schemes may be used to synthesize the compounds of Genus D4. Further, one skilled in the art will understand that a number of different solvents, coupling agents and reaction conditions can be used in the syntheses reactions to yield comparable results.

One skilled in the art will appreciate variations in the sequence and further, will recognize variations in the appropriate reaction conditions from the analogous reactions shown or otherwise known which may be appropriately used in the processes above to make the compounds of Synthetic Schemes 33 and 34.

In the processes described herein for the preparation of the compounds of Synthetic Schemes 33 and 34 of the preferred embodiments, the requirements for protective groups are generally well recognized by one skilled in the art of organic chemistry, and accordingly the use of appropriate protecting groups is necessarily implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1981.

The products of the reactions described herein are isolated by conventional means such as extraction, distillation, chromatography, and the like.

Starting materials not described herein are available commercially, are known, or can be prepared by methods known in the art.

The salts of the compounds of Synthetic Schemes 33 and 34 described above are prepared by reacting the appropriate base or acid with a stoichiometric equivalent of the compounds of Synthetic Schemes 33 and 34.

Preferred embodiments include species in which $R_1$ and $R_2$ are aliphatic groups. In Supragenera A-D, preferred substituents for $R_1$ and $R_2$ are independently selected from the following:

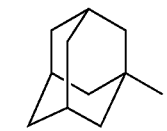
1

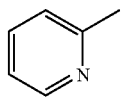
2

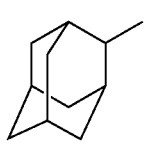
3

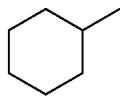
4

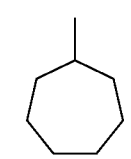
5

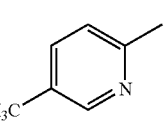
6

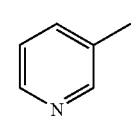
7

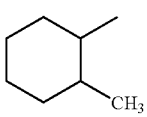
8

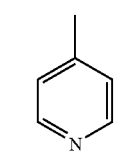
9

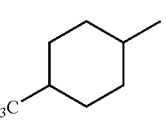
10

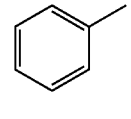
11

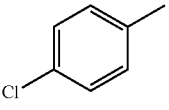
12

-continued

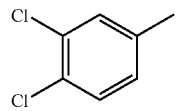
13

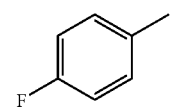
14

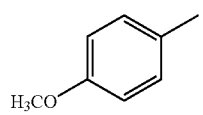
15

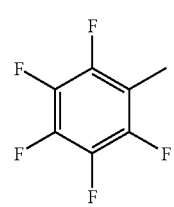
16

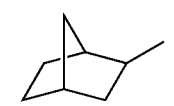
17

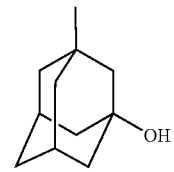
18

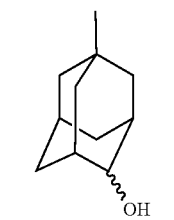
19

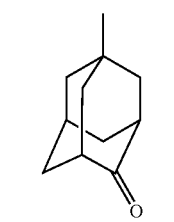
20

More preferably, substituents for $R_1$ and $R_2$ are selected from substituents 1-5 and 13.

The following specific compounds were synthesized and found to be active in in vivo and ex vivo assays. They are encompassed within Supragenera A and D:

S-1
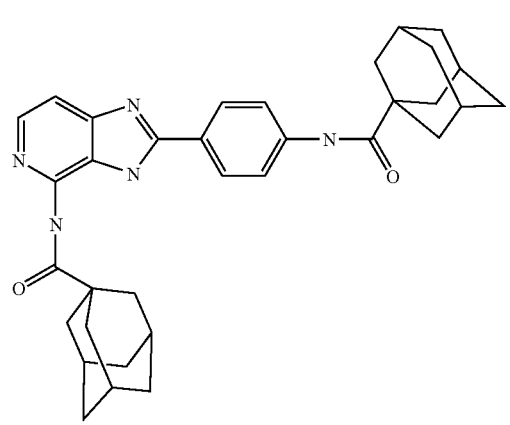
S-2
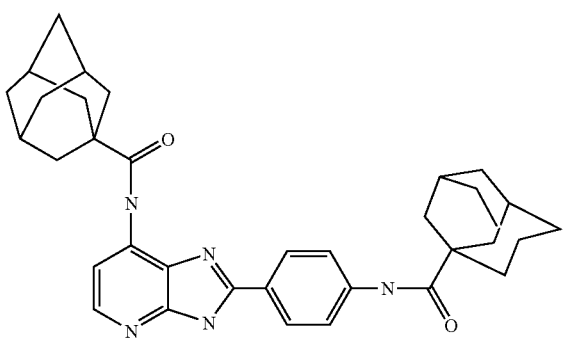
S-3
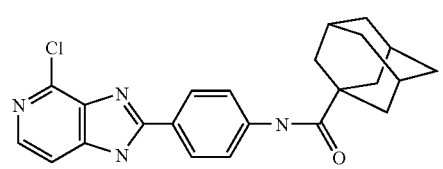
S-4
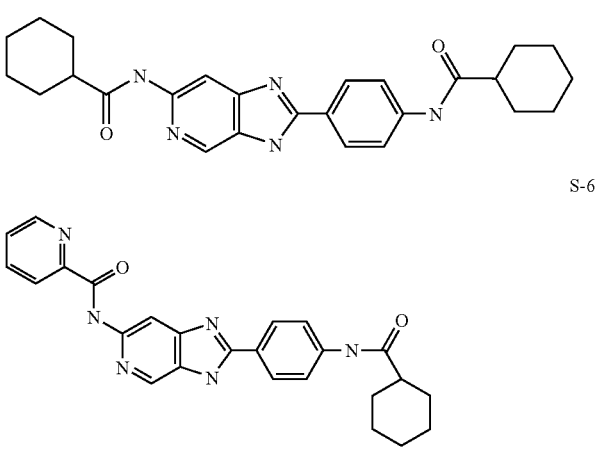
S-5
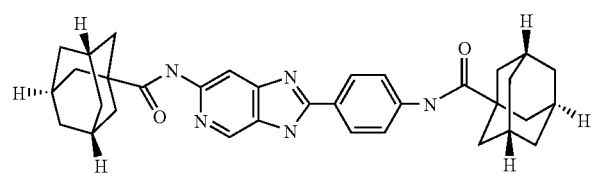
S-6
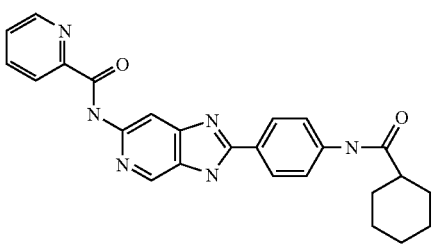
S-7
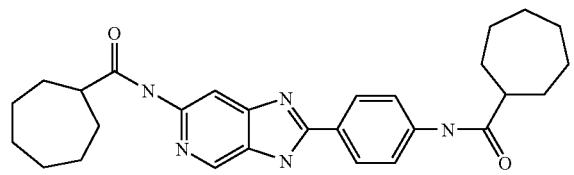
S-8
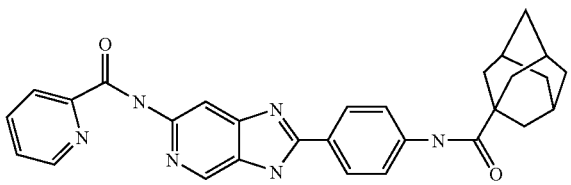
S-9
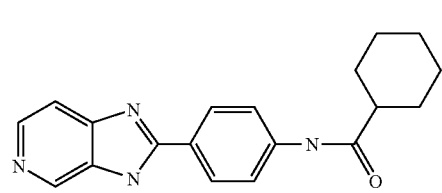
S-10
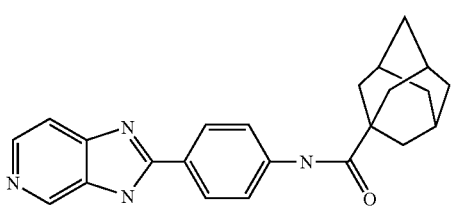
S-11
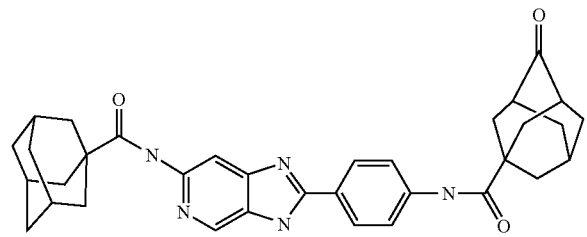
S-12
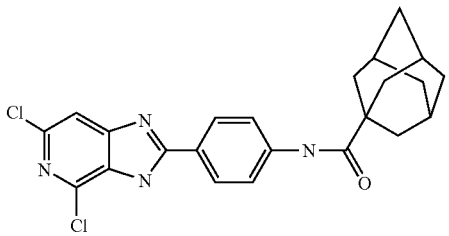

-continued
S-13
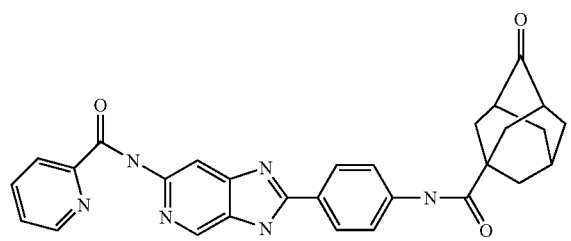
S-14
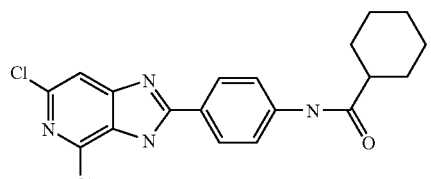
S-15
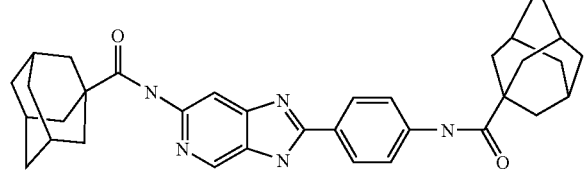
S-16
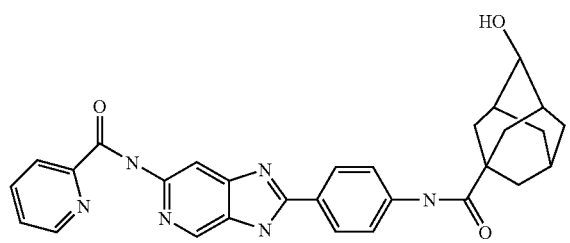
S-17
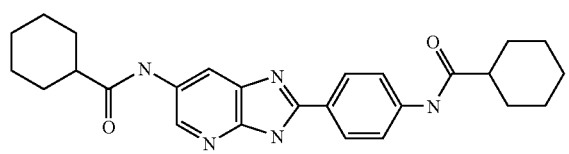
S-18
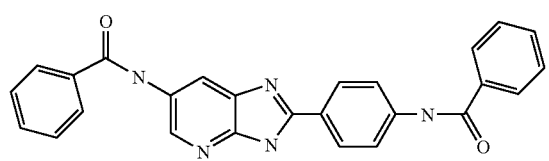
S-19
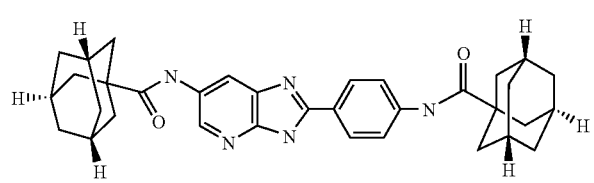
S-20
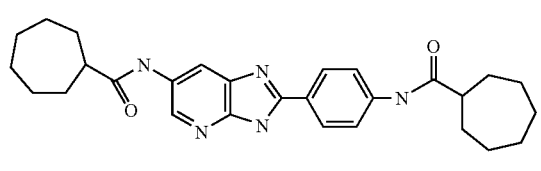
S-21
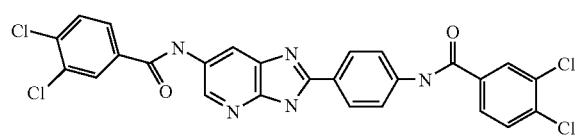
S-22
S-23
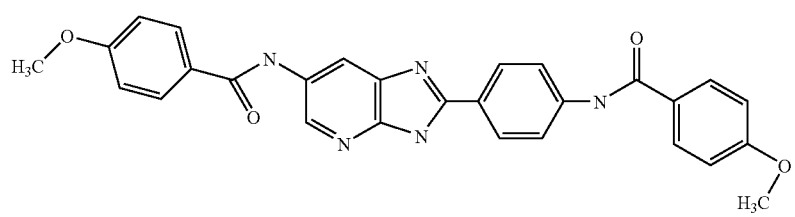
S-24
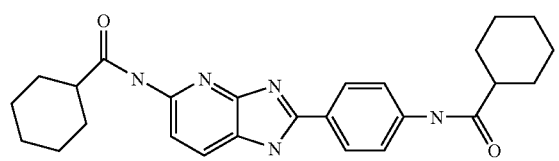
S-25
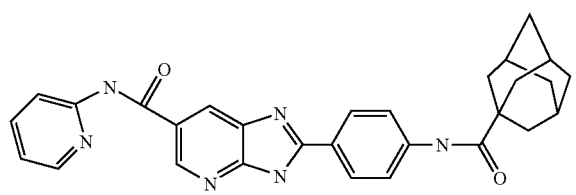

Preferred compounds include S-4 to S-8, S-11, S-13, S-15 to S-17, S-19 to S-21, and S-24 to S-25.

EXAMPLE 1

Synthesis of Preferred Embodiments

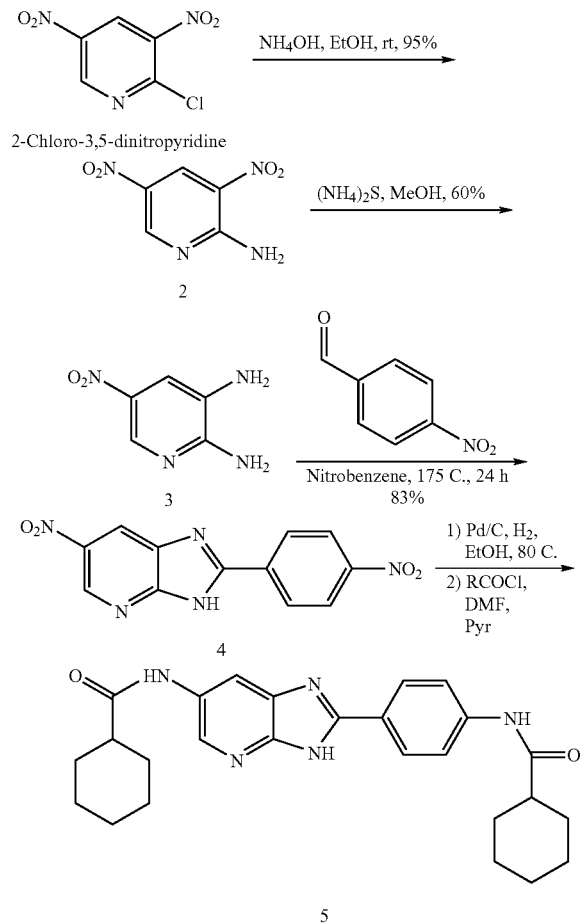

2-Amino-3,5-dinitropyridine (2). 2-Chloro3,5-dinitropyridine (2 g, 9.83 mmol) was suspended in EtOH (15 mL) and NH$_4$OH (28% aq., 6 mL) was added dropwise over 20 minutes with stirring at room temperature. The mixture was stirred for an additional 20 minutes at room temperature and then cooled to 0° C. in an ice bath. The resulting yellow solid was collected by filtration and dried in vacuo at 80° C. to yield 1.745 g (9.5 mmol, 97%) of yellow solid. $^1$H NMR (500 MHz, DMSO-d$_6$) δ 8.69 (br s, 1H), 8.96 (d, J=2.83 Hz, 1H), 9.17 (d, J=2.06 Hz, 1H), 9.26 (br s, 1H). EIMS M$^{+1}$ 185.6.

2,3-Diamino-5-nitropyridine (3). To a stirred suspension of 2-Amino-3,5-dinitropyridine (2) (1.62 g, 8.8 mmol) in MeOH (75 mL) was added an aqueous solution of (NH$_4$)$_2$S (20%, 15 mL, 44 mmol) dropwise at room temperature over 20 minutes. The mixture was stirred for an additional 30 minutes at room temperature and then heated at reflux for 30 minutes. The solution was cooled to room temperature and the solid collected by filtration, rinsed with cold MeOH (2×20 mL), and dried in vacuo at room temperature to give 3 as a red solid (0.812 g, 5.27 mmol, 60%). $^1$H NMR (500 MHz, DMSO-d$_6$) δ 5.31 (s, 2H), 6.98 (s, 2H), 7.35 (d, J=2.55 Hz, 1H), 8.28 (d, J=2.91 Hz, 1H). EIMS M$^{+1}$ 155.1.

6-Nitro-2-(4-nitrophenyl)-3H-imidazo [4,5]pyridine (4). To a stirred solution of 2,3-diamino-5-nitropyridine (3) (400 mg, 2.6 mmol) in nitrobenzene (50 mL) was added 4-nitrobenzaldehyde (393 mg, 2.6 mmol) and the mixture heated at 175° C. for 24 h. The solvent was removed by distillation under reduced pressure and the resulting orange solid collected by filtration using CH$_3$CN. The filter cake was washed with ether and air dried to give 4 as an orange solid (0.614 g, 2.1 mmol, 83%) that was used as is without further purification. $^1$H NMR (500 MHz, DMSO-d$_6$) δ14.58 (br s, 1H), 9.28 (apparent d, 1H), 8.88 (br s, 1H), 8.51 (d, J=8.39 Hz, 2H), 8.45 (d, J=8.28 Hz, 2H). EIMS M$^{-1}$ 284.3. Rf=0.55 (silica, 19:1 DCM/MeOH)

N-[2-(4-Cyclohexylaminophenyl)-3H-imidazo[4,5-b]pyridin-6-yl]cyclohexylamide (5). To a stirred suspension of 6-Nitro-2-(4-nitrophenyl)-3H-imidazo [4,5]pyridine (4) (101 mg, 0.353 mmol) in EtOH (10 mL) in an argon purged flask fitted with a condenser was added Pd/C (10% Pd on carbon, 20 mg) and the apparatus evacuated and purged with H$_2$ gas. The mixture was heated at 80° C. under an atmosphere of H$_2$ for 3 h then filtered warm through a pad of celite. The filtrate was evaporated under reduced pressure to give a green oil (88 mg, 0.35 mmol) that was used as is without analysis due to rapid oxidation. The green oil was dissolved in dry DMF (5 ml) and pyridine (10 eq, 0.3 g, 3.8 mmol, 0.31 mL) and cyclohexanecarbonylchloride (2.2 eq, 0.836 mmol, 122.6 mg, 112 μL) added via syringe and the mixture stirred at room temperature for 15 h. To this solution was added H$_2$O (50 mL) and the mixture stirred for 15 minutes. The resulting solid was collected by filtration and purified by flash chromatography over silica using CH$_2$Cl$_2$/MeOH. Crystallization provided 5 as a white solid (28 mg, 0.063 mmol, 17%) $^1$H NMR (500 MHz, DMSO-d$_6$) δ 13.06 (apparent d, 1H), 10.00 (m, 2H), 8.33 (m, 2H), 8.12 (d, J=8.7 Hz, 2H), 8.06 (d, J=8.7 Hz, 2H), 7.78 (m, 2H), 2.37 (m, 2H), 1.79 (m, 7H), 1.66 (m, 2H), 1.44 (m, 4H), 1.28 (m, 6H). TLC Rf=0.35 (silica, 19:1 DCM/MeOH). EIMS m/z M$^{+1}$ 446.4. Anal. (C$_{26}$H$_{31}$N$_5$O$_2$+0.19CH$_3$OH+0.0002H$_2$O)

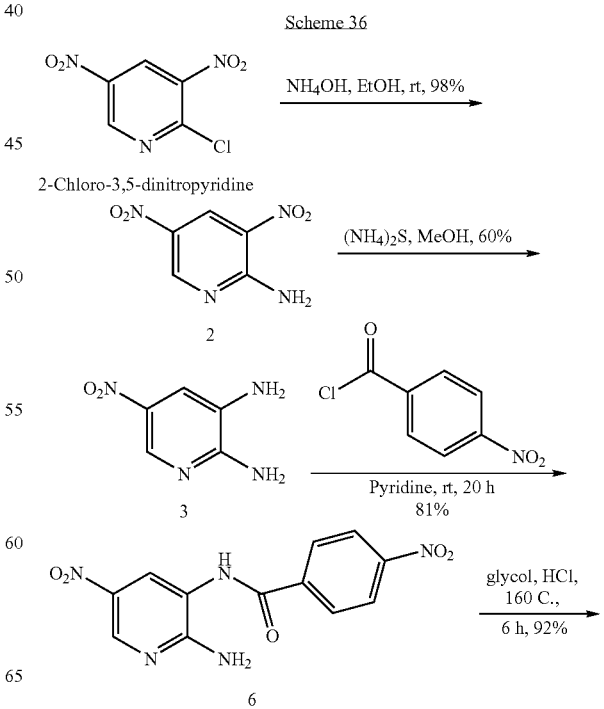

-continued

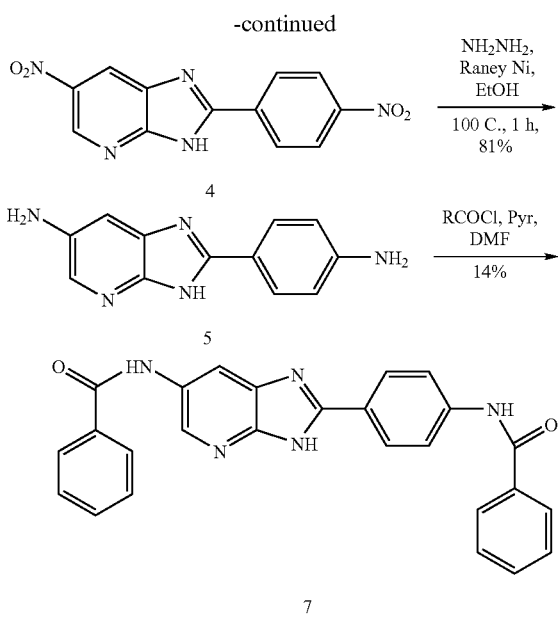

2-Amino-3,5-dinitropyridine (2). 2-Chloro3,5-dinitropyridine (5.38, 26.4 mmol) was suspended in EtOH (75 mL) and NH$_4$OH (28% aq., 30 mL) was added dropwise over 25 minutes with stirring at room temperature. The mixture was stirred for an additional 20 minutes at room temperature and then cooled to 0° C. in an ice bath. The resulting yellow solid was collected by filtration and dried in vacuo at 80° C. to yield 4.42 g (26 mmol, 98%) of yellow solid. $^1$H NMR (500 MHz, DMSO-d$_6$) δ 8.69 (br s, 1H), 8.96 (d, J=2.83 Hz, 1H), 9.17 (d, J=2.06 Hz, 1H), 9.26 (br s, 1H). EIMS M$^{+1}$ 185.6.

2,3-Diamino-5-nitropyridine (3). To a stirred suspension of 2-Amino-3,5-dinitropyridine (2) (2 g, 10.8 mmol) in MeOH (75 mL) was added an aqueous solution of (NH$_4$)$_2$S (20%, 19 mL) dropwise at room temperature over 20 minutes. The mixture was stirred for an additional 30 minutes at room temperature and then heated at reflux for 30 minutes. The solution was cooled to room temperature and the solid collected by filtration, rinsed with cold MeOH (2×20 mL), and dried in vacuo at room temperature to give 3 as a red solid (1.31 g, 8.5 mmol, 79%). $^1$H NMR (500 MHz, DMSO-d$_6$) δ5.31 (s, 2H), 6.98 (s, 2H), 7.35 (d, J=2.55 Hz, 1H), 8.28 (d, J=2.91 Hz, 1H). EIMS M$^{+1}$ 155.1.

N-(2-Amino-5-nitropyridin-3-yl)-4-nitrobenzamide (6). To a solution of 2,3-Diamino-5-nitropyridine (3) in dry pyridine (85 mL) was added 4-nitrobenzoylchloride (0.875 g, 4.7 mmol) and the mixture was stirred at room temperature for 20 h. The mixture was then poured into H$_2$O (250 mL) and stirred for 30 minutes. The resulting yellow solid was collected by filtration and rinsed with H$_2$O until no pyridine remained. The solid was dried in vacuuo at 80 C to give 6 as a yellow solid (1.15 g, 3.8 mmol, 81%). $^1$H NMR (500 MHz, DMSO-d$_6$) δ10.12 (br s, 1H), 8.83 (d, J=2.55 Hz, 1H), 8.84 (d, J=8.5 Hz, 2H), 8.35 (d, J=2.45 Hz, 2H), 8.24 (d, J=8.7 Hz, 2H), 7.62 (br s, 2H). EIMS M$^{-1}$ 302.3.

6-Nitro-2-(4-nitrophenyl)-3H-imidazo [4,5-b]pyridine (4). To a stirred suspension of N-(2-Amino-5-nitropyridin-3-yl)-4-nitrobenzamide (6) (1.15 g, 3.8 mmol) in ethylene glycol (75 mL) was added HCl (Conc., 3 drops) and the mixture heated at 160° C. for 6 h. The solution was cooled to room temperature and poured into H$_2$O (200 mL) and the resulting solid collected by filtration, rinsed with H$_2$O, and dried in vacuo at 80° C. to give 4 as a pale yellow solid (1 g, 3.5 mmol, 92%). $^1$H NMR (500 MHz, DMSO-d$_6$) δ14.58 (br s, 1H), 9.28 (apparent d, 1H), 8.88 (br s, 1H), 8.51 (d, J=8.39 Hz, 2H), 8.45 (d, J=8.28 Hz, 2H). EIMS M$^{-1}$ 284.3. Rf=0.55 (silica, 19:1 DCM/MeOH)

6-Amino-2-(4-Aminophenyl)-3H-imidazo [4,5-b]pyridine (5). To a stirred suspension of 6-Nitro-2-(4-nitrophenyl)-3H-imidazo [4,5-b]pyridine (4) (0.5 g, 1.75 mmol) in EtOH (40 mL) was added Raney Ni° (1 g, slurry in H$_2$O) followed by hydrazine hydrate (2 mL) dropwise over 5 minutes. The reaction mixture was stirred at room temperature until the reaction subsided and was then heated at 100° C. for 1 h. The hot solution was filtered through celite and the filtrate concentrated under reduced pressure. Water was added to the residue resulting in the formation of an off white solid that was collected by filtration, rinsed with H$_2$O and air dried. The solid was then dried in vacuuo at room temperature to give 5 as a light tan solid (0.318 g, 1.4 mmol, 81%) $^1$H NMR (500 MHz, DMSO-d$_6$) δ12.27 (apparent d, 1H), 7.77 (br s, 2H), 7.70 (br s, 1H) 6.97 (br s, 1H), 6.63 (d, J=8.51 Hz, 2H), 5.57 (br s, 2H), 4.97 (br s, 2H)

N-[2-(4-Benzoylamidophenyl)-3H-imidazo[4,5-b]pyridin-6-yl]-benzylamide (7). To a solution of 6-Amino-2-(4-Aminophenyl)-3H-imidazo [4,5-b]pyridine (5) (100 mg, 0.444 mmol) in dry DMF (15 mL) was added pyridine (10 eq, 179 μL) and molecular sieves. Benzoyl Chloride (2.2 eq, 1.0 mmol, 141 mg, 116 μL) was added and the mixture stirred overnight. The mixture was poured into H$_2$O (150 mL) and the solid collected by filtration. The resulting filter cake was dissolved in hot THF (25 mL) and filtered to remove the sieves. The filtrate was concentrated under reduced pressure and the residue crystallized from CH$_2$Cl$_2$/MeOH/THF to give 7 as a white solid (26.8 mg, 0.062 mmol, 14%). $^1$H NMR (500 MHz, DMSO-d$_6$) δ13.22 (apparent d, J=210.95 Hz, 1H), 10.48 (m, 1H), 8.63 (dd, J=15.4 Hz, 1.5 Hz, 1H), 8.47 (apparent d, J=46.47 Hz, 1H), 8.23 (d, J=8.58 Hz, 1H), 8.18 (d, J=8.36 Hz, 1H), 8.00 (m, 6H), 7.60 (m, 6H). EIMS M$^{+1}$ 434.4. Rf=0.50 (silica, 10:1 DCM/MeOH) Anal. C$_{26}$H$_{19}$O$_2$N$_5$+2.734 H$_2$O The following compounds were synthesized in a similar fashion starting with (5):

N-[2-(4-adamantylaminophenyl)-3H-imidazo[4,5-b]pyridin-6-yl]-adamantylamide. A white solid (20 mg, 0.036 mmol, 9%). Mp: 400 C dec. $^1$H NMR (500 MHz, DMSO-d$_6$) δ13.05 (apparent d, 1H), 9.31 (m, 2H), 8.48 (apparent d, 2H), 8.33 (apparent d, 2H), 8.33 (s, 1H), 8.23 (s, 1H), 8.11 (dd, J=8.15 Hz, 23.4 Hz 2H), 7.87(m, 2H), 2.04 (m, 8H), 1.95 (m, 6H), 1.73 (m, 7H). TLC Rf=0.35 (silica, 19:1 DCM/MeOH). EIMS m/z M$^{+1}$ 550.8. Anal. (C$_{34}$H$_{39}$N$_5$O$_2$+1.5H$_2$O+0.2CH$_3$OH)

N-[2-(4-cycloheptylaminophenyl)-3H-imidazo[4,5-b]pyridin-6-yl]-cycloheptylamide. A white solid (100 mg, 0.212 mmol, 48%). Mp: 374 C dec. $^1$H NMR (500 MHz, DMSO-d$_6$) δ13.06 (apparent d, 1H), 9.98 (apparent d, 2H), 8.38 (m, 2H), 8.27 (s, 2H), 8.12 (dd, J=8.3 Hz, 25.8 Hz, 4H), 7.77 (t, 4H), 1.95-1.4 (series of m 22H). TLC Rf=0.35 (silica, 19:1 DCM/MeOH). EIMS m/z M$^{+1}$ 474.6. Anal. (C$_{28}$H$_{35}$N$_5$O$_2$+0.27H$_2$O)

N-[2-(4-(3,4-dichlorophenyl)amino-phenyl)-3H-imidazo[4,5-b]pyridin-6-yl]-3,4-dichloro-benzamide. An off white solid (150 mg, 0.26 mmol, 65%). Mp: 372-374C dec. $^1$H NMR (500 MHz, DMSO-d$_6$) δ13.29 (apparent d, 2H), 10.64 (apparent d, 2H), 8.63 (m, 1H), 8.46 (m, 1H), 8.29 (m, 4H), 8.24 (m, 1H), 8.00 (m 5H), 7.88 (m, 3H), EIMS m/z M$^{-1}$ 571.3. Anal. (C$_{26}$H$_{15}$Cl$_4$N$_5$O$_2$+2.05H$_2$O+0.1 DMF)

N-[2-(4-(4-chlorophenyl)amino-phenyl)-3H-imidazo[4,5-b]pyridin-6-yl]-(4-chlorophenyl)-benzamide. A white solid (42 mg, 0.084 mmol, 19%). Mp: >400C dec. $^1$H NMR (500 MHz, DMSO-d$_6$) δ13.24 (apparent d, 2H), 10.54 (m, 2H), 8.62 (m, 2H), 8.44 (apparent d, 2H), 8.20 (dd, J=8.7 Hz, 24.8 Hz, 4H), 8.02 (m, 6H), 8.03 (d, J=8.45 Hz 4H), EIMS m/z M$^{+1}$ 502.8. Anal. (C$_{26}$H$_{17}$Cl$_2$N$_5$O$_2$+0.385H$_2$O+0.01 DMF)

N-[2-(4-(4-methoxyphenyl)amino-phenyl)-3H-imidazo[4,5-b]pyridin-6-yl]-(4-methoxyphenyl)-benzamide. A white solid (118 mg, 0.24 mmol, 54%). Mp: 332 C dec. $^1$H NMR (500 MHz, DMSO-d$_6$) δ13.17 (apparent d, 2H), 10.30 (apparent d, 4H), 8.61 (d, J=15 Hz, 2H), 8.44 (apparent d, 2H), 8.18 (dd, J=8.25 Hz, 24.65 Hz, 4H), 8.00 (m, 6H), 7.08 (d, 4H), 3.86 (s, 3H), EIMS m/z M$^{+1}$ 494.6. Anal. (C$_{28}$H$_{23}$Cl$_2$N$_5$O$_4$+0.29H$_2$O+0.1DMF)

ml) and heated at 100° C. for 1 h. After the solution had cooled to room temperature it was poured onto crushed ice (0.300 g) and treated with 28% NH$_4$OH until pH 3. The temperature was kept below 20° C. with an acetone-dry ice bath. The yellow solid was filtered and washed with cold ice water and air dried (11 g, 89%). The dried product was boiled with C$_6$H$_6$ (0.500 L) with continuous stirring. The solution was cooled to RT for 5 h and filtered the yellow solid major isomer 3 (6.0 g, 55%). $^1$H NMR (DMSO-d$_6$; 500 MHz): δ 7.89 (1H, d, J=6.10 Hz), 7.33 (1H, brs); 6.82 (1H, d, J=6.10 Hz), EIMS: 172.9 (M$^{-1}$).

The mother liquor was purified on SiO$_2$ gel column (30 g) by elution with (Tolune-EtOAc, (85:15) affording the desired minor isomer 4 (11.0 g, 9%). $^1$H NMR (DMSO-d$_6$; 6; 500 MHz): δ 8.83 (1H, s), 8.10 (1H, brs), 6.95 (1H, s); EIMS m/z: 174.8 (M$^{+1}$), 172.8 (M$^{-1}$).

Scheme 37

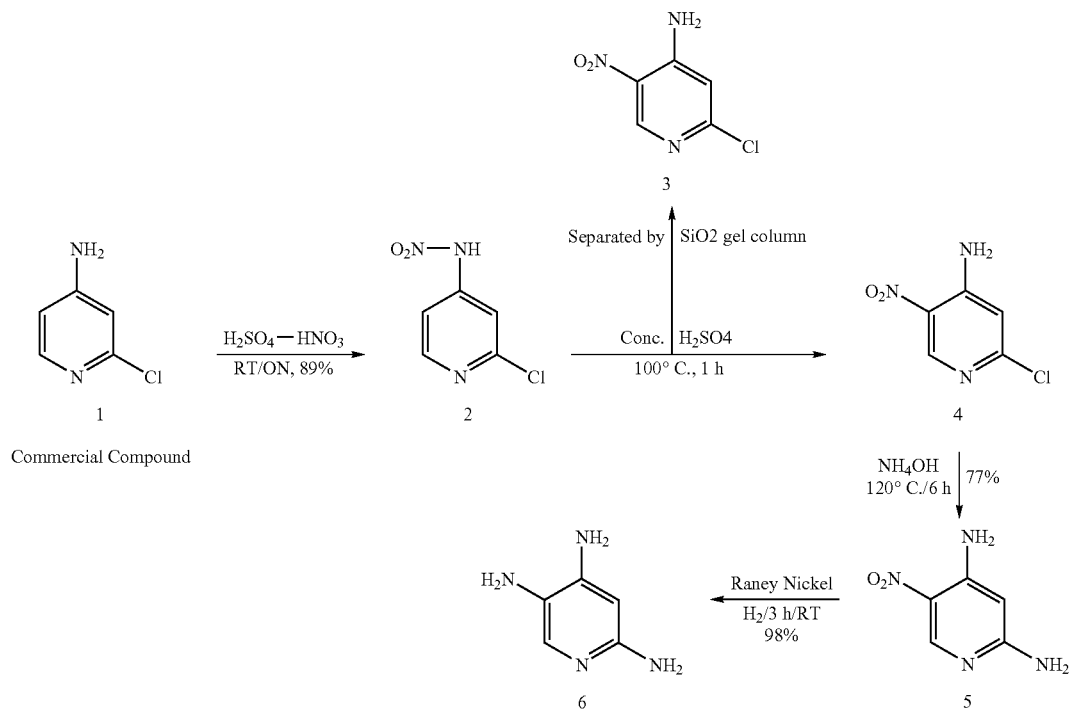

2,4,6-Triaminopyridine (5) was prepared from the ref, R. J. Rousseau and R. K. Robins; *J. Heterocyclic Chemistry*; Vol. 2; 196-201 (1965).

2 Chloro-4-aminopyridine (1): was obtained from a commercial source.

2-Chloro-4-nitraminopyridine (2): 2-Chloro-4 amino pyridine 1 (15 g) was added slowly to conc. H$_2$SO$_4$ (30 ml) at 0° C. Then a mix of conc. H$_2$SO$_4$ and fuming nitric acid (12 ml+12 ml) was added slowly over a period of 40 min. The reaction mixture was stirred at room temperature overnight and poured onto crushed ice and treated with 28% NH$_4$OH until pH 3.0. The yellowish solid was filtered and washed with cold water and air dried (2, 17.6 g, 89%) $^1$H NMR (DMSO-d$_6$, 500 MHz): δ 8.40 (1H, d, J=5.5 Hz); 7.52 (1H, brs), 7.39 (1H, dd, J=5.5 and 1.6 Hz); EIMS m/z: 196 (M+Na$^+$) and 173 (M$^+$).

4-Amino-2 chloro-3-nitropyridine (3) and 4-amino-2-chloro-5-nitropyridine (4): Finely ground 2-chloro-4-nitramine 2 (12.5 g) was carefully dissolved in conc. H$_2$SO$_4$ (100

2,4-Diamino-5-nitropyridine (5): A solution of 4-amino-2-chloro-5-nitropyridine (4) (1.0 g, 5.76 mmol) in 50 ml 28% NH$_4$OH was heated in a sealed tube at 120° C. for overnight. After cooling the reaction mixture to room temperature afforded orange red solid 5 (0.770 g, 77%). $^1$H NMR (DMSO-d$_6$, 500 MHz): δ 8.66 (1H, s), 7.35 (1H, br s), 6.73 (1H, brs), 5.67 (1H, s); EIMS m/z: 155.2 (M$^{+1}$), 153.2 (M$^{-1}$)

2,4,5-Triaminopyridine (6): A solution of 5 (0.540 g, 3.5 mmol) in EtOH (50 ml) and Raney Nickel (0.600 ml) was stirred under H$_2$ atmosphere for 3 h at room temperature. The product was freed from catalyst by filtration through celite to give 6 (0.428 g, 98%); $^1$H NMR (DMSO-d$_6$, 500 MHz): δ 7.11 (1H, s), 5.65 (1H, s) 5.12 (2H, brs), 4.64 (2H, brs) 3.34 (2H, brs); EIMS m/z: 125 (M$^{+1}$) and used as is in the next step.

Scheme 38

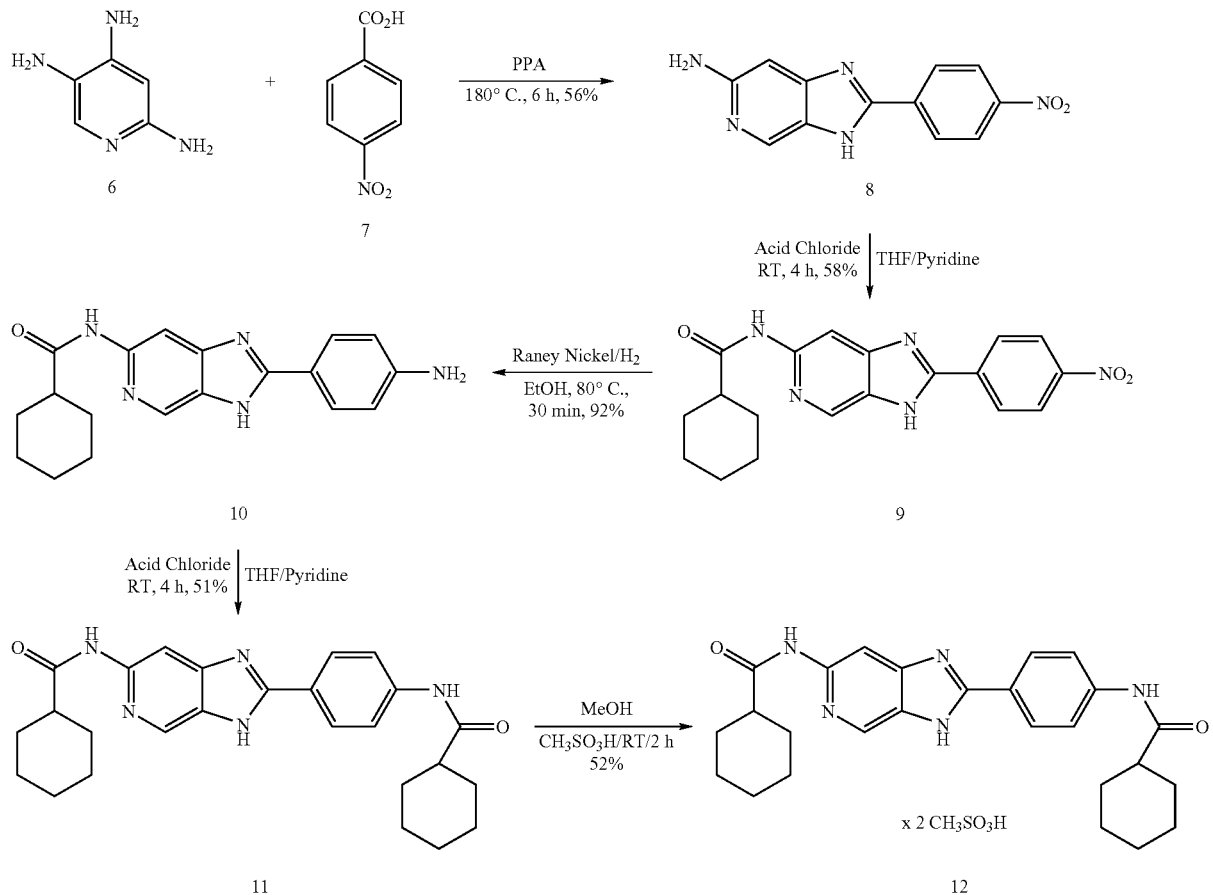

2-(4-Nitro-phenyl)-3H-imidazo[4,5-c]pyridine-6-ylamine (8): 2,4,5 Triaminopyridine (6, 0.660 g, 5.32 mmol), p-nitro benzoic acid (7, 0.888 mg 5.32 mmol) was taken in PPA (30 g) and heated at 180° C. for 7 h. The reaction mixture was cooled to room temperature and poured on to crushed ice. The excess PPA was neutralized carefully by addition of solid $K_2CO_3$ portion wise (caution) till effervescence ceased. The brownish green precipitate was filtered and washed with water and dried. The solid was taken in ($CH_2Cl_2$: MeOH:THF:$NH_4OH$ 50:30:17:3) mixture and filtered (repeated the process 3-4 times). The solvents were removed and the nitro amine precipitated with EtOAc to give 8 (0.575 g, 56%). $^1$H NMR (DMSO-$d_6$; 500 MHz): δ11.10 (1H, brs), 8.77 (1H, s), 8.45-8.25 (4H m), 6.50 (1H, s), 5.67 (2H, brs); EIMS m/z: 256.4 ($M^{+1}$) and 290 (M+Cl$^-$);

Cyclohexanecarboxylic acid [2-(4-nitro-phenyl)-3H-imidazo[4,5-c]pyridine-6-yl]-amide (9): To a stirring solution of 8 (0.116 g, 0.45 mmol) in dry THF and Pyridine (10 ml/0.300 ml), cyclohexanecarbonyl chloride (0.100 ml, 0.68 mmol) was added and stirred at room temperature for 4 h. The reaction was quenched by the addition of water and the yellow solid was filtered, air-dried and dissolved in EtOAc and passed through a bed of SiO2 gel. Elution with EtOAc afforded the desired product 9 (0.095 g, 58%). $^1$H NMR (DMSO-$d_6$, 500 MHz): δ 13.49 (1H, s), 10.38 (1H, s, NH), 8.76 (1H, s), 8.41 (4H, dd, J=15 and 5 Hz); 8.34 (1H, s), 2.53 (1H, m), 1.80-1.20 (10, m); MS m/z: 366 ($M^{+1}$), 364 ($M^{-1}$). The product was used for the next step.

Cyclohexanecarboxylic acid [2-(4-amino-phenyl)-3H-imidazo[4,5-c]pyridine-6-yl]-amide (10). A solution of 9 (0.095 g, 0.26 mmol) in EtOH (10 ml) was stirred with Raney Nickel (0.300 ml) under Hydrogen atmosphere at 80° C. for 30 min. TLC showed no starting material, product was freed from catalyst by filtration through celite to yield amine 10 (0.080 g, 92%) that was used as is for next step.

Cyclohexanecarboxylic acid [2-(4-cyclohexanecarbonyl-phenyl)-3H-imidazo[4,5-c]pyridine-6-yl]-amide (11): To a stirring solution of 10 (0.080 g, 0.24 mmol) in dry THF/Pyridine (10 ml/0.300 ml) cyclohexane carbonyl chloride (0.060 ml, 0.38 mmol) was added and stirred at room temperature for 4 h. The reaction mixture was quenched with water and stirred for 30 min. The yellow solid was filtered, dried, and purified through a bed of $SiO_2$ gel. Elution with ethyl acetate afforded the desired product 11 as light yellow solid 0.055 g (51%). Mp. 235° C.; $^1$HNMR (DMSO-d; 500 MHz): δ 12.99 (1H, brs, NH), 10.27 (1H, brs, NH), 10.07 (1H, brs, NH), 8.61 (1H, brs), 8.27 (1H, brs), 8.07 (2H, d, J=8.0 Hz), 7.79 (2H, d, J=9.0 Hz); 2.52 (1H, m), 2.36 (1H, m), 1.83-1.17 (20H, m); EIMS m/z: 446.5 ($M^{+1}$) 444.6 ($M^{-1}$); Anal. ($C_{26}H_{31}N_5O_2$·0.91$H_2O$) C, H, N Cyclohexanecarboxylic acid [2-(4-cyclohexanecarbonyl-phenyl)-3H-imidazo[4,5-c]pyridine-6-yl]-amide dimethane sulfonamide salt (12): To a solution of 11 (0.100 g, 0.225 mmol) in MeOH (5 ml), methanesulfonic acid (0.050 ml) was added and stirred at room temperature for 2 h. The solvents were removed under reduced pressure and acetone and ether were added. The solid was collected by filtration to give the product 12 (0.075 g, 52%). M.p. 258-268° C., $^1$H NMR (DMSO-$d_6$, 500 MHz): δ 11.49 (1H, brs, NH), 10.25 (1H, brs, NH), 8.79 (1H, s), 8.165 (2H, d, J=9.0 Hz), 7.87 (2H, d, J=9.0 Hz), 8.78 (1H, s), 2.40 (6H, s), 2.37 (2H, m), 1.91-1.20 (20H, m); EIMS m/z: 541.1 (M+CH$_3$SO$_3$H), 446.5 (M$^{+1}$); Anal. (C$_{28}$H$_{39}$N$_5$O$_8$S$_2$×2.20H$_2$O) C, H, N, S (1H, brs, NH), 9.60 (1H, brs, NH), 8.78 (1H, s), 8.45-8.40 (4H, m), 8.32 (1H, s), 2.00-1.60 (15H, m); EIMS m/z: 418.5 (M$^{+1}$) and 416 (M$^{-1}$).

Adamantane carboxylic acid [2-(4-amino-phenyl)-3H-imidazo[4,5-c]pyridine-6-yl]-amide (14): A solution of 13 (0.200 g, 0.48 mmol) and Raney Nickel (0.200 ml) in EtOH (10 ml) was stirred under H$_2$ atmosphere at 80° C. for 90 min. TLC showed no starting material. The product was freed from catalyst by filtering through a celite pad and

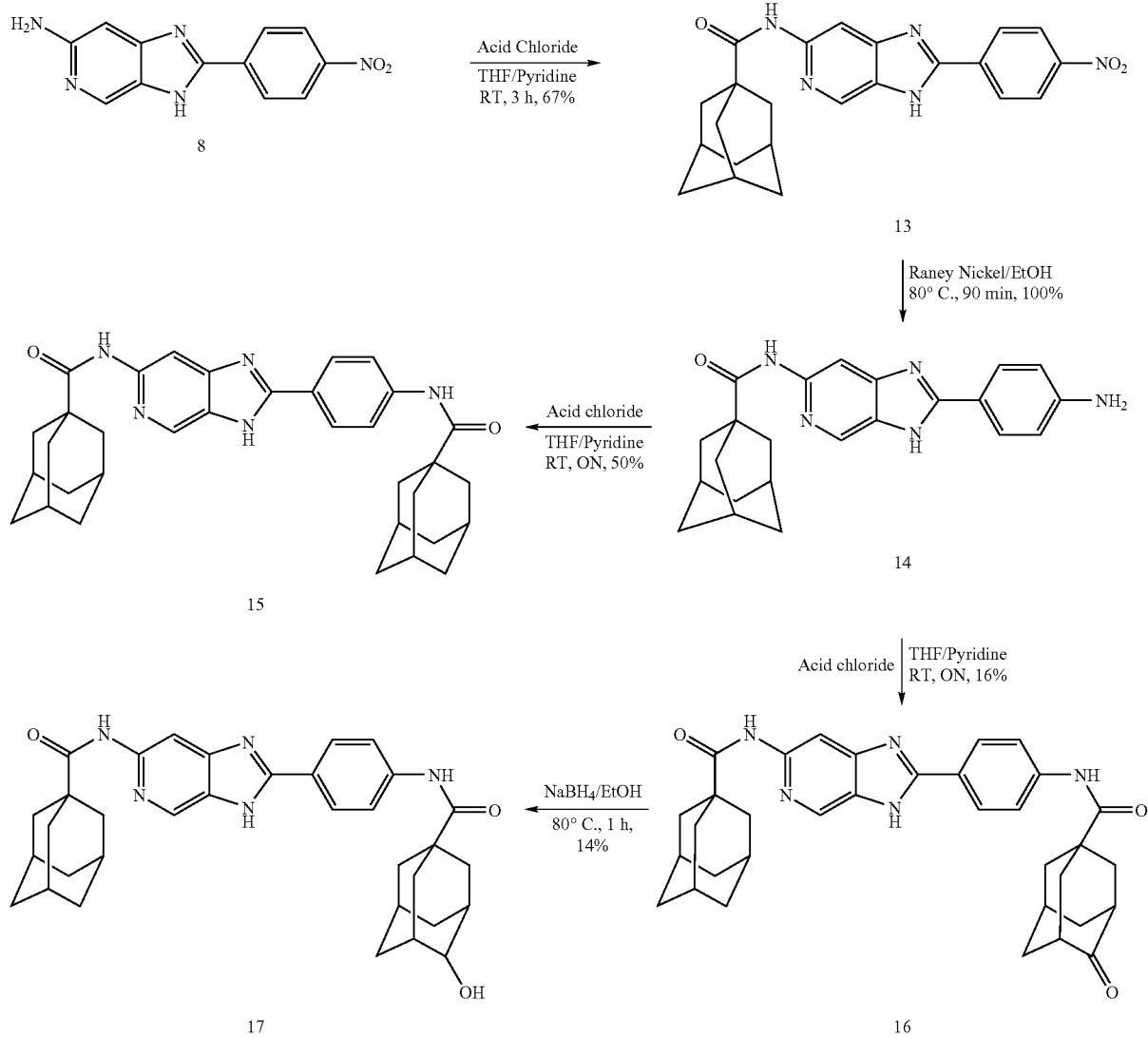

Adamantane carboxylic acid [2-(4-nitro-phenyl)-3H-imidazo[4,5-c]pyridine-6-yl]-amide (13): To a stirring solution of nitro amine 8 (0.240 g, 0.94 mmol) in dry THF-Pyridine (15 ml/0.400 ml), adamantane carbonyl chloride (0.280 g, 1.41 mmol) was added and the mixture stirred at room temperature for 3 h. The reaction was quenched by addition of water and the resulting yellow solid was filtered and passed through a SiO$_2$ gel using EtOAc as a eluent to give 13 (0.265 g, 67%). $^1$H NMR (DMSO-$d_6$, 500 MHz): δ 13.51 evaporated to dryness to afford the amine 14 (0.200 g, 100%) used for the next step.

Adamantane-1-carboxylic acid [2-(4-adamantanecarbonyl-phenyl)-3H-imidazo[4,5-c]pyridine-6-yl]-amide (15): To a solution of amine 14 (0.200 g, 0.50 mmol) in dry THF-Pyridine (10 ml/0.400 ml), adamantane carbonyl chloride (0.150 g, 0.75 mmol) was added and stirred at room temperature under argon overnight. The reaction was quenched with water and stirred at room temperature for 30 min. The yellow solid was filtered and passed through $SiO_2$ gel using $CH_2Cl_2$: MeOH (95:5) as a eluent that yielded the desired product 15 (0.150 g, 50%). M.p. 265° C.; $^1$HNMR (DMSO-$d_6$, 500 MHz): δ 13.02 (1H, brs, NH), 9.48 (1H, brs, NH), 9.37 (1H, brs, NH), 8.64 (1H, s), 8.24 (1H, s), 8.08 (2H, d, J=5.0 Hz), 7.88 (2H, d, J=5.0 Hz), 2.03-1.60 (30H, m). EIMS m/z: 449.6 ($M^{+1}$); Anal ($C_{34}H_{39}N_5O_2×0.85 H_2O$) C, H, N.

Adamantane-1-carboxylic acid [2-(4-(4-ketoadamantanecarbonylphenyl)-3H-imidazo[4,5-c]pyridine-6-yl]-amide (16): To a solution of amine 14 (0.110 g, 0.28 mmol) in dry pyridine (10 ml) at room temperature, 4-ketoadamantane carbonyl chloride (0.090 g, 0.42 mmol) was added and stirred at room temperature under argon overnight. A usual work-up (as mentioned in 15) afforded desired product 16 (0.025 g, 16%). M.p. 250° C.; $^1$H NMR (DMSO-$d_6$, 500 MHz): δ13.05 (1H, brs, NH), 9.56 (1H, brs, NH), 9.46 (1H, brs, NH), 8.26 (1H, brs), 8.24 (1H, brs), 8.11 (2H, d, J=10.0 Hz), 7.87 (2H, d, J=10.0 Hz), 2.20-1.80 (28H, m); EIMS m/z: 564 ($M^{+1}$); Anal ($C_{34}H_{37}N_5O_3×1.36 H_2O$).

Adamantane-1-carboxylic acid [2-(4-(4-hydroxyadamantanecarbonylphenyl)-3H-imidazo[4,5-c]pyridine-6-yl]-amide (17): To a solution of 16 (0.065 mg, 0.115 mmol) in EtOH (10 ml), $NaBH_4$ (0.020 g, 0.53 mmol) was added and the mixture stirred at 80° C. for 1 h. The ethanol was removed and the residue was washed with water. The product was dissolved in MeOH and THF and filtered to remove any inorganic solids. The product 17 was precipitated out with MeOH and EtOAc as a white solid and filtered 0.011 mg (14%). $^1$H NMR (DMSO-$d_6$, 500 MHz): δ 13.05 (1H, brs, NH), 9.36 (2H, brs, NH), 8.59 (1H, brs), 8.29 (1H, brs), 8.10 (2H, d, J=8.3 Hz), 7.85 (2H, brd, J=8.3 Hz), 4.70 (1H, brs, OH), 3.72-3.60 (1H, br s), 2.20-1.40 (28H, m); EIMS m/z: 566.6 ($M^{+1}$), 601.5 ($M+Cl^-$); Anal ($C_{34}H_{39}N_5O_3×3.5 H_2O$) C, H, N.

Cycloheptane carboxylic acid [2-(4-nitro-phenyl)-3H-imidazo[4,5-c]pyridine-6-yl]-amide (18): A solution of amine 8 (0.200 g, 0.78 mmol) in dry Pyridine (5 ml) and cycloheptane carbonyl chloride (0.200 ml, 1.24 mmol) was heated at 80° C. for 2 h. The reaction was quenched by addition of water and the yellow product was filtered, air dried and passed through a $SiO_2$ gel column. Eluting with hexane: EtOAc (6:4) yielded the desired product 18 (0.088 g, 30%); $^1$H NMR (DMSO-$d_6$, 500 MHz): δ10.38 (1H, brs, NH), 8.76 (1H, brs, NH), 8.44-8.39 (4H, m), 8.33 (1H, brs), 2.92 (1H, m), 1.86-145 (12H, m), EIMS m/z: 380 ($M^{+1}$), 739.1 ($M^+$).

Cycloheptane carboxylic acid [2-(4-amino-phenyl)-3H-imidazo[4,5-c]pyridine-6-yl]-amide (19): A solution of 18 (0.138 g, 0.36 mmol) and Raney Nickel (0.400 ml) in EtOH (20 ml) was heated at 80° C. under $H_2$ atmosphere for 90 min. TLC showed no starting material, the amine 19 was freed from catalyst by filtering through a celite pad and evaporating the solvent gave a solid 0.094 g (75%). That was used as is for the next step.

Cycloheptane carboxylic acid [2-(4-cycloheptanecarbonyl-phenyl)-3H-imidazo[4,5-c]pyridine-6-yl]-amide (20): The amine 19 (0.094 g, 0.27 mmol) was taken in dry Pyridine (5 ml) and cycloheptane carbonyl chloride (0.100 ml, 0.622 mmol) was added and the solution stirred at room temperature overnight. Water was added followed by sat. $NaHCO_3$ solution. The mixture was stirred at room temperature for 1 h. The solid was filtered, dried and passed through a $SiO_2$ gel column, eluting with ethyl acetate afforded a white solid 20 (0.050 g, 39%). M.p. 194° C.; $^1$H NMR (DMSO-$d_6$, 500 MHz): δ13.40 (1H, brs, NH), 10.09 (2H, s, NH), 8.81 (1H, brs), 8.145 (2H, d, J=9.0 MHz), 7.82 (2H, d, J=9.0 Hz), 2.74 (1H, m), 2.49 (1H, m), 1.91-1.25 (24H, m); EIMS m/z: 474.4 ($M^{+1}$) and 472.6 ($M^{-1}$); Anal ($C_{28}H_{35}N_5O_2$) C, H, N.

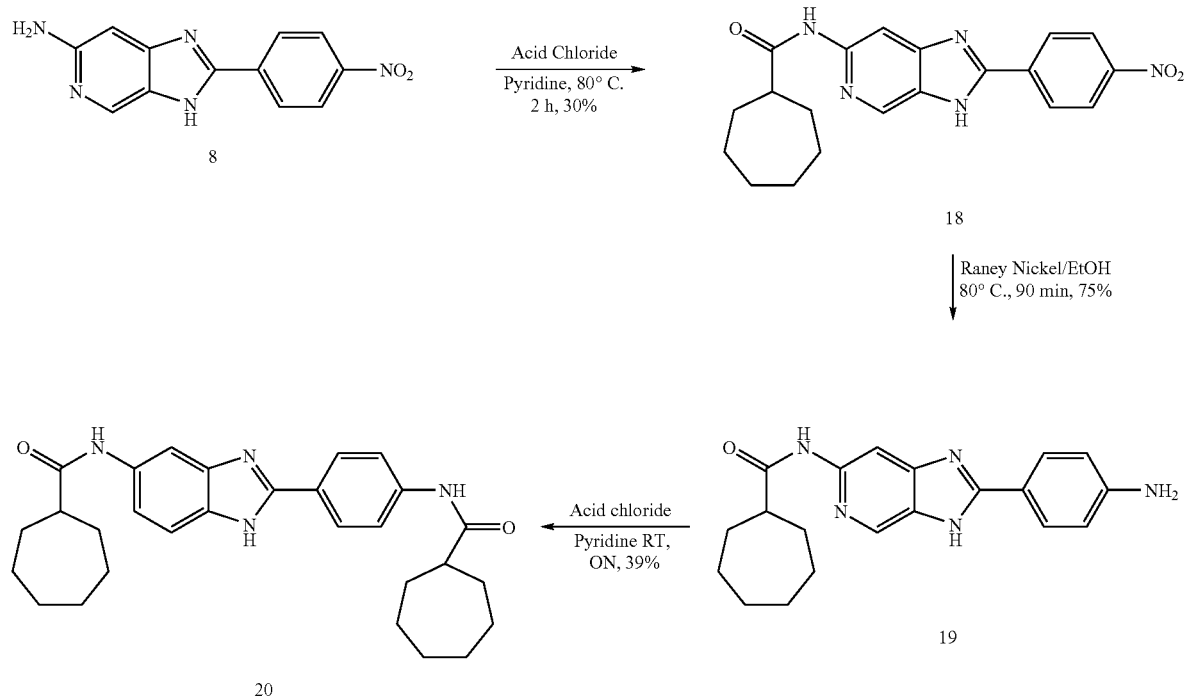

Scheme 40

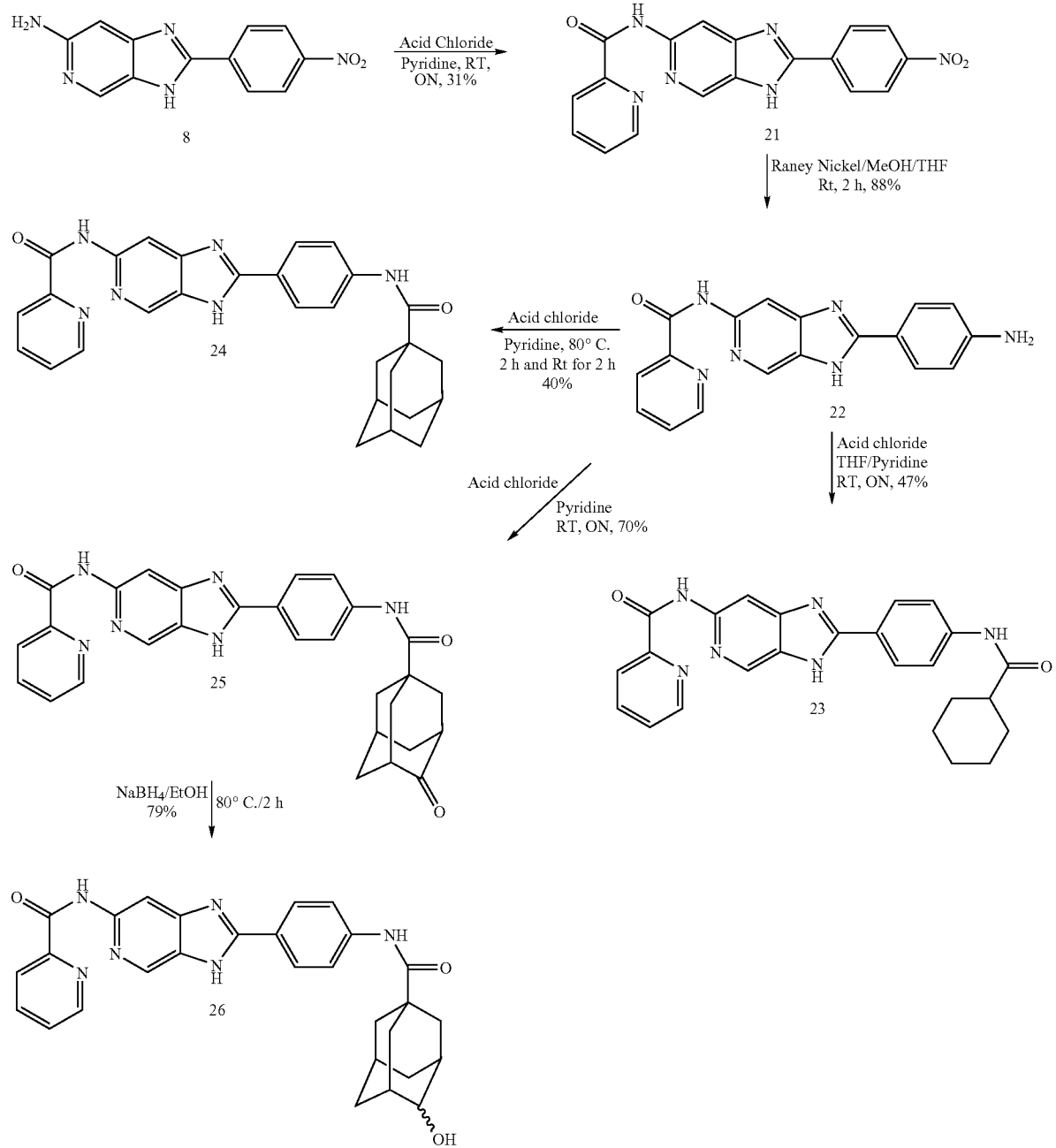

Scheme 41

Pyridine-2-carboxylic acid [2-(4-nitro-phenyl)-3H-imidazo[4,5-c]pyridin-6-yl]-amide (21): A solution of amine 8 (0.145 g, 0.57 mmol) and picolinoyl chloride hydrochloride (0.180 g, 1.01 mmol) in dry pyridine (5 ml) was stirred at room temperature overnight. After addition of water the brown solid was filtered and passed through a SiO$_2$ gel, eluting with CH$_2$Cl$_2$: MeOH (100:5) affording the desired product 21 (0.065 g, 31%).

Pyridine-2-carboxylic acid [2-(4-amino-phenyl)-3H-imidazo[4,5-c]pyridin-6-yl]-amide (22): A solution of amide 21 (0.80 g, 0.222 mmol) in THF/MeOH (5 ml/5 ml) was stirred with Raney Nickel (0.150 ml) under H$_2$ atmosphere at room temperature for 2 h. The amine was freed from catalyst by filtration through celite to give 22 (0.065 g, 88%) dried and used as is for the next step.

Pyridine-2-carboxylic acid [2-(4-cyclohexancarbonyl-phenyl)-3H-imidazo [4,5-c]pyridin-6-yl]-amide (23): A solution of amine 22 (0.040 g, 0.12 mmol) and cyclohexane carbonyl chloride (0.100 ml, 0.68 mmol) in dry THF-Pyridine (10 ml/0.300 ml) was stirred at room temperature overnight. A usual work-up as described earlier afforded the diamide 23 (0.025 g, 47%). M.p. 258° C.; $^1$H NMR (DMSO-d$_6$, 500 MHz): δ 13.5 (1H, brs, NH), 10.60 (1H, brs, NH), 10.13 (1H, brs, NH), 8.78 (1H, d, J=5.0 Hz), 8.74 (1H, brs), 8.46 (1H, brs), 8.24 (1H, d, J=12.5 Hz), 8.115 (2H, d, J=8.0 Hz), 7.81 (2H, d, J=8.0 Hz), 7.74 (1H, dt, J=10.0 and 13.5 Hz), 2.37 (1H, m), 1.84-1.18 (10H, m); EIMS m/z: 441.4 (M$^{+1}$), 439.6 (M$^{-1}$); Anal (C$_{25}$H$_{24}$N$_6$O$_2$×1.10 H$_2$O) C, H, N.

Pyridine-2-carboxylic acid [2-(4-adamantanecarbonyl-phenyl)-3H-imidazo [4,5-c]pyridin-6-yl]-amide (24): A solution of 22 (0.065 g, 0.197 mmol), adamantane carbonyl chloride (0.060 g, 0.30 mmol) in dry Pyridine (5 ml) was stirred at 80° C. for 2 h. After usual work-up the solid was treated with 10% K$_2$CO$_3$ for 1 h. The solid was filtered and passed through SiO$_2$ gel, eluting with EtOAc affording diamide 24 (0.039 g, 40%). M.p. 305° C.; $^1$H NMR (DMSO-d$_6$, 500 MHz): δ 13.19 (1H, brs, NH), 10.47 (1H, brs, NH), 9.39 (1H, brs), 8.765 (1H, d, J=4.5 Hz), 8.73 (1H, brs), 8.45 (1H, brs), 8.24 (1H, d, J=8.0 Hz), 8.14-8.09 (2H, m), 7.89 (2H, d, J=8.5 Hz), 7.72 (1H, dt, J=5.0 and 7.5 Hz), 2.0 (3H, brs), 1.92 (6H, brs), 1.72 (6H, brs); EIMS m/z: 493.5 (M$^{+1}$); Anal (C$_{29}$H$_{28}$N$_6$O$_2$×1.23 H$_2$O) C, H, N.

Pyridine-2-carboxylic acid [2-(4-(4-ketoadamantanecarbonyl-phenyl)-3H-imidazo[4,5-c]pyridin-6-yl]-amide (25): A solution of 22 (0.077 g, 0.234 mmol), 4-ketoadamantane carbonyl chloride (0.098 g, 0.46 mmol) in dry Pyridine (5 ml) was stirred at room temperature overnight. After usual work-up the solid was treated with sat NaHCO$_3$. The solid was filtered through sintered glass funnel precipitate with MeOH/ethyl acetate and hexane to give a solid 25 (0.085 g, 70%). M.p. 235° C.; $^1$H NMR (DMSO-d$_6$, 500 MHz): δ 13.19 (1H, brs, NH), 10.48 (1H, brs, NH), 9.57 (1H, brs, NH), 8.765 (1H, d, J=5.0 Hz), 8.72 (1H, brs), 8.46 (1H, brs), 8.24 (1H, d, J=7.5 Hz), 8.12 (2H, d, J=8.0 Hz), 7.87 (2H, d, J=8.0 Hz), 7.72 (1H, t, J=6.5 Hz), 2.24-1.90 (13H, m); EIMS m/z: 507.5 (M+$^1$), 529.5 (M$^{+1}$+Na$^+$), 505.6 (M$^{-1}$); Anal (C$_{29}$H$_{26}$N$_6$O$_3$×1.05 H$_2$O) C, H, N.

Pyridine-2-carboxylic acid [2-(4-(4-hydroxyadamantan-ecarbonyl-phenyl)-3H-imidazo[4,5-c]pyridin-6-yl]-amide (26): To a solution of 25 (0.057 g, 0.112 mmol) in EtOH (10 ml), NaBH$_4$ (0.020 g, 0.53 mmol) was added and the solution stirred at 80° C. for 2 h. After usual workup (mentioned previously) afforded the hydroxyl compound 26 as white solid 0.045 g (79%). M.p. 260° C.; $^1$H NMR (DMSO-d$_6$, 500 MHz): δ 3.24 and 13.19 (1H, each brs, NH) 10.48 & 10.42 (1H, each brs, NH), 9.39 & 9.33 (1H each brs, NH), 8.77 (1H, d, J=5.0 Hz), 8.72 (1H, brs), 8.64 (1H, s), 8.49 & 8.46 (1H, each s), 8.245 (1H, d, J=8.0 Hz), 8.15-8.11 (4H, m), 7.90-7.87 (4H, m), 7.73 (2H, m), 4.67 (1H each, s, OH), 3.72 & 3.64 (1H, each, brs), 2.49-1.38 (26 Hz, m); EIMS m/z: 509.6 (M$^{+1}$), 507.6 (M$^{-1}$); Anal (C$_{29}$H$_{28}$N$_6$O$_3$× 1.77 H$_2$O) C, H, N.

Scheme 42

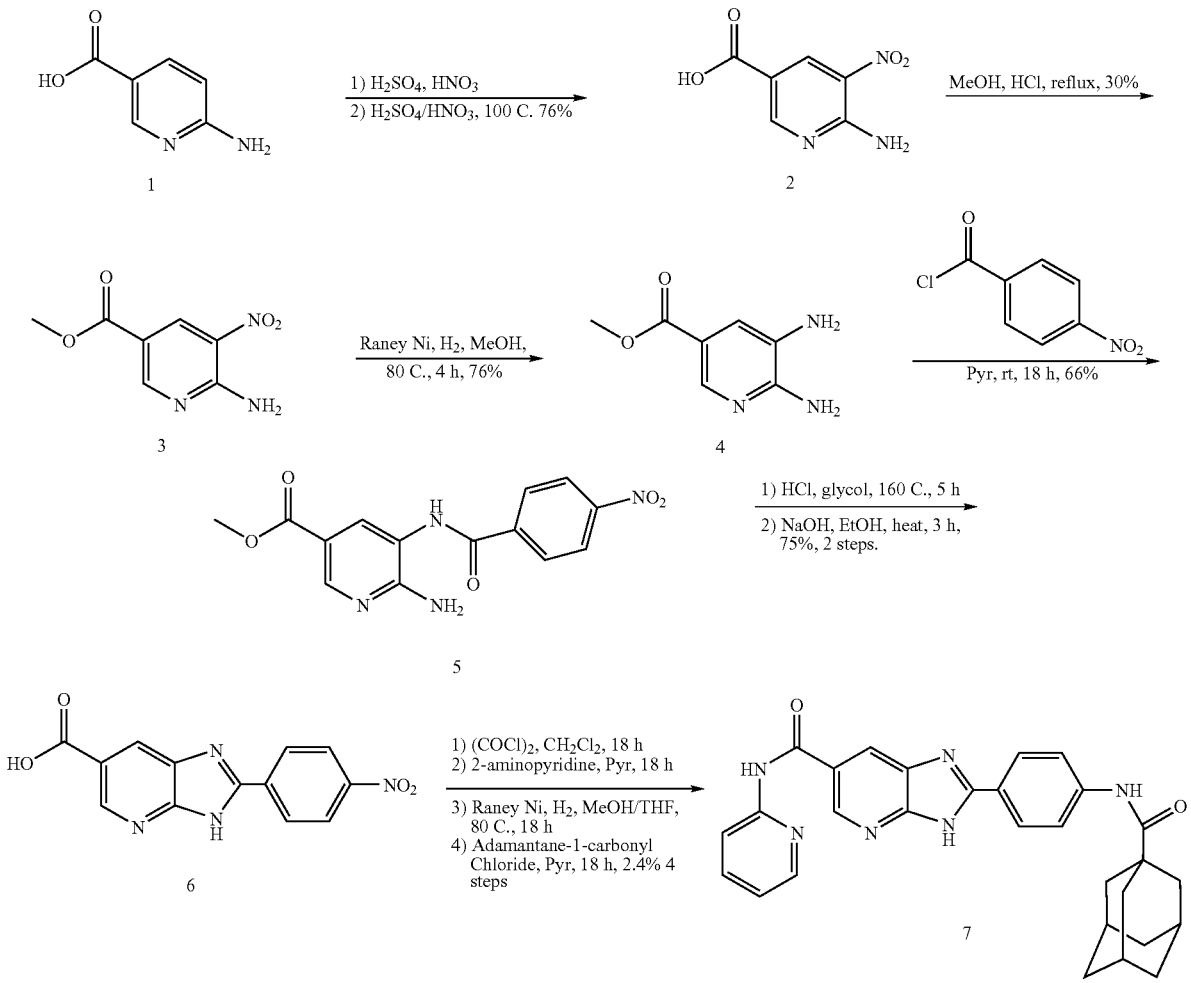

2-{4-[(Adamantane-1-carbonyl)-amino]-phenyl}-1H-pyrrolo[2,3-b]pyridine-5-carboxylic acid pyridin-2-ylamide 6-Amino-5-nitro-nicotinic acid (2). To a solution of of 6-aminonicotinic acid (1, 15 g, 109 mmol) in $H_2SO_4$ (conc. 30 ml) was added a solution of $H_2SO_4$ (conc. 7.5 ml)/$HNO_3$ (conc. 7.5 ml) dropwise over 1 h. During this time the solution turned thick milky white. Stirring was continued at room temperature for 1.5 h after which time the mixture was poured into ice/$H_2O$ (1 L) and stirred for 20 min then allowed to settle. The white solid was collected by filtration, rinsed with $H_2O$ and dried to give 18.7 grams white solid.

The solid was suspended in $H_2SO_4$ (conc. 60 ml) and heated at 100° C. for 1.5 h. The red solution was adjusted to pH ~3-4 using aqueous NaOH and the yellow solid collected by filtration and dried in vacuo to give the product as a yellow solid (15.2 g, 82.5 mmol, 76%) that was used as is without further purification.

6-Amino-5-nitro-nicotinic acid methyl ester (3). A solution of 6-Amino-5-nitro-nicotinic acid (2) (15.2 g, 82.5 mmol) in MeOH (250 ml) and $H_2SO_4$ (conc. 25 ml) was heated at reflux for 5 h. The solution was concentrated in vacuo and the residue treated with saturated aqueous $NaHCO_3$ solution until slightly basic. The resulting solid was collected by filtration, rinsed with $H_2O$ and dried in vacuo to give the product as a yellow solid (4.8 g, 25 mmol, 30%) that was used as is without further purification. TLC of the solid in DCM/MeOH (19:1) showed a less polar compound at Rf=0.5 compared to the baseline starting material.

5,6-Diamino-nicotinic acid methyl ester (4). To a suspension of 6-Amino-5-nitro-nicotinic acid methyl ester (3) (5 g, 25 mmol) in MeOH (150 ml) was added Raney Ni. The mixture was vacuum purged with $H_2$ 5 times and heated at 80° C. under $H_2$ atmosphere for 4 h. The solution was filtered through celite and concentrated in vacuo to give the product as a brown solid (3.2 g, 19 mmol, 76%) that was used without further purification. TLC of the product in DCM/MeOH (19:1) indicated a more polar spot at Rf=0.026.

6-Amino-5-(4-nitro-benzoylamino)-nicotinic acid methyl ester (5). To a solution of 5,6-Diamino-nicotinic acid methyl ester (4) (3.22 g, 19 mmol) in dry pyridine (100 ml) was added 4-nitrobenzoyl chloride (3.5 g, 19 mmol) and the mixture stirred for 18 h. The mixture was poured into $H_2O$ and the resulting solid collected by filtration, dried in vacuo to give the product as a yellow solid (4.05 g, 13 mmol, 66%). $^1$H NMR (500 MHz, DMSO-$d_6$) δ9.98 (s, 1H), 8.47 (s, 1H), 8.36 (d, J=8.7 Hz, 2H), 8.23 (d, J=8.7 Hz, 2H), 8.0 (s, 1H), 6.92 (s, 2H), 3.79 (s, 3H), EIMS m/z $M^{-1}$ 315.4.

2-(4-Nitro-phenyl)-1H-imidazo[4,5-b]pyridine-6-carboxylic acid (6). To a suspension of 6-Amino-5-(4-nitro-benzoylamino)-nicotinic acid methyl ester (5) (4.05 g, 13 mmol) in ethylene glycol (300 ml) was added conc. HCl (20 drops) and the mixture heated at 160 C for 5 h. TLC in DCM/MeOH (19:1) indicates the absence of starting material. The solution was cooled and poured into $H_2O$ and the solid collected by filtration and air-dried. $^1$H NMR (500 MHz, DMSO-$d_6$) δ14.08 (br s, 1H), 8.97 (s, 1H), 8.51 (br s, 1H), 8.49 (d, J=8.7 Hz, 2H), 8.43 (d, J=8.7 Hz, 2H), 3.92 (s, 3H). EIMS m/z $M^{-1}$ 297.3

The wet solid was suspended in EtOH (200 ml) NaOH (aq., 3%, 100 ml) was added and the solution heated at reflux for 3 h. The mixture was concentrated and the residue acidified with acetic acid. The resulting solid was collected and dried in vacuo to give the product as a slightly yellow solid (2.7 g, 9.6 mmol, 75%) that was used as is without further purification. $^1$H NMR (500 MHz, DMSO-$d_6$) δ8.97 (d, J=1.43 Hz, 1H), 8.51 (m, 3H), 8.45 (d, J=8.82 Hz, 2H). EIMS m/z $M^{-1}$ 283.4

2-{4-[(Adamantane-1-carbonyl)-amino]-phenyl}-1H-pyrrolo[2,3-b]pyridine-5-carboxylic acid pyridin-2-ylamide (7). To a solution of 2-(4-Nitro-phenyl)-1H-imidazo[4,5-b]pyridine-6-carboxylic acid (500 mg, 1.8 mmol) in dry $CH_2Cl_2$ (200 ml) was added $(COCl)_2$ (3 eq, 5.4 mmol, 463 ul) and the solution stirred for 18 h at room temperature. The mixture was concentrated under reduced pressure to give the acid chloride as a residue.

To a solution of the residue in dry pyridine (25 ml) was added 2-aminopyridine (1.8 mmol, 166 mg) as a solid and the mixture stirred for 18 h at room temperature. The mixture was poured into $H_2O$ (200 ml) and stirred for 15 min. The resulting solid was collected by filtration and dried to give a crude impure solid that was used without purification in the following reduction reaction.

To a solution of the crude residue in MeOH/THF was added Raney Ni. The solution was vacuum purged with $H_2$ 5 times and the heated at 80° C. under $H_2$ atmosphere for 18 h. The solution was filtered through celite and concentrated to give the crude product as a yellow solid (208 mg, 0.63 mmol) that was used in the following reaction without purification.

To a solution of the crude amine in dry pyridine (15 ml) was added adamantane1-carbonyl chloride (1.2 eq, 0.76 mmol, 151 mg) and the solution stirred at room temperature for 18 h. The solution as poured into $H_2O$ and stirred for 15 min. The resulting solid was collected by filtration and air dried. Purification by flash chromatography over silica using DCM/MeOH as eluent gave the product as a pale yellow solid/powder (21 mg, 0.043 mmol, 2.4% for 4 steps.) Mp: 394-396 C dec. $^1$H NMR (500 MHz, DMSO-$d_6$) δ13.56 (apparent d, 2H), 11.01 (s, 1H), 9.43 (s, 1H), 8.95 (s, 1H), 8.59 (m, 1H), 8.415 (m, 1H), 8.21 (m, 3H), 7.88 (m, 3H), 7.19 (dd, J=6 Hz, 7.2 Hz 1H), 2.04 (s, 3H), 1.95 (s, 6H), 1.72 (s, 6H), EIMS m/z $M^{+1}$ 493,6. Anal. ($C_{29}H_{28}N_6O_2$+0.4$H_2O$)

Scheme 43

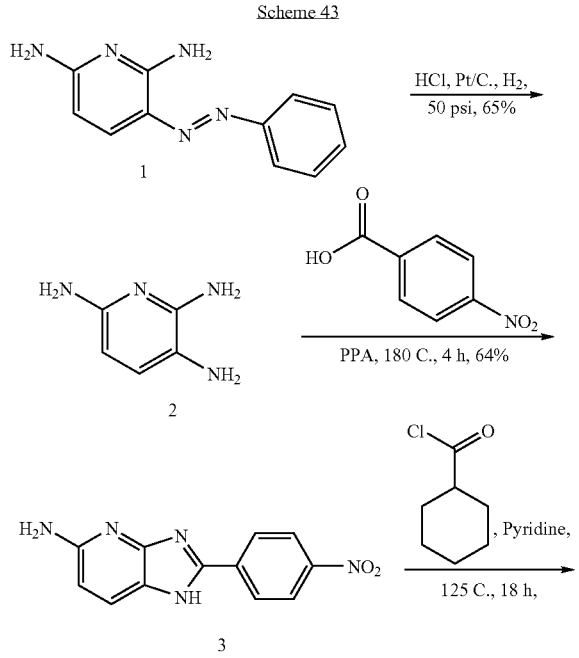

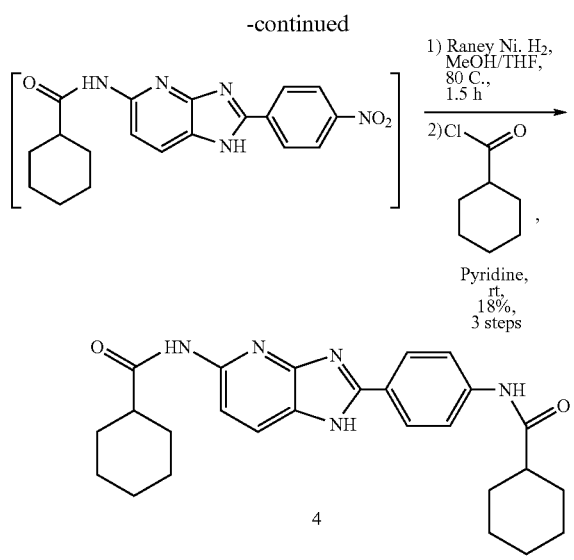

N-[2-(4-cyclohexylamino-phenyl)-1H-imidazo[-4,5-b]pyridin-5-yl]-cyclohexylamide 2,3,6-triaminopyridine (2) To a solution of phenazopyridine (1, 12.5 g, 50 mmol in HCl (25 ml, conc.) and $H_2O$ (100 ml) in a hydrogenation vessel was added Pt/C (2.5 g) and the mixture shaken under $H_2$ (50 psi) for 35 min. The mixture was concentrated under reduced pressure to 50 ml and the solid allowed to crystallize for 18 h at room temperature. The solid was collected and recrystallized from constant boiling HCl (21% HCl in $H_2O$) to give the product as a pale purple solid (4 g, 32.5 mmol, 65%). This solid was used as is without further purification.

2-(4-Nitro-phenyl)-1H-imidazo[4,5-b]pyridin-5-ylamine (3). 2,3,6triaminopyridine (2, 2 g, 1.6 mmol) was mixed with 4-nitrobenzoic acid (2.7 g, 1.6 mmol) and introduced into a flask. To this solid mixture was added PPA (40 g) and the mixture heated at 180° C. for 4 h. The mass was poured into ice cold 10% aqueous $Na_2CO_3$ (1000 ml) and the resulting solid collected by filtration. The resulting black/red solid was crystallized from DMF/$H_2O$ and rinsed with $H_2O$ after filtration. The wet solid was dried in vacuo to give the product as a brown red solid (2.61 g, 1.02 mmol, 64%). $^1$H NMR (500 MHz, DMSO-$d_6$) δ13.10 (broad S, 1H), 11.12 (broad s, 1H), 8.32 (m, 2H), 7.08 (dd, J=8.67 Hz, 636 Hz, 4H), 6.16 (broad s, 1H), EIMS m/z $M^{+1}$ 256.3.

N-[2-(4-cyclohexylamino-phenyl)-1H-imidazo[4,5-b]pyridin-5-yl]-cyclohexylamide (7). To a solution of 2-(4-Nitrophenyl)-1H-imidazo[4,5-b]pyridin-5-ylamine (3) (255 mg, 1 mmol) in pyridine (25 ml) was added cyclohexane carboxylic acid chloride (1 eq, 1 mmol, 135 ul) and the mixture heated at 125° C. for 18 h. The solution was cooled and poured into $H_2O$ (300 ml). The resulting green solid was collected by filtration and dried in vacuo to give the product as a green solid (248 mg). The solid was used as is without further purification.

To a solution of Cyclohexanecarboxylic acid [2-(4-nitrophenyl)-1H-imidazo[4,5-b]pyridin-5-yl]-amide (0.68 mmol, 248 mg) in Methanol/THF was added raney nickel and the mixture heated at 80° C. under $H_2$ atmosphere for 1.5 h. TLC in DCM/Methanol (95/5) showed no more starting material and a more polar fluorescent spot. The mixture was filtered through celite and concentrated to give a brown oil.

The brown oil was dissolved in dry pyridine and cyclohexancarboxylic acid chloride (100 ul, 109 mg) was added and the mixture stirred at room temperature for 4 h, poured into $H_2O$ and the resulting solid was collected by filtration. Purification by flash chromatography using DCM/Methanol (95/5) as eluent gave the product as a slightly purple/brown solid (54 mg, 0.12 mmol, 18%) Mp: 332-334 C. $^1$H NMR (500 MHz, DMSO-$d_6$) δ12.93 (apparent d, 1H), 10.14 (m, 2H), 8.09 (m, 1H), 7.93 (m, 2H), 7.75 (m, 2H), 2.36 (m, 1H), 1.8-1.1 (m, 14H), EIMS m/z $M^{+1}$ 446.5. Anal. ($C_{26}H_{31}N_5O_2$+0.1$H_2O$+0.51$CH_3OH$)

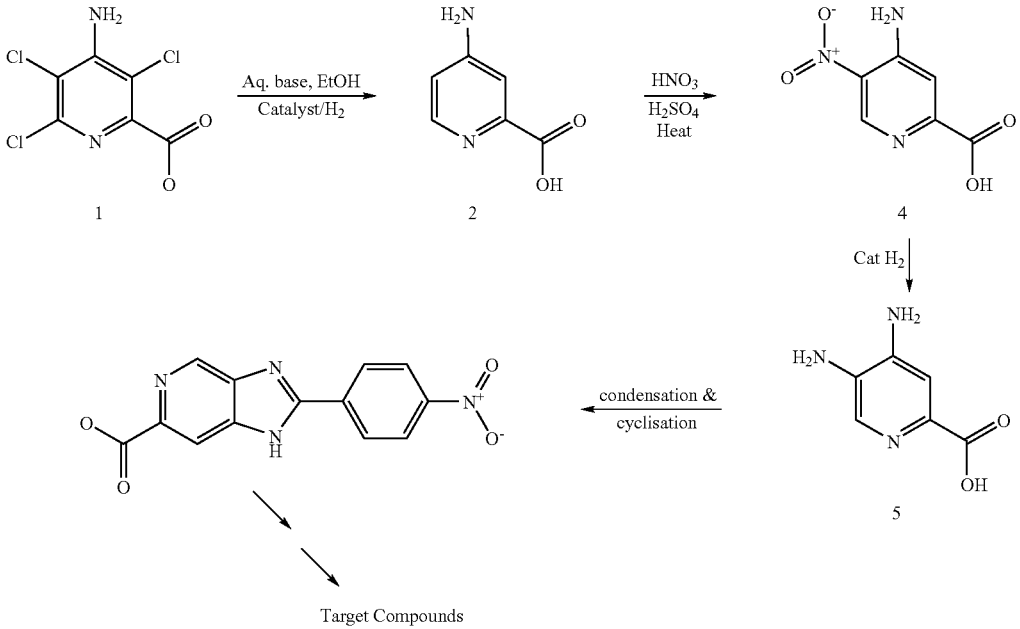

Scheme 44

Target Compounds

In regards to Scheme 44, from 5 g scaleup of first reaction, initial crop of crystals gave 2.0 g of pure 2 plus an additional approximate 1 g of 2 mixed with approximate 5 g of KCl.

Reduction of 1 on a 10 g scale using 100 ml of water as solvent gave 2, clean by NMR.

One-pot nitration and rearrangement of 2 to 4 was attempted in 9:1 TFA:triflic acid in order to avoid workup of large amounts of sulfuric acid. Nitration was successful but rearrangement did not occur. Addition of Yb(OTr)$_3$ did not help. (See Leslie Deady, Australian Journal of Chemistry, 1982, vol. 35, pp 20525-20534.)

One pot conversion of 2 to 4 was achieved using one equivalent of HNO$_3$ and a much smaller amount of H$_2$SO$_4$ (7 ml H$_2$SO$_4$ per gram of 2). Using this procedure, 1.76 g of 2 gave 2.30 g of 4 which was about 85% pure by NMR. Purity can probably improved by using KNO$_3$ as nitrating agent so that a precise stoichiometric amount can be measured.

Reduction of 4 on a 200-g scale (Pd/C, H$_2$ HOAc, 40° C., 2 h) gave 5 cleanly.

EXAMPLE 2

Suppression of IgE Response

The inhibitory activity of the small molecules of the preferred embodiments were assayed using both the ex vivo and in vivo assays as described above. All of the compounds presented above were active in suppressing the IgE response. In the ex vivo assay, compounds in Supragenera A-D produced 50% inhibition at concentrations ranging from 1 pM to 100 µM. In the in vivo assay, the compounds were effective at concentrations ranging from less than about 0.01 mg/kg/day to about 100 mg/kg/day, when administered in divided doses (e.g., two to four times daily) for at least two to seven consecutive days. Thus, the small molecule inhibitors of the preferred embodiments are disclosed as being useful in lowering the antigen-induced increase in IgE concentration, and consequently, in the treatment of IgE-dependent processes such as allergies in general and allergic asthma in particular.

EXAMPLE 3

Effects on Cellular Proliferation

A variety of experiments were performed in an effort to determine the effect of the phenyl-aza-benzimidazole compounds on cellular proliferation. These experiments ultimately measured $^3$H-thymidine incorporation into proliferating cell DNA. The specific procedure varied with the cells and the stimuli. Cells derived from mouse spleen were cultured at 3 million per ml; cell lines were seeded at 0.1 to 1 million per ml. Splenic B cells were isolated by T cell depletion and stimulated with phorbol myristate acetate (PMA) (10 ng/ml) plus ionomycin (100 nM), or IL-4 (10 ng/ml) plus anti-CD40 Ab (100 ng/ml). T cells were depleted prior to culture by incubating spleen cells first with a cocktail of anti-Thy1 ascites (10%), anti-CD4 Ab (0.5 µg/ml) and anti-CD8 Ab (0.5 µg/ml), followed by guinea pig complement (adsorbed). Cell lines were unstimulated or stimulated with Human Epidermal Growth Factor (EGF) (100 ng/ml). All cells were cultured in 96-well plates for 2-3 days and pulsed for 6 to 14 hours with 50 µl of 3H-thymidine (50 µCi/ml).

In spleen cells, certain compounds of the preferred embodiments suppressed B cell proliferation responses to PMA/ionomycin and IL-4/anti-CD40 Ab with approximately the same potencies as it suppressed in vitro IgE responses to IL-4/anti-CD40 Ab. Similar inhibition potencies were obtained for certain compounds of the preferred embodiments in ConA-stimulated T cell proliferation and LPS-stimulated B cell proliferation (preformed by MDS Pharma), suggesting a lack of specificity in the action of these drugs. On the other hand, a battery of immunological tests performed with certain compounds of the preferred embodiments demonstrated little other effects other than inhibition of ConA-stimulated cytokine release.

In tumor cells, the results with splenic lymphocytes led to a further analysis of cellular proliferation by measuring the growth of tumor cells in the presence of these drugs. The initial analysis was performed with murine M12.4.1 lymphoma cells, either un-stimulated or stimulated with IL-4/anti-CD40 Ab. Certain compounds of the preferred embodiments suppressed the proliferation of M12.4.1 cells but with lower potency that observed in stimulated spleen cells. However, the potency of compounds of the preferred embodiments increased when the cells were cultured with IL-4/anti-CD40 Ab. This stimulation is known to induce the activity of NF-κB in M12.4.1 cells.

A similar approach was used to establish selectivity of the anti-proliferative activity by testing a battery of tumor lines derived from a variety of tissues, mostly human in origin. An attempt was made to generate proliferation data from at least 2 cell lines from each tissue selected. Only a handful of cell lines were inhibited by 100 nM or less of each compound while most the balance of the cells required much higher concentrations. Because of the known character of some of the tested cell lines and previous Western blot results with the compounds, there is evidence to suggest a link between NF-κB inhibition and the action of the drugs. Breast cancer cells offer a good model for testing this phenomenon because they are predominantly of 2 types; estrogen receptor (ER)-positive and ER-negative. The latter cells tend to be less differentiated, have a higher density of EGF receptor expression, and are more resilient to treatment. Proliferation of ER-negative/EGFR-positive cells also tends to be driven by NF-κB and thus a selection of these cells were tested for proliferation responses to drug in vitro. The proliferation of all of the EGF-responsive cell lines was potently inhibited by compounds of the preferred embodiments in vitro. Conversely, only 2 of the 5 ER-positive cell lines were potently inhibited by drug.

Certain compounds of the preferred embodiments exert an anti-proliferative activity to T and B lymphocytes exposed to a variety of immunogenic stimuli in vitro. These actions are highly potent and parallel their IgE-suppression activity. Although the mechanism of this action is unresolved, much is known about the mechanism of IL-4/anti-CD40 Ab-induced IgE production. A major factor in this response is the transcription activator, NF-κB. This factor has been implicated in the proliferation of a number of tumor cells and thus these drugs were tested for activity on the proliferation of various tumor cell lines in vitro. Our experiments revealed that a number of tumor cell lines are sensitive to the effects of compounds of the preferred embodiments, and that proliferation of many of the sensitive lines may be driven by NF-κB factors. However, other cell lines known to be driven by factors other than NF-κB (e.g., the ER-positive HCC 1500 and ZR-75-1). Thus, certain compounds of the preferred embodiments appears to selectively act on certain tumor cells. Other compounds disclosed in accordance with the present invention are also expected to exhibit similar characteristics, particularly those compounds which are structurally similar to certain compounds of the preferred embodiments.

Treatment Regimens

The amount of the aza-benzimidazole compounds which can be effective in treating a particular allergy or used as an anti-proliferation agent will depend on the nature of the disorder, and can be determined by standard clinical techniques. The precise dose to be employed in a given situation will also depend on the choice of compound and the seriousness of the condition, and should be decided according to the judgment of the practitioner and each patient's circumstances.

As an anti-allergy therapy, appropriate dosages can be determined and adjusted by the practitioner based on dose response relationships between the patient's IgE levels as well as standard indices of pulmonary and hemodynamic changes. Moreover, those skilled in the art will appreciate that dose ranges can be determined without undue experimentation by following the protocol(s) disclosed herein for ex vivo and in vivo screening (See for example Hasegawa et al., *J. Med. Chem.* 40: 395-407 (1997) and Ohmori et al., *Int. J. Immunopharmacol.* 15:573-579 (1993); employing similar ex vivo and in vivo assays for determining dose-response relationships for IgE suppression by naphthalene derivatives; incorporated herein by reference).

Initially, to exert anti-allergic or anti-asthmatic effects, suitable dosages of the compounds will generally range from about 0.001 mg to about 300 mg per kg body weight per day in divided doses, more preferably, between about 0.01 mg and 100 mg per kg body weight per day in divided doses. The compounds are preferably administered systemically as pharmaceutical formulations appropriate to such routes as oral, aerosol, intravenous, subcutaneously, or by any other route which may be effective in providing systemic dosing of the active compound. The compositions of pharmaceutical formulations are well known in the art. The treatment regimen preferably involves periodic administration. Moreover, long-term therapy may be indicated where allergic reactions appear to be triggered by continuous exposure to the allergen(s). Daily or twice daily administration has been effective in suppressing the IgE response to a single antigen challenge in animals when carried out continuously from a period of two to seven consecutive days. Thus, in a preferred embodiment, the compound is administered for at least two consecutive days at regular periodic intervals. However, the treatment regimen, including frequency of dosing and duration of treatment may be determined by the skilled practitioner, and modified as needed to provide optimal IgE down-regulation, depending on nature of the allergen, the dose, frequency, and duration of the allergen exposure, and the standard clinical indices.

In a preferred embodiment, an IgE-suppressing compound can be administered in conjunction with one or more of the other small molecule inhibitors disclosed, in order to produce optimal down-regulation of the patient's IgE response. Further, it is envisioned that one or more of the compounds of the preferred embodiments can be administered in combination with other drugs already known or later discovered for treatment of the underlying cause as well as the acute symptoms of allergy or asthma. Such combination therapies envisioned within the scope of the present invention include mixing of one or more of the small molecule IgE-inhibitors together with one or more additional ingredients, known to be effective in reducing at least one symptom of the disease condition. In a variation, the small molecule IgE-inhibitors herein disclosed can be administered separately from the additional drugs, but during the same course of the disease condition, wherein both the IgE-inhibitor(s) and the palliative compounds are administered in accordance with their independent effective treatment regimens.

As an anti-proliferative therapy, the appropriate dose of the aza-benzimidazole compounds disclosed herein can be determined by one skilled in the art. Pharmacologists and oncologists can readily determine the appropriate dose required for each individual patient without undue experimentation, based upon standard treatment techniques used for other anti-proliferation and chemotherapeutic agents.

Initially, suitable dosages of the anti-proliferation aza-benzimidazole compounds will generally range from about 0.001 mg to about 300 mg per kg body weight per day in divided doses, more preferably, between about 0.01 mg and 100 mg per kg body weight per day in divided doses. Most preferably, to exert anticancer effects, the dose will range from about 1 mg to 100 mg per kg body weight per day. The compounds are preferably administered systemically as pharmaceutical formulations appropriate to such routes as oral, aerosol, intravenous, subcutaneously, or by any other route which may be effective in providing systemic dosing of the active compound.

Ideally one or more aza-benzimidazole compounds of the preferred embodiments should be administered to achieve peak plasma concentrations of the active agent, as determined by one of skill in the art. To achieve adequate plasma levels, the pharmaceutical formulation can be injected intravenously in an appropriate solution, such as a saline solution or administered as a bolus of the active ingredient.

The treatment regimen used in accordance with preferred embodiments preferably involves periodic administration. Moreover, as with other chemotherapeutic agents, long-term therapy may be indicated. Weekly, daily or twice daily administration for a period of one to three years may be required for some patients. Thus, in a preferred embodiment, the compound is administered for at least six months at regular periodic intervals. However, the treatment regimen, including frequency of dosing and duration of treatment may be determined by the skilled practitioner, and modified as needed to provide optimal anti-proliferation effects, depending on nature of the disease, the extent of abnormal cell growth, the type of cancer, the tissues affected, and standard clinical indices.

One skilled in the art will understand that the ideal concentration of the anti-proliferation compounds in the formulation depends upon several pharmacokinetic parameters, such as, absorption, inactivation, metabolism and clearance rates of the drug, as well as other known factors. One skilled in the art will also appreciate that the concentration will vary with the severity of the condition to be treated. Other factors which may affect the treatment dose include, tumor location, age and gender of the patient, other illnesses, prior exposure to other drugs, and the like. One skilled in the art will appreciate that for any particular patient, specific treatment regimens will be evaluated and adjusted over time according to the individual patient's requirements and according to the professional judgment of the medical practitioner administering the treatment.

In one preferred embodiment, compounds are orally administered. Preferably, oral formulations will include inert diluents or edible carriers. Oral dosages may be encapsulated in gelatin or formed into tablets. Oral administration may also be accomplished by using granules, grains or powders, syrups, suspensions, or solutions. One skilled in the art will understand that many acceptable oral compositions may be used in accordance with preferred embodiments. For example, the active compound may be combined with standard excipients, adjuvants, lubricants, sweetening agents, enteric coatings, buffers, stabilizing agents and the like.

In another embodiment, the active compound may be modified to include a targeting moiety that targets or concentrates the compound at the active site. Targeting moieties include, but are not limited to, antibodies, antibody fragments or derivatives, cytokines, and receptor ligands expressed on the cells to be treated.

In preferred embodiments, compounds are administered in conjunction with other active agents, which either supplement or facilitate the action of the aza-benzimidazole compound or cause other independent ameliorative effects. These additional active agents include, but are not limited to, antifungals, antivirals, antibiotics, anti-inflammatories, and anticancer agents. Protectants, which include carriers or agents which protect the active benzimidazole compound from rapid metabolism, degradation or elimination may also be used. Controlled release formulations can also be used in accordance with preferred embodiments.

In another embodiment, one or more anti-proliferation compounds may be administered in conjunction with one or more other anti-cancer agents or treatments to produce optimal anti-proliferative effects. Anti-cancer agents include, but are not limited to, alkylating agents (lomustine, carmustine, streptozocin, mechlorethamine, melphalan, uracil nitrogen mustard, chlorambucil cyclophosphamide, iphosphamide, cisplatin, carboplatin mitomycin thiotepa dacarbazine procarbazine, hexamethyl melamine, triethylene melamine, busulfan, pipobroman, and mitotane); antimetabolites (methotrexate, trimetrexate pentostatin, cytarabine, ara-CMP, fludarabine phosphate, hydroxyurea, fluorouracil, floxuridine, chlorodeoxyadenosine, gemcitabine, thioguanine, and 6-mercaptopurine); DNA cutters (bleomycin); topoisomerase I poisons (topotecan irinotecan and camptothecin); topoisomerase II poisons (daunorubicin, doxorubicin, idarubicin, mitoxantrone, teniposide, and etoposide); DNA binders (dactinomycin, and mithramycin); and spindle poisons (vinblastine, vincristine, navelbine, paclitaxel, and docetaxel).

Further, it is envisioned that one or more of the compounds of the preferred embodiments can be administered in combination with other therapies, such as radiation, immunotherapy, gene therapy and/or surgery, in order to treat hyperproliferative diseases, including cancer. Such combination therapies envisioned within the scope of the present invention include mixing of one or more of the aza-benzimidazole compounds together with one or more additional ingredients, known to be effective in reducing at least one symptom of the disease condition. In a variation, the aza-benzimidazole compounds herein disclosed may be administered separately from the additional drugs, but during the same course of the disease condition, wherein both the aza-benzimidazole compound and the palliative compounds are administered in accordance with their independent effective treatment regimens.

While a number of preferred embodiments and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A compound or salt thereof represented by one or more of the following formulas:

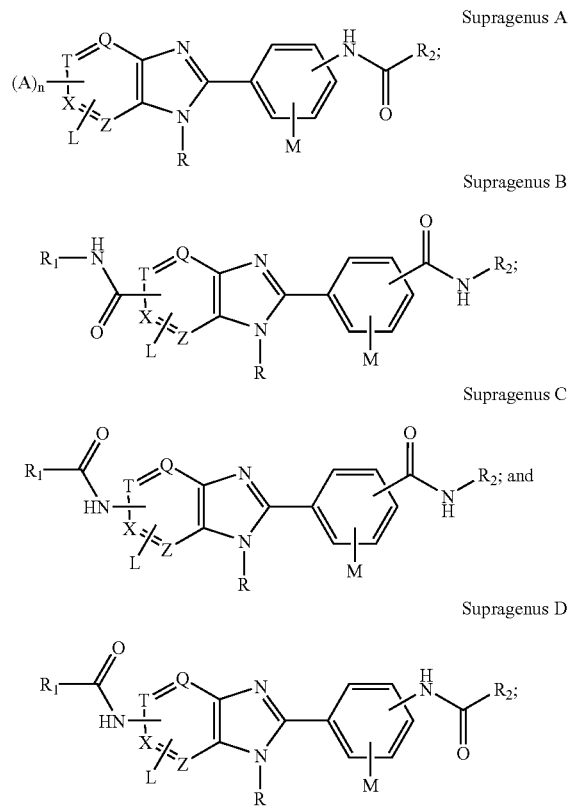

wherein Q, T, X, and Z are independently selected from N or C, and wherein one of Q, T, X, and Z is N;

wherein A is selected from the group consisting of H, halogen, and $CONHR_1$;

wherein n is a number from one to four;

wherein L is selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein M is selected from the group consisting of H, alkyl, alkoxy, aryl, substituted aryl, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, OCH₃, COOH, COOR' COR', CN, CF₃, OCF₃, NO₂, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

2. The compound or salt thereof of claim 1, wherein the Supragenus A-D are represented by the formulas:

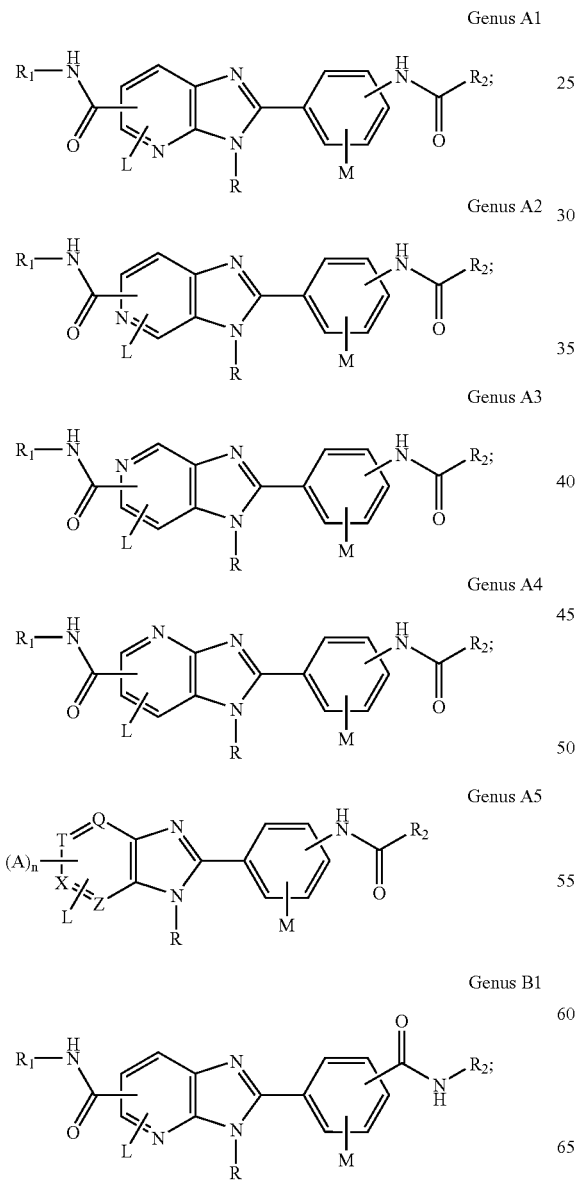

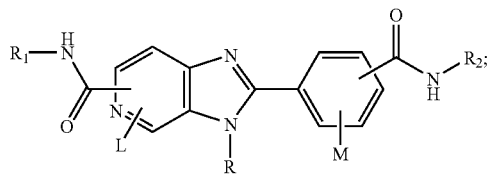

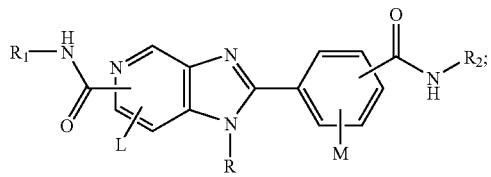

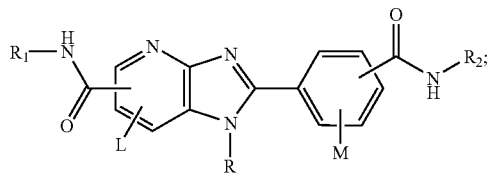

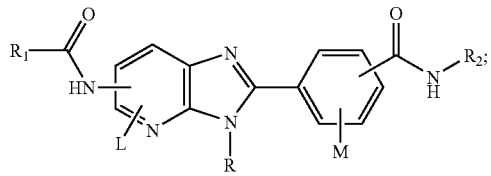

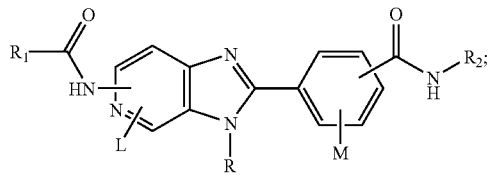

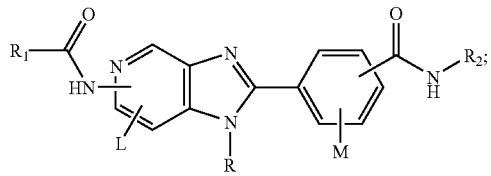

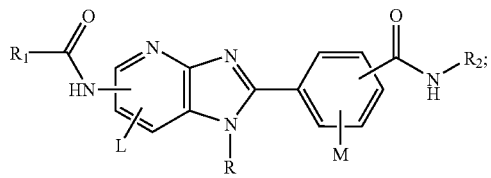

Genus D1
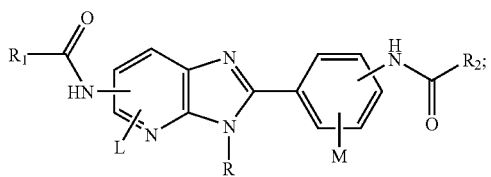

Genus D2
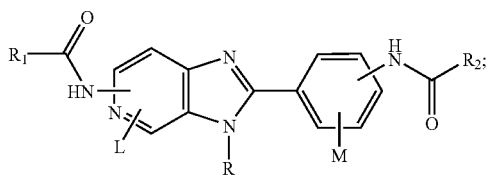

Genus D3
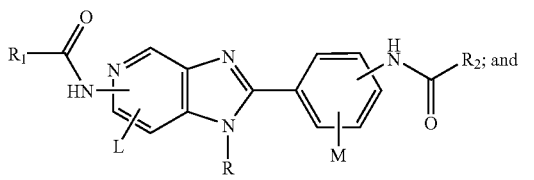

Genus D4
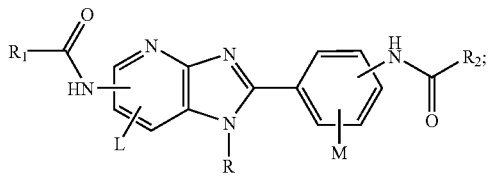

wherein Q, T, X, and Z are independently selected from N or C, and wherein one of Q, T, X, and Z is N;

wherein A is selected from the group consisting of H and halogen;

wherein n is a number from one to four;

wherein L is selected from the group consisting of H, alkyl, alkoxy, aryl, substituted aryl, hydroxy, halogen, amino, alkylamino, nitro, cyano, $CF_3$, $OCF_3$, $CONH_2$, CONHR and $NHCOR_1$;

wherein M is selected from the group consisting of H, alkyl, alkoxy, aryl, substituted aryl, amino, alkylamino, nitro, cyano, $CF_3$, $OCF_3$, $CONH_2$, CONHR and $NHCOR_1$;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR' COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

3. The compound or salt thereof of claim 1, wherein said polycyclic aliphatic group is selected from the group consisting of adamantyl, bicycloheptyl, camphoryl, bicyclo[2,2,2]octanyl and norbornyl.

4. The compound or salt thereof of claim 1, wherein said heteroaryl and said substituted heteroaryl is selected from the group consisting of pyridines, thiazoles, isothiazoles, oxazoles, pyrimidines, pyrazines, furans, thiophenes, isoxazoles, pyrroles, pyridazines, 1,2,3-triazines, 1,2,4-triazines, 1,3,5-triazines, pyrazoles, imidazoles, indoles, quinolines, iso-quinolines, benzothiophines, benzofurans, parathiazines, pyrans and chromenes.

5. The compound or salt thereof of claim 1, wherein $R_1$ and $R_2$ are independently selected from the group consisting of:

2

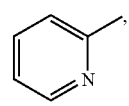
1

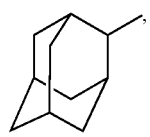
3

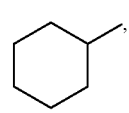
4

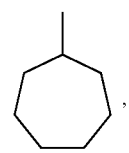
5

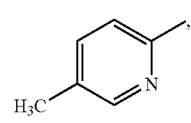
6

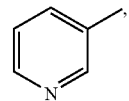
7

8 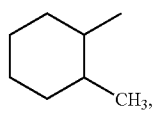
9 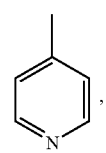
10 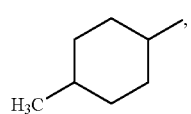
11 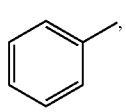
12 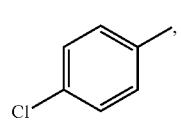
13 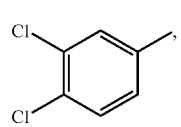
14 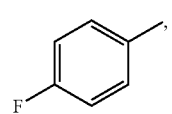
15 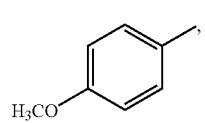
16 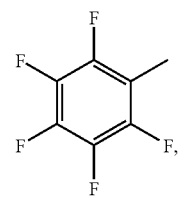
17 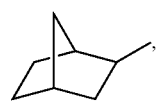
18 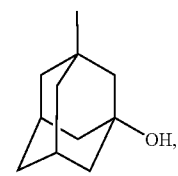
19 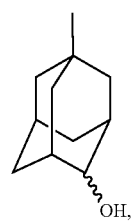
20 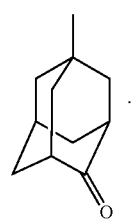
6. The compound or salt thereof of claim 1 selected from the group consisting of:
S-1 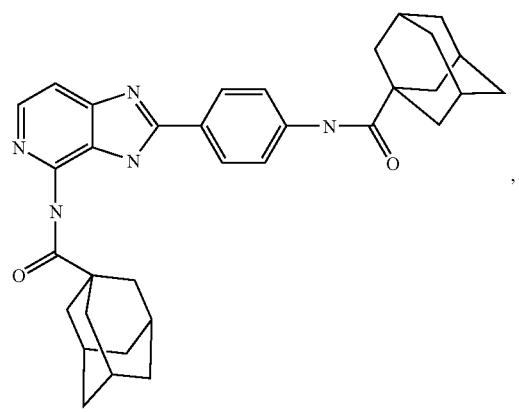
S-2 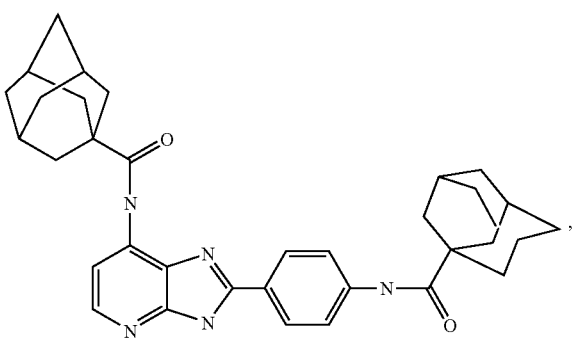

-continued
S-3
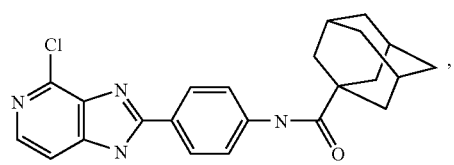
S-4
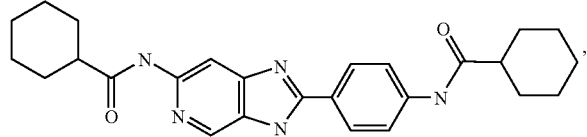
S-5
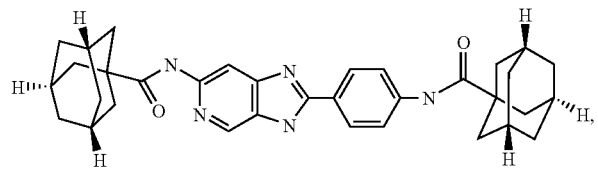
S-6
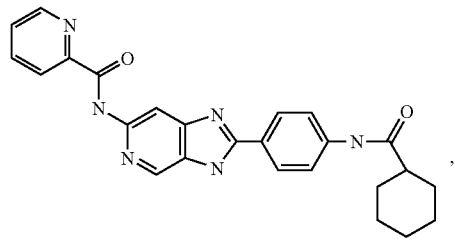
S-7
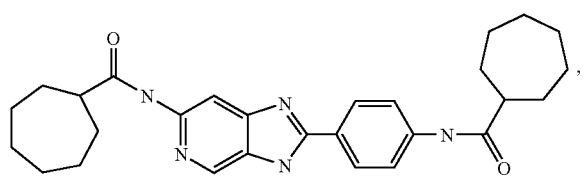
S-8
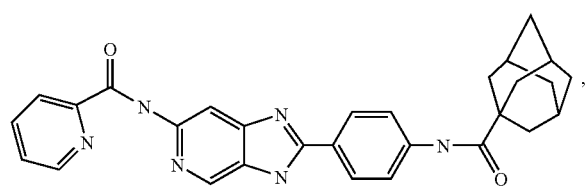
S-9
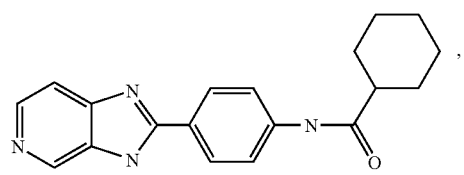
S-10
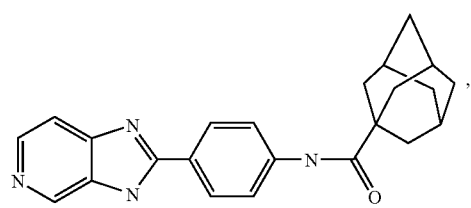
S-11
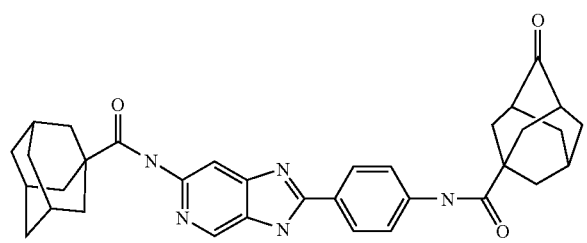
S-12
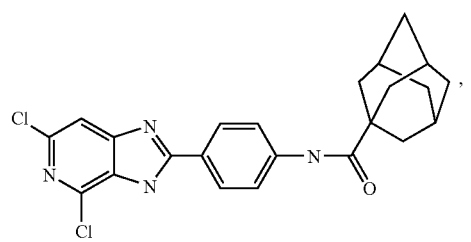
S-13
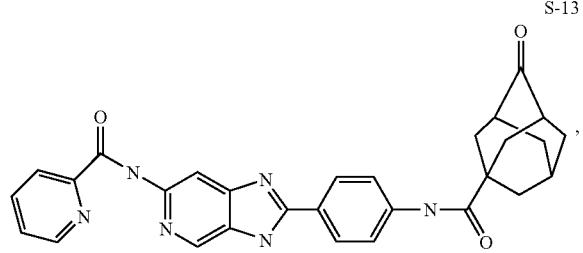
S-14
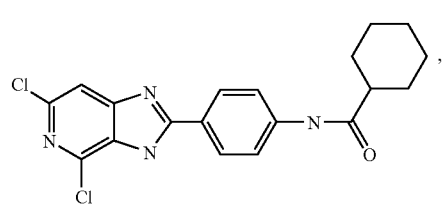

-continued
S-15
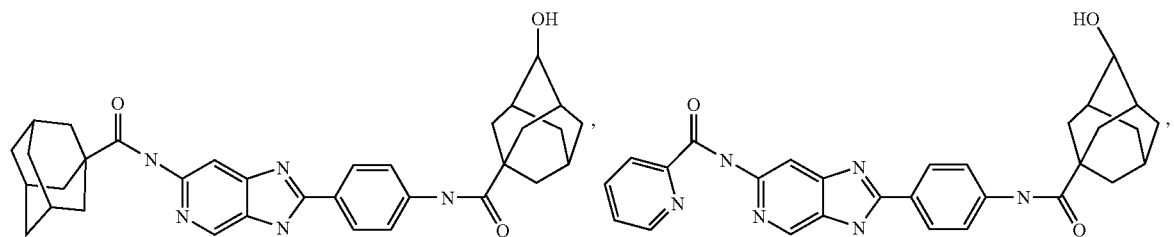
S-16
S-17
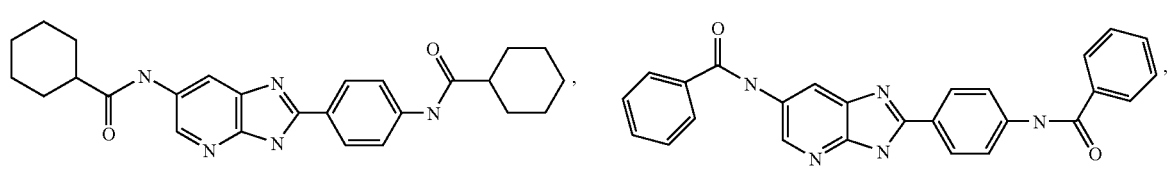
S-18
S-19
S-20
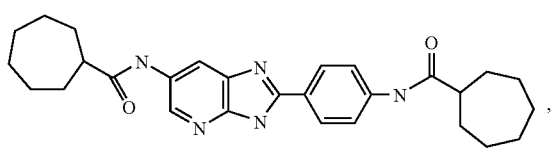
S-21
S-22
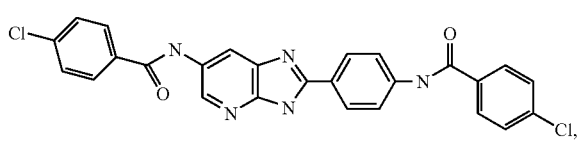
S-23
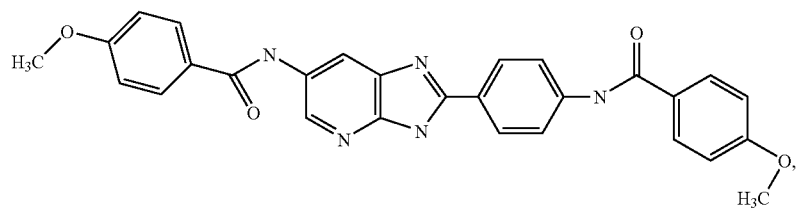
S-24
S-25
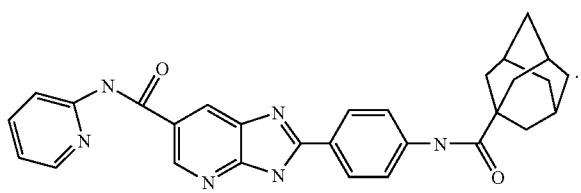

7. A compound or salt thereof represented by the following formula:

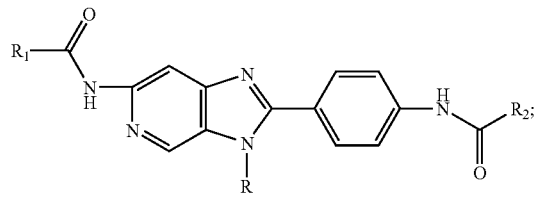

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said hetero atom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR' COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

8. The compound or salt thereof of claim 7 selected from the group consisting of:

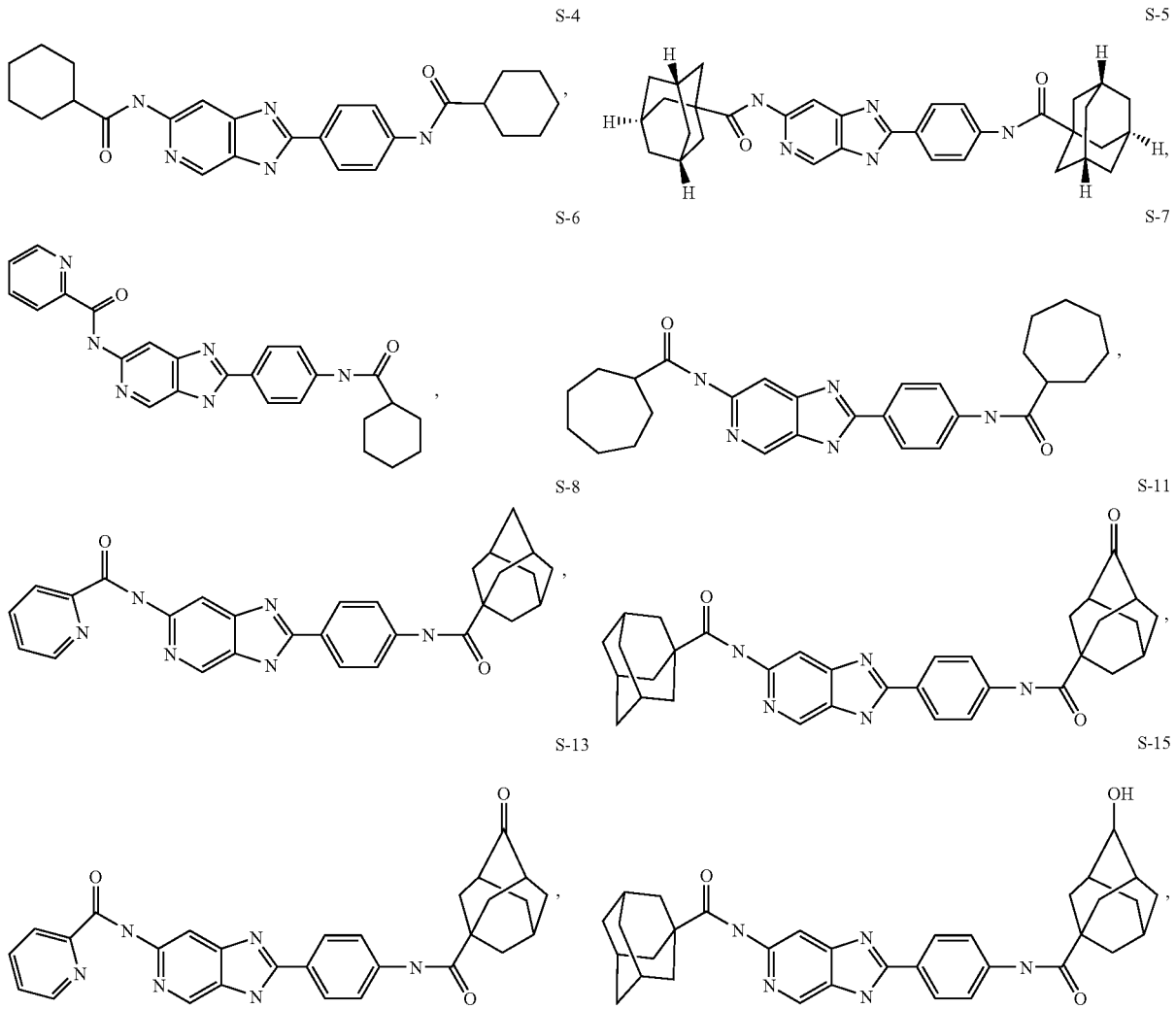

-continued

S-16

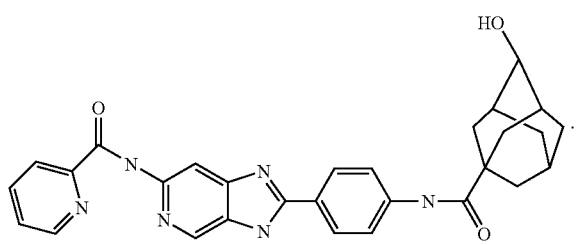

9. The compound or salt thereof of claim 8 represented by the formula:

S-7

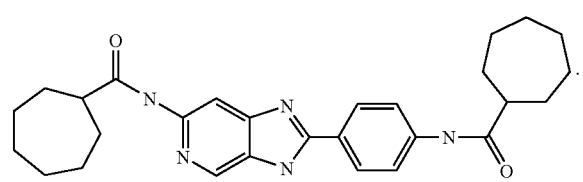

10. A compound or salt thereof represented by the following formula:

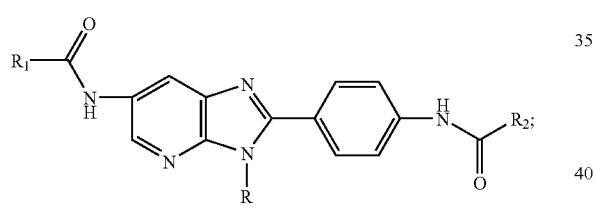

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR' COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

11. The compound or salt thereof of claim 10 selected from the group consisting of:

S-17

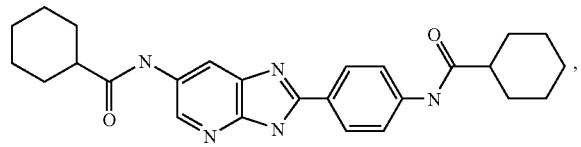

and

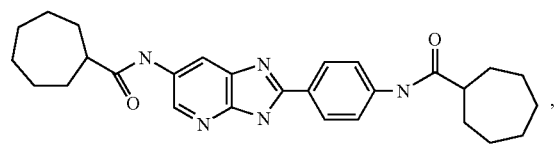

S-19

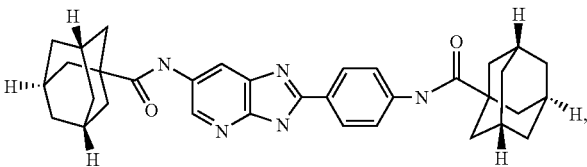

S-20

S-21

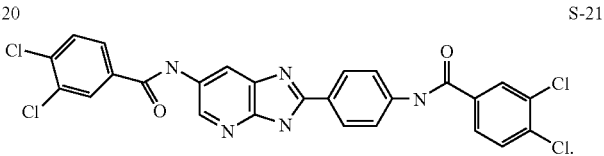

12. A compound or salt thereof represented by the following formula:

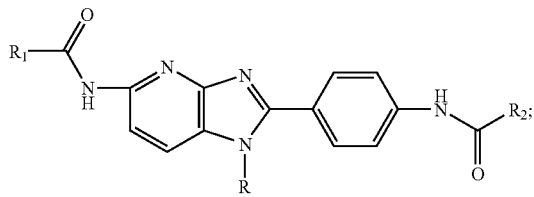

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR' COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

13. The compound or salt thereof of claim 12 represented by the formula:

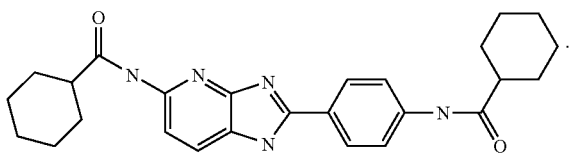

S-24

14. A compound or salt thereof represented by the following formula:

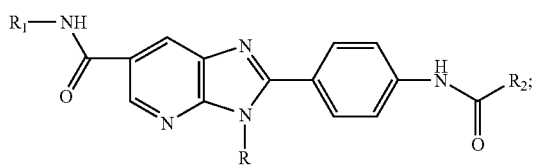

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said hetero atom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR' COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

15. The compound or salt thereof of claim 14 represented by the formula:

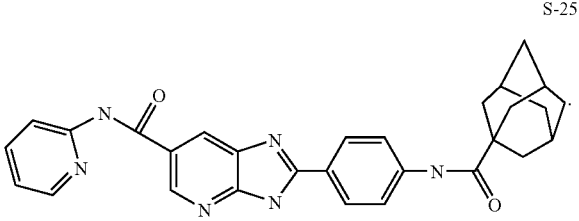

S-25

16. A compound or salt thereof represented by the following formula:

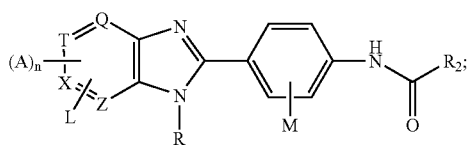

wherein T and X are independently selected from N or C, and wherein one of T and X is N;

wherein A is selected from the group consisting of H, halogen, and $CONHR_1$;

wherein n is a number from one to four;

wherein R is selected from the group consisting of H, $C_1$-$C_5$ alkyl, benzyl, p-fluorobenzyl and di-alkylamino alkyl, wherein said $C_1$-$C_5$ alkyl is selected from the group consisting of a straight chain, branched or cyclic alkyl;

wherein $R_1$ and $R_2$ are independently selected from the group consisting of H, alkyl, substituted alkyl, $C_3$-$C_9$ cycloalkyl, substituted $C_3$-$C_9$ cycloalkyl, polycyclic aliphatic groups, substitued polycyclic aliphatic groups, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur;

wherein said substituted polycyclic aliphatic groups, substituted phenyl, substituted naphthyl and substituted heteroaryl contain 1-3 substituents, wherein said substituent is selected from the group consisting of H, halogens, polyhalogens, alkoxy group, substituted alkoxy, alkyl, substituted alkyl, dialkylaminoalkyl, hydroxyalkyl, carbonyl, OH, $OCH_3$, COOH, COOR' COR', CN, $CF_3$, $OCF_3$, $NO_2$, NR'R', NHCOR' and CONR'R'; and wherein R' is selected from the group consisting of H, alkyl, substituted alkyl, $C_3$-$C_9$ cycloalkyl, substituted $C_3$-$C_9$ cycloalkyl, polycyclic aliphatics, phenyl, substituted phenyl, naphthyl, substituted naphthyl, heteroaryl and substituted heteroaryl, wherein said heteroaryl and said substituted heteroaryl contain 1-3 heteroatoms, wherein said heteroatom is independently selected from the group consisting of nitrogen, oxygen and sulfur.

17. A compound or salt thereof represented by the following formula:

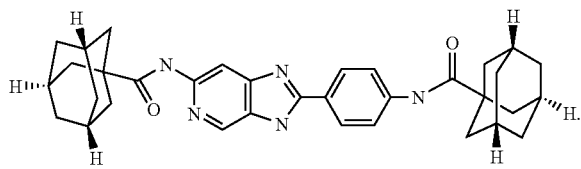

S-5

* * * * *